US009771597B2

(12) United States Patent
Hiatt et al.

(10) Patent No.: US 9,771,597 B2
(45) Date of Patent: Sep. 26, 2017

(54) METHODS AND COMPOSITIONS FOR ENHANCED FORAGE QUALITY

(71) Applicants: MONSANTO TECHNOLOGY LLC, St. Louis, MO (US); FORAGE GENETICS INTERNATIONAL, LLC, West Salem, WI (US)

(72) Inventors: William Hiatt, Rio Vista, CA (US); Marry S. Reddy, West Salem, WI (US); Mark McCaslin, West Salem, WI (US); Stephen Temple, West Salem, WI (US); David Whalen, West Salem, WI (US); Richard E. Cerny, Chesterfield, MO (US)

(73) Assignees: Forage Genetics International LLC, West Salem, WI (US); Monsanto Technology LLC, St. Louis, MO (US)

( * ) Notice: Subject to any disclaimer, the term of this patent is extended or adjusted under 35 U.S.C. 154(b) by 114 days.

(21) Appl. No.: 14/405,781

(22) PCT Filed: Jun. 26, 2013

(86) PCT No.: PCT/US2013/047911
§ 371 (c)(1),
(2) Date: Dec. 4, 2014

(87) PCT Pub. No.: WO2014/004683
PCT Pub. Date: Jan. 3, 2014

(65) Prior Publication Data
US 2015/0135370 A1 May 14, 2015

Related U.S. Application Data

(60) Provisional application No. 61/664,359, filed on Jun. 26, 2012.

(51) Int. Cl.
*C12N 15/82* (2006.01)
*C12Q 1/68* (2006.01)
*G01N 33/00* (2006.01)

(52) U.S. Cl.
CPC ..... *C12N 15/8255* (2013.01); *C12N 15/8218* (2013.01); *C12Q 1/6895* (2013.01); *G01N 33/0098* (2013.01); *C12Q 2600/13* (2013.01)

(58) Field of Classification Search
None
See application file for complete search history.

(56) References Cited

U.S. PATENT DOCUMENTS

| | | | |
|---|---|---|---|
| 7,449,617 B2 | 11/2008 | Dandekar et al. | |
| 7,566,817 B2 | 7/2009 | Beazley et al. | |
| 7,652,195 B2 | 1/2010 | Miller | |
| 7,663,023 B2 | 2/2010 | Dixon et al. | |
| 7,888,553 B2 * | 2/2011 | Dixon | C12N 9/1007 800/278 |
| 2004/0049802 A1 | 3/2004 | Dixon et al. | |
| 2005/0176670 A1 | 8/2005 | Huang et al. | |
| 2007/0079398 A1 | 4/2007 | Dixon et al. | |
| 2011/0229625 A1 | 9/2011 | Hiatt et al. | |
| 2012/0159664 A1 | 6/2012 | Abad et al. | |
| 2012/0272406 A1 * | 10/2012 | Guan | C12N 9/1011 800/285 |
| 2014/0259227 A1 | 9/2014 | Levering et al. | |
| 2016/0090604 A1 | 3/2016 | Hiatt | |
| 2017/0067068 A1 | 3/2017 | Levering et al. | |

FOREIGN PATENT DOCUMENTS

| | | |
|---|---|---|
| CA | 2 005 597 | 6/1990 |
| WO | WO 01/73090 | 10/2001 |
| WO | WO 2004/070020 | 8/2004 |
| WO | WO 2006/012594 | 2/2006 |
| WO | WO 2013-003558 | 1/2013 |

OTHER PUBLICATIONS

Jung et al 1997 J Dairy Sci 80:1622-1628, provided by Applicant.*
Hans-Joachim et al., "Modifying crops to increase cell wall digestibility," *Plant Science* 185-186:65-77, 2012.
Hatfield et al., "Can Lignin Be Accurately Measured?," *Crop Science* 45:832-839, 2005.
Jung et al., "Cell wall composition and degradability of stem tissue from lucerne divergently selected for lignin and in vitro dry-matter disappearance," *Grass and Forage Science* 49:295-304, 1994.
Riday et al., "Progress Report on Reduced-Lignin Alfalfa: Part I, Plant Modifications," *Forage Focus—USDA-ARS*, May 2009.
Extended European Search Report regarding European Application No. EP 13 80 8555, dated Feb. 16, 2016.
Carleton et al., "Seed Size Effects Upon Seedling Vigor of Three Forage Legumes," *Crop Science* 12(2):183-186, abstract, 1972.
Fang et al., "Multi-site genetic modulation of monolignol biosynthesis suggests new routes for formation of syringyl lignin and wall-bound ferulic acid in alfalfa (*Medicago sativa* L.)," *Plant J* 48(1):113-124, 2006.
Getachew et al., "Impacts of polyphenol oxidase enzyme expression in transgenic alfalfa on in vitro gas production and ruminal degration of protein, and nitrogen release during ensiling," *Animal Feed Sci. Tech.* 151:44-54, 2009.
Guo et al., "Downregulation of caffeic acid 3-O-Methyltransferase and caffeoyl 3-O-Methyltransferase in transgenic alfalfa: impacts on lignin structure and implications for the biosynthesis of G and S lignin," *Plant Cell* 13(1):73-88, 2001.
International Search Report and Written Opinion for International Application No. PCT/US2013/047911, dated Mar. 2, 2014.
International Search Report for International Application No. PCT/US2012/044590, dated Oct. 9, 2012.
Jung et al., "Correlation of Acid Detergent Lignin and Klason Lignin with Digestibility of Forage Dry Matter and Neutral Detergent Fiber," *Journal of Dairy Science* 80:1622-1628, 1997.
Marita et al., "Structural and compositional modifications in lignin of transgenic alfalfa down-regulated in caffeic acid 3-O-methyltransferase and caffeoyl coenzyme A 3-O-methyltransferase," *Phytochem* 62(1):53-65, 2003.

(Continued)

*Primary Examiner* — Brent Page
(74) *Attorney, Agent, or Firm* — Dentons US LLP

(57) ABSTRACT

The invention provides a method to select an alfalfa plant with enhanced feed value and increased flexibility in management either to increase quality of forage provided or to enhance biomass available earlier.

15 Claims, 2 Drawing Sheets

(56) References Cited

OTHER PUBLICATIONS

Mumm et al., "Quality control in the development of transgenic crop seed products," *Crop Science* 41:1381-1389, 2001.
Reisen et al., "Roundup ready alfalfa update and new biotech traits," 2009 WSHGA Annual Conference Proceedings, pp. 1-9, Jan. 1, 2009.
Sullivan et al., "Polyphenol oxidase and o-diphernois inhibit post-harvest proteolysis of red clover and alfalfa," *Crop Sci.* 46(2):662-670, 2006.
Taverniers et al., "Event-specific plasmid standards and real-time PCR methods for transgenic Bt11, Bt176, and GA21 maize and transgenic GT73 canola," *J. Agric. Food Chem.* 53:3041-3052, 2005.
Undersander, "Low-lignin alfalfa: redefining the yield/quality tradeoff," 2009 Western Alfalfa & Forage Conference, Alfalfa Leaf Image "Improving your odds of Profitability," Dec. 1, 2009.
Visarada et al., "Transgenic breeding: perspectives and prospects," *Crop Science* 49(5):1555-1563, 2009.
Guo et al., "Improvement of in-rumen digestibility of alfalfa forage by genetic manipulation of lignin O-methyltransferases," *Transgenic Res* 10(5):457-464, 2001.
Kust et al., "Influence of harvest management on levels of carbohydrate reserves, longevity of stands and yield so hay and protein from Vernal alfalfa," *Crop Sci.* 1:267-269, 1961.
Orloff et al.,"Intermountain Alfalfa Management," Steve B. Orloff, Editor Cooperative Extension Siskiyou County, CA, University of California, 1997.
Sheaffer et al., "Cutting schedules and stands," In A.A. Hanson et al. (ed.) Alfalfa and alfalfa improvement. Agron. Monogr. 29. ASA, CSSA, SSSA, Madison, WI, p. 411-437, 1988.
Smith et al., "Growth of birdsfoot trefoil and alfalfa. I. Responses to height and frequency of cutting," *Crop Sci.* 7:130-133, 1967.
University of Wisconsin Cooperative Extension, Minnesota Extension Center, University of Minnesota, Iowa State University, Alfalfa Management Guide, American Society of Agronomy, Crop Science Society of America, Soil Science Society of America, copyright, 2011.
Wiersma et al., "The long and short of Alfalfa cutting height," Focus on Forage, Marshfield Agriculture Research Station (MARS), updated 2007.
Inoue et al., "Developmental Expression and Substrate Specificities of Alfalfa Caffeic Acid 3-O-Methyltransferase and Caffeoyl Coenzyme A 3-O-Methyltransferase in Relation to Lignification," *Plant Physiol.* 117:761-770, 1998.
U.S. Appl. No. 15/356,348, filed Nov. 18, 2016, Levering et al.
USPTO: Non-Final Office Action regarding U.S. Appl. No. 15/356,348, dated Dec. 19, 2016.
GenBank Accession No. ER325305, dated May 26, 2010.
GenBank Accession No. GH365427, dated Dec. 31, 2008.
USPTO: Final Office Action regarding U.S. Appl. No. 13/029,500, dated Apr. 12, 2017.
USPTO: Non-Final Office Action regarding U.S. Appl. No. 14/885,530, dated Apr. 12, 2017.
GenBank Accession No. U20736, dated Aug. 7, 1998.

\* cited by examiner

METHODS AND COMPOSITIONS FOR ENHANCED FORAGE QUALITY

REFERENCE TO RELATED APPLICATIONS

This application is a 371 National Stage Entry of PCT/US2013/47911, filed Jun. 26, 2013, which claims the priority from U.S. Provisional Patent Application Ser. No. 61/664,359, filed Jun. 26, 2012, the entire disclosures of which are specifically incorporated herein by reference.

FIELD OF THE INVENTION

The invention relates to plant genetic engineering. More specifically, the invention relates to methods for improvement of the nutritional quality of a forage crop.

INCORPORATION OF SEQUENCE LISTING

The sequence listing file named MONS336US_ST25.txt," which is 18 kilobytes (size as measured in Microsoft Windows®) which was electronically filed and which was created on Dec. 4, 2014 is incorporated herein by reference.

BACKGROUND OF THE INVENTION

The invention provides methods and compositions through genetic engineering wherein a transgenic alfalfa plant has reduced levels of acid detergent lignin (ADL), reduced levels of guaiacyl lignin (G lignin), improved levels of neutral detergent fiber digestibility (NDFD), and plant vigor comparable to the wild type, resulting in improved agronomic fitness. Forage crops, including legumes, grasses, corn silage, and brassicas, among others, are grown throughout the world to provide animal feed with digestible fiber. Alfalfa and/or alfalfa grass hay is the most important hay crop in the United States. Although predominantly fed as baled hay, it can also be fed as silage, chopped hay, cubes, or pellets. Alfalfa (*Medicago sativa*) is a forage legume and may comprise 23% to 34% of dairy cattle feed. Quality alfalfa hay is highly digestible and provides high protein, energy, vitamins and minerals. Quality alfalfa also contains less celluloses and hemicelluloses, less lignin(s), lower fiber, and higher relative feed value. Alfalfa feed value is often measured as NDFD. Analyzing alfalfa forage for NDFD provides an estimation of the energy a cow is able to obtain from that forage, and there is a need to the enhance fiber digestibility in alfalfa. For example, an increase in one percentage unit NDFD results in a 0.37-pound increase in forage dry matter intake per day (lb/d), and a 0.55 lb/d increase in 4% fat corrected milk (FCM) yield. Cows fed forages with greater NDFD are able to obtain more total energy and nutritive value from the forages. As a result, the energy requirements can be fulfilled with less grain provided in the diet. Lower NDFD in forage legumes is most often related to the maturity of the forage plant, which is accompanied by an increase in lignin concentrations and associated with an increase in cellulose fibers.

Factors that affect NDFD include the amount of acid detergent fiber (ADF). ADF refers to the cell wall portions of the forage, which is the most indigestible part of forage and includes lignin, cellulose, silica, and insoluble forms of nitrogen. These values are particularly important because they relate to the digestibility of the forage by livestock. Forages with higher ADF are lower in digestible energy than forages with lower ADF. Thus, as the ADF level increases, the digestible energy levels decrease.

SUMMARY OF THE INVENTION

The invention provides a method and compositions through genetic engineering wherein a transgenic alfalfa plant may be selected for enhanced feed value components, such as reduced concentrations of ADL and G lignin, improved levels of NDFD in the lower stem resulting from at least equal vigor, and agronomic fitness compared to non-transgenic control plants not comprising the DNA molecules of the invention. Alfalfa events with reduced lignin are generated by using RNAi constructs to down regulate the lignin biosynthetic enzyme *Medicago sativa* S-adenosyl-L-methionine: caffeoyl-CoA 3-O-methyltransferase (CCoAOMT). All constructs utilized the stabilized antisense technology described in U.S. Patent Application publication 2005/0176670, incorporated herein by reference. The method to select events for reduced lignin alfalfa is "a reduction in the lignin content to provide an 8-15% increase in whole plant digestibility when cutting prior to the 10% bloom stage of maturity. The method selects an alfalfa plant from a population of alfalfa plants, wherein the population of alfalfa plants comprises recombinant DNA molecules that are homologous or complementary to SEQ ID NO:1 and SEQ ID NO:2. The method comprises assaying the lower stem of a population of alfalfa plants and selecting plants for: (1) a reduced concentration of acid detergent lignin, where the concentration of acid detergent lignin is reduced by between 12% and 31%; (2) a reduced concentration of guaiacyl lignin, where the concentration is reduced by about 25% or greater; (3) an increased neutral fiber digestibility, where the NDFD value is increased by greater than 18%, when compared to alfalfa plants not comprising such recombinant DNA molecules.

In one aspect of the invention, the selected alfalfa plant with enhanced feed value components has vigor substantially equal to an alfalfa plant not comprising said recombinant DNA molecule.

In another aspect, the invention provides a method to assay and select transgenic alfalfa plants with enhanced feed value components that have been transformed with a suppression construct for caffeoyl CoA 3-O-methyltransferase (CCoAOMT), SEQ ID NO:7, which further comprises a vascular-enhanced promoter to regulate transcription of recombinant DNA molecules that are homologous or complementary to SEQ ID NO:1 and SEQ ID NO:2.

In yet another aspect, the invention provides an alfalfa plant or progeny of the plant selected by the method of the present invention, or hay or silage derived from the plant or progeny plant, wherein the alfalfa plant or plant product comprises the DNA molecules that are homologous or complementary to SEQ ID NO:1 and SEQ ID NO:2, and comprises enhanced feed value components that are a result of reduced concentrations of ADL and G lignin, improved level of NDFD in the lower stem.

BRIEF DESCRIPTION OF THE FIGURES

The following drawings form part of the present specification and are included to further demonstrate certain aspects of the present invention. The invention may be better understood by reference to one or more of these drawings and their corresponding descriptions below, in combination with the detailed description of specific embodiments presented herein.

BRIEF DESCRIPTION OF THE SEQUENCES

Figure 1:
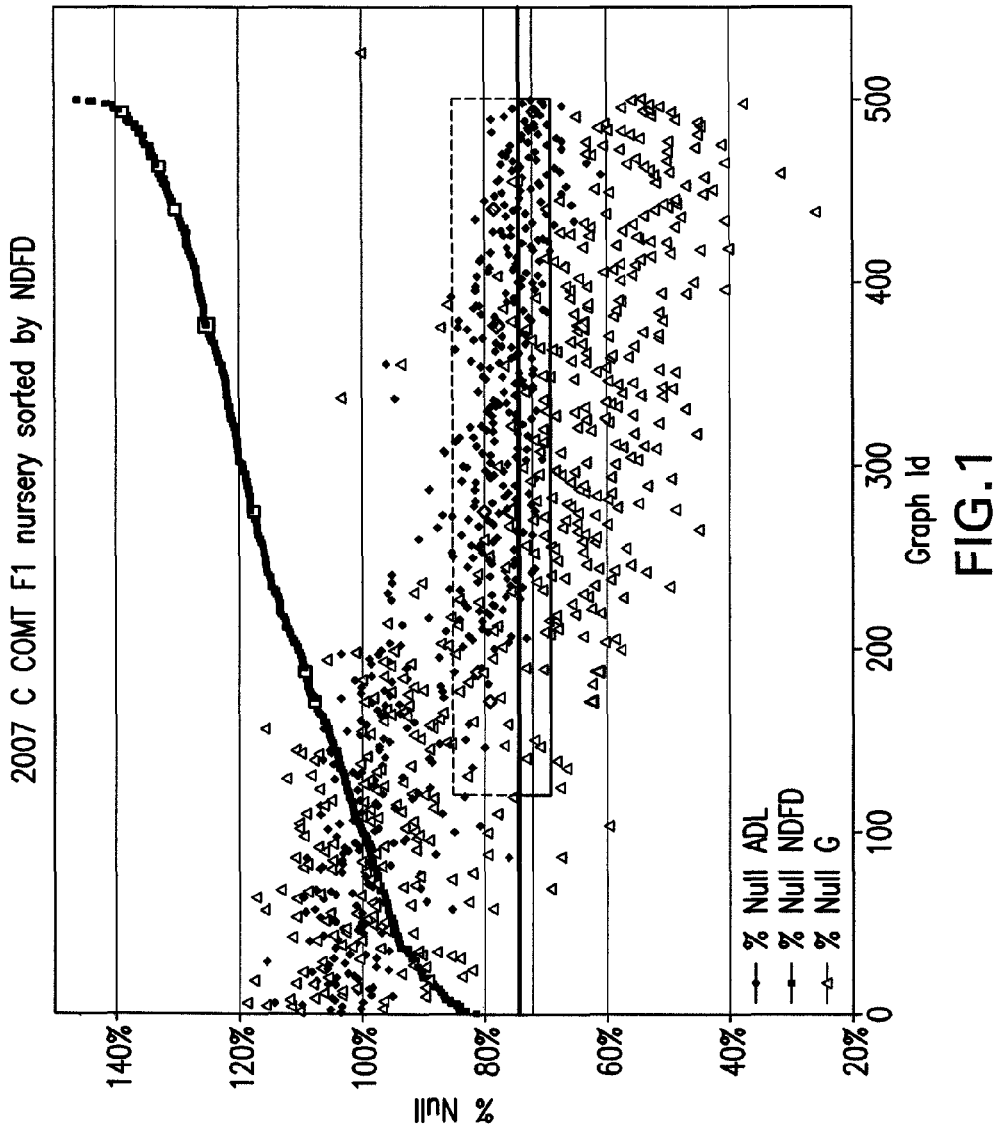
FIG. 1—Illustrates and outlines in black the elite transgenic alfalfa events with suppressed caffeoyl CoA 3-O-methyltransferase (CCoAOMT) that have an ADL concentration of between 80% and 91%; an NDFD value between 110% and 125%; and a lower G lignin value, compared to non-transgenic events.

SEQ ID NO:1—The sequence of the CCoAOMT gene 1139987:1 CR-*Medicago sativa* CCoAOMT-1:1:1 (sense direction).

SEQ ID NO:2—The sequence of the 1150536:1 CR-*Medicago truncatula* CCoAOMT-1:1:2 (antisense direction).

SEQ ID NO:3—The sequence of an RNA loop between the sense and antisense arm (374-530 bp).

SEQ ID NO:4—The sequence of the 5' end of the RNA loop (7-73 bp).

SEQ ID NO:5—The sequence of the 1141266:1 promoter (P)-Pv.Pal2-1:1:1.

SEQ ID NO:6—The sequence of the 1141267:1 leader (L)-Pv.Pal2-1:1:1.

SEQ ID NO:7—The sequence of pMON100052 CAS-Pv.Pal2//SUP-CCoAOMT//nos;CAS-CaMV.35S//npt2//nos.

DETAILED DESCRIPTION OF THE INVENTION

The present invention provides a method to select for enhanced feed value of forage crops in need of the enhancement. Aspects of the method can be applied to various forage crops, for example, including, but not limited to Alsike clover, Sainfoin, Lespedeza, Kura clover, Ladino clover, Red clover, white clover, sweet clover, Birdsfoot trefoil, Cicer milkvetch, Crown Vetch, *Medicago truncatula*, and alfalfa.

Methods according to the present invention may include, but are not limited to, a method to select transgenic forage crop alfalfa plants transformed with a recombinant DNA construct that reduces the expression or the activity of an S-adenosyl-L-methionine: caffeoyl-CoA 3-O methyltransferase (CCoAOMT or CCOMT) enzyme in the lignin biosynthetic pathway using the selection criteria of reduced acid detergent lignin (ADL), reduced guaiacyl lignin (G-lignin), increased neutral detergent fiber digestibility (NDFD), and at least substantially equal or improved vigor, compared to an alfalfa plant not transformed with the recombinant DNA construct. The combined selection criteria in the method of the invention allow for the selection of alfalfa plants with enhanced feed value. The invention relates to plants, plant parts, plant seeds, plant cells, agricultural products, and methods related to selecting and enhancing the nutrition of a forage crop.

The invention also provides a DNA molecule comprising a promoter molecule that functions in a vascular tissue of an alfalfa plant cell linked to a DNA segment corresponding to SEQ ID NO:1 (nucleotides 6583-6882 of SEQ ID NO:7) or a complement thereof. The invention also provides a DNA molecule comprising SEQ ID NO 1, linked to SEQ ID NO 3, linked to SEQ ID NO 2, which combination is comprised within the construct of SEQ ID NO:7). In another aspect of the invention is an alfalfa plant cell, plant part, hay, or seed comprising SEQ ID NO:1 or SEQ ID NO:2.

The present invention relates to a transgenic plant with improved economically important characteristics, more enhanced feed value. More specifically, the present invention relates to a transgenic plant comprising the nucleotide sequences of this invention, SEQ ID NO:1 or SEQ ID NO:2 of this invention and that enhanced feed value as compared to a non-transgenic control plant.

In a specific embodiment, "enhanced feed value" is described as reduced concentrations of ADL and G lignin, improved levels of NDFD in the lower stem resulting from at least equal vigor, and agronomic fitness compared to non-transgenic control plants not comprising the DNA molecules of the invention.

Plants of the present invention may pass along the recombinant DNA to a progeny. As used herein, "progeny" includes any plant, seed, plant cell, and/or a regenerated plant part comprising the recombinant DNA derived from an ancestor plant. Transgenic plants, progeny, and seeds may contain one, two, three or four copies of the transgene. In practicing the present invention, intercrossing of transgenic plants and selection for the transgene within segregating progeny may be used to increase trait purity. Back-crossing to a parental plant and out-crossing with a non-transgenic plant are also contemplated, as is vegetative propagation. Descriptions of other methods that are commonly used for different traits and crops can be found in one of several references, for example, Fehr, in *Breeding Methods for Cultivar Development*, Wilcox J. ed., American Society of Agronomy, Madison Wis. (1987).

The plants and seeds used in the methods disclosed herein may also contain one or more additional transgenes. Such transgene may be any nucleotide molecule encoding a protein or RNA molecule conferring a desirable trait including, but not limited to increased insect resistance, increased water use efficiency, increased yield performance, increased drought resistance, increased seed quality, improved nutritional quality, increased ruminal undegradeable proteins (RUP) and/or increased herbicide tolerance, in which the desirable trait is measured with respect to a forage plant lacking such additional transgene.

The lignin pathway starts with the conversion of phenylalanine to cinnamate by phenylalanine ammonia lyase (PAL). The second reaction is performed by cinnamate 4-hydroxylase (C4H) which converts cinnamate to 4-coumarate. These two enzymes form the core of the phenylpropanoid pathway including lignin biosynthesis. Other enzymes in the pathway include C3H or 4-coumarate 3-hydroxylase, which converts 4-coumaroyl shikimate or quinate to caffeoyl shikimate or quinate; HCT, hydroxycinnamoyl CoA: hydroxycinnamoyl transferase which acts at two places catalyzing the formation of 4-coumaroyl shikimate (or quinate), the substrate for C3H, from 4-Coumaroyl CoA, and also acting in the opposite direction on caffeoyl shikimate (or quinate), to yield caffeoyl CoA. CCoAOMT (caffeoyl-CoA 3-O-methyltransferase) converts caffeoyl CoA to feruloyl CoA and might also be involved in other reactions. COMT (caffeic acid O-methyl transferase) acts on 5-hydroxy coniferaldehyde and converts it into sinapaldehyde. Ferulate 5-hydroxylase (F5H) converts coniferaldehyde to 5-hydroxyconiferaldehyde. The DNA sequences of the lignin biosynthetic pathway enzyme genes from various plant species are disclosed in U.S. Patent Publ. No. 2007/0079398, and incorporated herein by reference. DNA sequences of the present invention include but are not limited to SEQ ID NOs:1-7.

Monolignols are incorporated into lignin in the form of the phenylpropanoids p-hydroxyphenyl (H), guaiacyl (G), and syringal (S) lignans, respectively. Dicotyledonous lignin is more often than not a mixture of G and S, and monocotyledonous lignin is a mixture of all three.

DNA constructs are made that contain various genetic elements necessary for the expression of noncoding and coding sequences in plants. Promoters, leaders, introns, transit peptide encoding polynucleic acids, and 3' transcriptional termination regions are all genetic elements that may be operably linked by those skilled in the art of plant molecular biology to provide a desirable level of expression or functionality.

A variety of promoters active in vascular tissues or tissues that accumulate lignin can be used to express the RNA molecule of the present invention. Promoters active in xylem tissue may include, but are not limited to, promoters associated with phenylpropanoid biosynthetic pathways, such as the phenylalanine ammonia-lyase (PAL) promoters, cinnamate 4-hydroxylase (C4H) promoters, coumarate 3-hydroxylase promoters, O-methyl transferase (OMT) promoters, 4-coumarate:CoA ligase (4CL) promoters (U.S. Pat. No. 6,831,208), cinnamoyl-CoA reductase (CCR) promoters and cinnamyl alcohol dehydrogenase (CAD) promoters (U.S. Pat. No. 7,429,649). Exemplary examples of a vascular promoters are the PAL promoters. In a preferred embodiment of the invention, the PAL2 promoter from *Phaseolus vulgares* is used to regulate the suppression of CCoAOMT gene(s) in alfalfa.

The laboratory procedures in recombinant DNA technology used herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual,* 2nd. ed., Cold Spring Harbor Laboratory, Cold Spring Harbor, N.Y. (1989), herein referred to as Sambrook et al., (1989).

Polynucleic acid molecules of interest may also be synthesized, either completely or in part, especially where it is desirable to provide modifications in the polynucleotide sequences, by well-known techniques as described in the technical literature, see, for example, Carruthers et al., Cold Spring Harbor *Symp. Quant. Biol.* 47:411-418 (1982), and Adams et al., *J. Am. Chem. Soc.* 105:661 (1983). Thus, all or a portion of the polynucleic acid molecules of the present invention may be of synthetic origin and can be modified as necessary to provide the desired result in the forage crop of choice.

The DNA construct of the present invention may be introduced into the genome of a desired plant host by a variety of conventional transformation techniques that are well known to those skilled in the art. Methods of transformation of plant cells or tissues include, but are not limited to *Agrobacterium* mediated transformation method and the Biolistics or particle-gun mediated transformation method. Suitable plant transformation vectors for the purpose of *Agrobacterium*-mediated transformation include those derived from a Ti plasmid of *Agrobacterium tumefaciens,* as well as those disclosed, for example, by Herrera-Estrella et al., Nature 303:209 (1983); Bevan, *Nucleic Acids Res.* 12:8711-8721 (1984); Klee et al., *Bio-Technology* 3(7): 637-642 (1985). In addition to plant transformation vectors derived from the Ti or root-inducing (Ri) plasmids of *Agrobacterium,* alternative methods can be used to insert the DNA constructs of this invention into plant cells. As used herein, the term "transformed" refers to a cell, tissue, organ, or organism into which has been introduced a foreign polynucleotide molecule, such as a construct. Preferably, the introduced polynucleotide molecule is integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. A plant transformation construct containing a DNA molecule of the present invention may be introduced into plants by any plant transformation method. Methods and materials for transforming plants by introducing a plant expression construct into a plant genome in the practice of this invention can include any of the well known and demonstrated methods, including electroporation as illustrated in U.S. Pat. No. 5,384,253; microprojectile bombardment as illustrated in U.S. Pat. No. 5,015, 580; U.S. Pat. No. 5,550,318; U.S. Pat. No. 5,538,880; U.S. Pat. No. 6,160,208; U.S. Pat. No. 6,399,861; and U.S. Pat. No. 6,403,865; *Agrobacterium*-mediated transformation as illustrated in U.S. Pat. No. 5,635,055; U.S. Pat. No. 5,824, 877; U.S. Pat. No. 5,591,616; U.S. Pat. No. 5,981,840; and U.S. Pat. No. 6,384,301; and protoplast transformation as illustrated in U.S. Pat. No. 5,508,184, all of which are incorporated herein by reference.

In one embodiment of the invention, such legumes may include alfalfa (lucerne; *Medicago sativa* or *Medicago falcata* or hybrids between them); other forage legumes similar to alfalfa that can be modified for enhanced feed value for ruminant animals, include white clover (*Trifolium repens*), red clover (T pretense), alsike clover (*T. hybridum*), sweet clover (*Melitotus alba* and *M. officinalis*) and subterranean clover (*T. subterranium*), sainfoin (*Onobrychis viciifolia*), big trefoil (*Lotus uliginosis*), birdsfoot trefoil (*L. corniculatus*), cicer milkvetch (*Astragalus cicer*), sericea (*Lespedeza cuneata*), Kobe lespedeza (*Kummerowia striata*), Korean lespedeza (*K. stipulacea*), trees, shrubs, and herbaceous plants in general.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

The following definitions and methods are provided to better define the present invention and to guide those of ordinary skill in the art of the present invention. Unless otherwise noted, terms are to be understood according to conventional usage by those of ordinary skill in the relevant art.

As used herein, the term "forage crop" means a forage legume, and includes all plant varieties that can be bred with the forage crop, including related wild forage species.

Alfalfa (*Medicago sativa*) is a forage legume often used for animal feed, especially dairy cattle. As used herein, the term "alfalfa" means any *Medicago* species, including, but not limited to, *M. sativa*, M. murex, *M. falcata, M. prostrata*, and *M. truncatula*. Thus, as used herein, the term "alfalfa" means any type of alfalfa including, but is not limited to, any alfalfa commonly referred to as cultivated alfalfa, diploid alfalfa, glandular alfalfa, purple-flowered alfalfa, sickle alfalfa, variegated alfalfa, wild alfalfa, or yellow-flowered alfalfa.

The invention provides DNA molecules and their corresponding nucleotide sequences. As used herein, the term "DNA", "DNA molecule", "polynucleotide molecule" refers to a double-stranded DNA molecule of genomic or synthetic origin, such as, a polymer of deoxyribonucleotide bases or a polynucleotide molecule, read from the 5' (upstream) end to the 3' (downstream) end. As used herein, the term "DNA sequence", "nucleotide sequence" or "polynucleotide sequence" refers to the nucleotide sequence of a DNA molecule.

"DNA construct" or "recombinant DNA molecule" refers to a combination of heterologous DNA genetic elements in operable linkage that is often used to provide new traits to a recipient organism. As used herein, the term "recombinant" refers to a form of DNA and/or protein and/or an organism that would not normally be found in nature and as such was created by human intervention. Such human intervention may produce a recombinant DNA molecule and/or a recombinant plant. As used herein, a "recombinant DNA molecule" is a DNA molecule comprising a combination of DNA molecules that would not naturally occur together and is the result of human intervention, for example, a DNA molecule that is comprised of a combination of at least two DNA molecules heterologous to each other, and/or a DNA molecule that is artificially synthesized and comprises a polynucleotide sequence that deviates from the polynucleotide sequence that would normally exist in nature. As used herein, a "recombinant plant" is a plant that would not normally exist in nature, is the result of human intervention, and contains a transgene and/or recombinant DNA molecule incorporated into its genome. A "DNA construct" as used in the present invention comprises at least one expression cassette, a promoter operable in plant cells, and the polynucleotide of the invention encoding a protein, variant of a protein, or fragment of a protein that is functionally defined to maintain activity in transgenic alfalfa, including plant cells, plant parts, explants, and plants. At least one expression cassette in a DNA construct as used herein may also comprise one or more polynucleotides that suppress the expression of at least one polypeptide encoding a trans-caffeoyl-CoA 3-O-methyltransferase (CCoAOMT) coding sequence in a target plant.

As used herein, the term "comprising" means "including but not limited to".

As used herein, the term "homologous or complementary" refers to polynucleotide molecules that generally demonstrate a substantial percent sequence identity with the plus sense or minus sense strands of the DNA molecules provided herein. Of particular interest are DNA molecules that share at least about 90% sequence identity, or even greater sequence identity, such as 98% or 99% sequence identity with the polynucleotide sequences described herein. Accordingly, the nucleotide sequences of the invention may be used for their ability to selectively form duplex molecules with complementary stretches of polynucleotide molecule fragments. Depending on the application envisioned, one may desire to employ varying conditions of hybridization to achieve varying degrees of selectivity towards target sequence.

Polynucleotide molecules of the present invention that are capable of regulating expression of an endogenous forage plant gene, caffeoyl-CoA 3-O-methyltransferase (CCoAOMT) and are substantially homologous to polynucleotide molecules that provide the same function and are encompassed within the scope of this invention.

"Operably linked" or "linked" is envisioned if a first nucleic-acid molecule is "operably" linked with a second nucleic-acid molecule when the first nucleic acid molecule is placed in a functional relationship with the second nucleic-acid molecule. For example, a promoter is operably linked to a DNA molecule if the promoter effects the transcription or expression of the DNA molecule. Generally, operably linked DNA molecules are contiguous, however, additional molecules may be included in a DNA construct that separate the physical linkage without affecting the functional linkage.

The term "promoter" or "promoter region" refers to a polynucleic acid molecule that functions as a regulatory element, usually found upstream (5') to a DNA coding sequence, that controls expression of the coding sequence by controlling the production of messenger RNA (mRNA), by providing the recognition site for RNA polymerase and/or other factors necessary for start of transcription at the correct site. As contemplated herein, a promoter or promoter region includes variations of promoters derived by means of DNA ligation to various regulatory sequences, random or controlled mutagenesis, and addition or duplication of enhancer molecules. The promoter region disclosed herein, and biologically functional equivalents thereof, are responsible for driving the transcription of coding sequences under their control when introduced into a host as part of a suitable recombinant vector, as demonstrated by its ability to produce mRNA. A DNA construct comprising a promoter can also be used to direct the transcription of noncoding RNA molecules.

The "3' non-translated sequences" are DNA sequences located downstream of a structural nucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA.

"Transformation" refers to a process of introducing an exogenous polynucleic acid molecule (for example, a DNA construct, a recombinant polynucleic acid molecule) into a cell or protoplast and the exogenous polynucleic acid molecule is incorporated into a host cell genome or an organelle genome (for example, chloroplast or mitochondria) or is capable of autonomous replication. "Transformed" or "transgenic" refers to a cell, tissue, organ, or organism into which a foreign polynucleic acid, such as a DNA construct or recombinant DNA molecule has been inserted. A "transgenic" or "transformed" cell or organism also includes progeny of the cell or organism and progeny produced from a breeding program employing, such a "transgenic" plant as a parent in a cross and exhibiting an altered phenotype resulting from the presence of the foreign polynucleic acid molecule. The use of *Agrobacterium*-mediated transformation to introduce DNA into dicotyledonous plants, including alfalfa and plant cells is well known in the art. See for example, the methods described by Fraley et al., (1985), Rogers et al., (1987) and U.S. Pat. No. 5,563,055, specifically incorporated herein by reference in its entirety. By plant transformation is meant the introduction of an external nucleic acid sequence into the plant genome. Transformation techniques include calcium phosphate transfection, DEAE-Betran transfection, electroporation, microinjection, protoplast fusion, and liposome-mediated transfection. Alternatively, a plant virus such as CaMV may be used as a vector for introducing foreign nucleic acid into plant cells or a high velocity ballistic penetration using small particles (Klein et al., 1987). A most preferred method for introducing nucleic acid segments into plant cells is to infect a plant cell or plant tissue with *Agrobacterium tumefaciens* which has been transformed with a selected nucleic acid segment (Horsch et al., 1984). Alfalfa was transformed following the protocol of McKersie et al., 1996. Other methods of alfalfa transformation either via, *Agrobacterium* or using other biological, chemical, or physical methods are feasible and thus may be used in the present invention. Methods for producing appropriate vectors, for transforming cells with those vectors and for identifying transformants are described in the scientific literature, as for example, but not limited to, Sambrook et al. (1989), *Molecular Cloning: A Laboratory Manual*, Cold Spring Harbor Laboratory Press, Cold Spring Harbor, N.Y., Gelvin and Schilperoort (1991) *Plant Molecular Biology Manual*, Kluwer Academic Press, and more importantly in Glick, B. R. and Thompson, J. E. 1993, *Methods in Plant Molecular Biology and Biotechnology*, CRC Press, Boca Raton.

As used herein, the term "transgene" refers to a polynucleotide molecule artificially incorporated into a host cell's genome. Such transgene may be heterologous to the host cell. The term "transgenic plant" refers to a plant comprising such a transgene. "Transgene" also encompasses the component parts of a native plant gene modified by insertion of a nonnative polynucleic acid molecule by directed recombination or site specific mutation. A recombinant DNA molecule inserted into the genome of a plant is a transgene. A "transgene" is defined as a segment of DNA which has been incorporated into a host genome or is capable of autonomous replication in a host cell and is capable of causing the expression of one or more coding sequences. Exemplary transgenes will provide the host cell, or plants regenerated from the host cell with an enhanced phenotype relative to the corresponding non-transformed cell or plant. Transgenes may be directly introduced into a plant by genetic transformation, or may be inherited from a transgenic progeny plant.

"Transformation vectors" of this invention used for transformation may contain one or more "expression cassettes", each comprising a native or non-native plant promoter operably linked to a polynucleotide sequence of interest, which is operably linked to 3' UTR termination signal, for expression in an appropriate host cell. Transformation vectors also typically comprise sequences required for proper translation of the nucleotide sequence or transgene. As used herein, the term "transgene" refers to a polynucleotide molecule artificially incorporated into a host cell's genome. Such a transgene may be heterologous to the host cell. The term "transgenic plant" refers to a plant comprising such a transgene. The coding region usually codes for a protein of interest but may also code for a functional RNA of interest, for example antisense RNA, a nontranslated RNA, in the sense or antisense direction, a microRNA, a noncoding RNA, or a synthetic RNA used in either suppression or over expression of target gene sequences. The expression cassette comprising the nucleotide sequence of interest may be chimeric, meaning that at least one of its components is heterologous with respect to at least one of its other components. As used herein the term "chimeric" refers to a DNA molecule that is created from two or more genetically diverse sources, i.e. a first molecule from one gene or organism and a second molecule from another gene or organism. A "transformation construct" is a chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

"Regeneration" refers to the process of growing a plant from a plant cell (for example, a protoplast, callus, or explant).

The term "plant" includes whole plants, shoot vegetative organs/structures (for example, leaves, stems and tubers), roots, flowers and floral organs/structures (for example, bracts, sepals, petals, stamens, carpels, anthers, and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. A plant refers to a whole plant, as well as to a plant part, such as seed, fruit, leaf, or root, plant tissue, plant cells or any other plant material, for example, a plant explant, as well as to progeny thereof, and to in vitro systems that mimic biochemical or cellular components or processes in a cell.

A "control plant" as used in the present disclosure refers to a plant cell, seed, plant component, plant tissue, plant organ, or whole plant used to compare against transgenic or genetically modified plant for the purpose of identifying an enhanced phenotype in the transgenic or genetically modified plant. A control plant may in some cases be a transgenic plant line that comprises an empty vector or marker gene, but does not contain the recombinant polynucleotide of the present invention that is expressed in the transgenic or genetically modified plant. A control plant may in other cases be a progeny of a hemizygous transgenic plant line that does not contain the recombinant DNA, known as a negative segregant or negative isoline. In general, a control plant is a plant of the same line or variety as the transgenic or genetically modified plant being tested. A suitable control plant may include a genetically unaltered or non-transgenic plant of the parental line used to generate a transgenic plant herein.

A "transgenic plant" refers to a plant that contains genetic material not found in a wild-type plant of the same species, variety, or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes. A transgenic plant may contain an expression vector or cassette. A "transgenic plant" is a plant or progeny plant of any subsequent generation that is derived from the plant or progeny, wherein the plant or progeny contains an introduced exogenous DNA molecule not naturally present in a non-transgenic plant. The transgenic plant may additionally contain sequences which are native to the plant being transformed, but wherein the "exogenous" gene has been altered in order to alter the level or pattern of expression of the gene, for example, by use of one or more heterologous regulatory or other elements.

"Wild type" or "wild-type", as used herein, refers to a plant cell, seed, plant component, plant part, plant tissue, plant organ, or whole plant that has not been genetically modified or treated in an experimental sense. Wild-type cells, seeds, components, parts, tissues, organs, or whole plants may be used as controls to compare levels of expression, the extent and nature of trait modification with cells, tissue or plants of the same species, variety or cultivar in which a polypeptide's expression is altered, for example, in that it has been knocked out, overexpressed, or ectopically expressed.

An $R_0$ transgenic plant refers to a plant that has been genetically transformed or has been regenerated from a plant cell or cells that have been genetically transformed.

A "population" of plants refers to a local group of organisms of the same species that can under normal conditions interbreed and share similarity among the frequencies of alleles and genotypes within that population.

As used herein, the term "callus" refers to a clump of undifferentiated plant cells that are capable of repeated cell division and growth, and in some species, can be induced to form a whole plant.

As used herein, the term "somatic tissues" refers to tissues not including germ cells or gametes. Somatic tissues are composed of vegetative tissues and cells.

As used herein, the term "somatic embryogenesis" refers to the process of embryo initiation and development from vegetative or non-gametic cells. The embryos from a given tissue source are presumed to be genetically identical. Somatic embryogenesis is an important pathway for the regeneration of plants from cell culture systems and a method commonly used in large scale production of plants and synthetic seeds (Stuart et al. 1987). In somatic (asexual) embryogenesis, embryo-like structures develop into whole plants in a way analogous to zygotic embryos formed from somatic tissues. Somatic embryos can be produced from a cell or small group of cells without the production of an intervening callus. Somatic embryos can also be produced from an intermediary callus tissue or from a cell suspension produced from that callus. Somatic embryogenesis is one of a number of methods known in the art for the propagation of desirable species or varieties of plants. There are many advantages which favor somatic embryogenesis as a propagative method of choice. One advantage is that a plant which has a known and desirable phenotype can be chosen as the source of cells, and, in accordance with somatic embryogenesis techniques, these cells can be rapidly cultured into many genetically uniform embryos. The resulting embryos can then be cultivated into entire plants possessing roots and shoots. Thus, in accordance with this technique, plants with the same desirable phenotype as the parent can be mass produced, potentially at costs comparable to and often more quickly and with better genetic uniformity than other propagative techniques such as described in U.S. Pat. No. 5,187,092 incorporated herein by reference.

Cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Various types of media suitable for culture of plant cells have been previously described. Examples of these media include, but are not limited to, the medium described by Schenk and Hildebrandt formulation (1972). Embryogenic callus cultures may be used with certain transformation techniques for the preparation of cells for transformation and for the regeneration of forage plants, for example, alfalfa. Schenk and Hildebrant medium formulation (S&H media, 1972) was used in the transformation and maintenance of embryogenic tissue cultures. The S&H medium is a mixture of various categories of ingredients (salts, amino acids, growth regulators, sugars, buffers) that are required for growth of most cell types. The S&H media, pH at 5.8, provides a mixture of macro-nutrients, micro-nutrients, vitamins, iron that is supplemented with hormones, 2,4-D at a final concentration of 0.2 µM and kinetin at a concentration 0.5 µM. Under selective conditions primary somatic embryos are visible after 12-15 weeks.

As used herein, the term "explant" refers to a piece of tissue taken from a donor plant for culturing.

A "host cell" may be defined as a cell invaded by or capable of being invaded by an infectious agent. A host cell that has been transformed with DNA (or RNA), such as a bacterial cell acting as a host cell of recombinant DNA, is capable of replicating the recombinant DNA reproduced along with the host cell. A reference to a "host cell" includes a plurality of such host cells. Suitable host cells for the introduction of recombinant DNA include but are not limited to plant cells, bacterial cells, yeast cells, insect cells, synthetic cells or a combination thereof. A synthetic host cell can encompass a chemically synthesized chromosome transplanted into a cell to produce a synthetic cell (for example, a synthetic bacterium), which is capable of self replicating. The genomes of synthetic bacterial host cells may be assembled in naturally grown host cells (for example, yeast host cells). Synthetic host cells are particularly useful for making a minimal synthetic genome containing all of the properties of a living.

The term "expression" refers to the combination of intracellular processes, including transcription and translation undergone by a coding DNA molecule such as a structural gene to produce a polypeptide.

The term "suppression" as used herein refers to a lower expression level of a gene in a plant, plant cell or plant tissue, compared to the expression in a wild-type or control plant, cell or tissue, at any developmental or temporal stage for the gene. Suppression can be applied using numerous approaches; to suppress a mutation that has resulted in decreased activity of a protein, to suppress the production of an inhibitory agent, to elevate, reduce or eliminate the level of substrate that a enzyme requires for activity, to produce a new protein; or to activate a normally silent gene, to accumulate a product that does not normally increase under natural conditions. The suppressor can be another mutation on a different gene, a suppressor mutation on the same gene but located some distance from the first mutation, or a suppressor in the cytoplasm that has generated due to a change in non-chromosomal DNA. There are multiple approaches to suppress a gene, for example, RNAi-mediated gene suppression can be used to suppress the expression of targeted genes within plants. A recombinant DNA construct comprising a promoter that is functional in a plant cell and that is operably-linked to a polynucleotide that when expressed in a plant cell is transcribed into an RNA molecule that suppresses the level of an endogenous protein in the plant cell relative to a control, wherein the RNA molecule is a dsRNA which is processed into siRNAs which targets a messenger RNA encoding the protein; a miRNA that targets a messenger RNA encoding the protein; a ta-siRNA which is processed into siRNAs and which targets a messenger RNA encoding the protein; or is transcribed into an RNA molecule resulting in the suppression of a miRNA activity relative to a control, and wherein a RNA molecule is a cleavage blocker of a miRNA or is a miRNA decoy of a miRNA (Examples of such RNAi-mediated gene suppression approaches are disclosed in U.S. Patent Publ. 2009/61288019 and incorporated herein by reference). "Suppression" refers to a plant or plant cell having a disruption in at least one gene in the plant or cell, where the disruption results in a reduced expression or activity of the polypeptide encoded by that gene compared to a control cell. The knockout can be the result of, for example, genomic disruptions, including transposons, tilling, and homologous recombination, antisense constructs, sense constructs, RNA silencing constructs, or RNA interference. A T-DNA insertion within a gene is an example of a genotypic alteration that may abolish expression of that gene.

In the selection of an "event", a transformation construct responsible for a trait is introduced into the genome via a transformation method. Numerous independent transformants (events) are usually generated for each construct. These events are evaluated to select those with superior performance. The event evaluation process is based on several criteria including: 1) transgene expression and phenotype "efficacy" of the trait; 2) molecular characterization of the trait, such as the selection of events showing a clean single intact insert are found by conducting molecular assays for copy number, insert number, insert complexity, presence of the vector backbone, and development of event-specific assays and are used for further development; 3) segregation of the trait, segregation of the trait is tested to select transgenic events that follow a single-locus segregation pattern. A direct approach is to evaluate the segregation of the trait; 4) agronomics of the developed event; and 5) stability of the transgenic trait expression. Evaluation of large populations of independent events and more thorough evaluation result in the greater chance of success. The stability of transgenic trait expression is ascertained by testing in different generations, environments, and in different genetic backgrounds. Events that exhibit unstable phenotype efficacy are discarded. Generally, events with a single intact insert that inherited as a single dominant gene and follow Mendelian segregation ratios are used in commercial trait integration strategies such as backcrossing and forward breeding.

"G lignin" refers to guaiacyl lignin. Guaiacyl lignin is composed principally of coniferyl alcohol units, while guaiacyl-syringyl lignin contains monomeric units from coniferyl and sinapyl alcohol. In general, guaiacyl lignin is found in softwoods, while guaiacyl-syringyl lignin is present in hardwoods.

"Enhance feed value" refers to the forage quality, such as fiber content, digestibility, and available carbohydrate resources available to livestock. Enhanced feed value or alfalfa quality is determined by the Relative Feed Value (RFV) expressed as a percentage of alfalfa at 100% bloom and is used as a predictor of feed value in the field. Components that effect feed value are acid detergent lignin concentration and G lignin and neutral detergent fiber digestibility. The measurement of these feed value components is an aspect of the invention.

Plant "vigor" is a measure of agronomic fitness, such as plant growth, foliage volume, or biomass over a set period of time after planting.

"Acid detergent lignin" (ADL) is an estimate of lignin content. Lignin is an indigestible component of forage fiber (NDF) that is believed to limit the extent to which forage fiber can be digested by ruminant animals.

"Neutral Detergent Fiber Digestibility" (NDFD) content of forage is a measure of the digestibility of a forage fiber and can be measured in vitro and predicted using Near Infrared Reflectance Spectroscopy (NIRS). The higher the NDFD value the more digestible the forage.

The "lower stem" of the alfalfa plant is described as the 15-cm stem sections of the stems of the alfalfa plant that have been harvested 2.5" above ground level with the leaves completely removed. The lower stem is the most lignified part of the alfalfa plant, and the least digestible.

Alfalfa is generally harvested as alfalfa "hay" or "silage", the differences between the two being based on percent moisture and crude protein. For alfalfa silage, digestible protein should be 60% to 70% of crude protein. For example, in alfalfa silage, digestible protein should be 60% to 70% of crude protein). Alfalfa is most often harvested as "hay" and can be stored as bales or stacks but can also be made into silage, grazed or fed as greenchop. For the purposes of this invention "whole plant" is the equivalent of "hay". On a dry matter basis, cattle livestock eat more silage than hay. Silage or haylage is made from direct-cut alfalfa.

As used herein, "ruminal undegradable protein" or "RUP" refers to a measure of feed quality. The feed quality "nutritive value" of alfalfa may be greatly improved by an increase in its RUP concentration. Forage proteins are often not utilizable by ruminants because they are degraded during silage fermentation and thus an increase in RUP concentration in alfalfa enhances its nutritive value.

As used herein, "a" or "an" may mean one or more. As used herein in the claim(s), when used in conjunction with the word "comprising," the words "a" or "an" may mean one or more than one.

As used herein the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

EXAMPLES

The following examples provide illustrative embodiments of the invention. However, those of skill in the art should, in light of the present disclosure, appreciate that many changes can be made in specific aspects of these embodiments without departing from the concept, spirit, and scope of the invention. Moreover, it is apparent that certain agents which are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

Example 1

Plant Expression Constructs for Alfalfa Transformation

This example illustrates the construction of expression constructs for transferring recombinant DNA into an alfalfa plant cell nucleus that can be regenerated into transgenic alfalfa plants. The transformation vector pMON100052 (also known as pFG118) comprising the elements as described in Table 1, was fabricated for use in preparing recombinant DNA for *Agrobacterium*-mediated transformation into alfalfa tissue for suppressing Caffeoyl-CoA3-O-methyltransferase (CCoAOMT) comprising the sequences identified as SEQ ID NO:1 and SEQ ID NO:2 of this invention. The alfalfa cell, plant part, or plant was transformed with the expression cassette SEQ ID NO:7 of this invention, which comprises the Pv.PAL2 promoter from *Phaseolus vulgaris* that allows for the controlled expression of the CCoAOMT polypeptide in sites of lignin deposition. The expression cassette can be introduced into a plant by transformation or by breeding after transformation of a parent plant and harvesting of progeny seed.

Organ Cult, 1:109-121, 1981). The neomycin phosphotransferase gene, which confers resistance to neomycin and kanamycin, was used as a selectable marker to select transformed material, which was then transferred to shoot induction medium supplemented with ticarcillin (250 μg/mL) or Timentin (150 μg/mL). Transformed plants were transferred to soil in approximately 20-24 weeks. When shoots had formed, they were rooted and initially placed in Magenta

TABLE 1

Elements of transformation vector pMON100052 (also known as pFG118)

| Function | Name | Annotation | Coordinates of SEQ ID NO: 36444 |
|---|---|---|---|
| *Agrobacterium* T-DNA transfer | B-AGRtu.left border | Agro left border sequence, essential for transfer of T-DNA. | 1516-1957 |
| Plant selectable marker expression cassette | L-CaMV.35S | 5'UTR of 35S RNA from CaMV gene | 1142-1172 |
| | P-CaMV.35S | Promoter for 35S RNA from CaMV containing a duplication of the −90 to −350 region. | 1173-1465 |
| | CR-Ec.nptII-Tn5 | Coding region for neomycin phosphotransferase gene from transposon Tn5 which confers resistance to neomycin and kanamycin. | 314-1108 |
| | T-AGRtu.nos | A 3' non-translated region of the nopaline synthase gene of *Agrobacterium tumefaciens* Ti plasmid which functions to direct polyadenylation of the mRNA. | 30-282 |
| Gene of interest expression cassette | L-Pv.Pal2 | 5'UTR of *Phaseolus vulgaris* PAL2 gene | 7426-7479 |
| | P-Pv.Pal2 | Promoter from the *Phaseolus vulgaris* PAL2 gene | 7480-8502 |
| | GOI | A polynucleotide or polypeptide-coding SEQ ID NO: 1 *Medicago sativa* CCoAOMT gene or SEQ ID NO: 2 *Medicago truncatula* CCoAOMT gene | 6322-6882 |
| | T-AGRtu.nos | A 3' non-translated region of the nopaline synthase gene of *Agrobacterium tumefaciens* Ti plasmid which functions to direct polyadenylation of the mRNA. | 6322-6574 |
| *Agrobacterium* T-DNA transfer | B-AGRtu.right border | Agro right border sequence, essential for transfer of T-DNA. | 10196-10552 |

Alfalfa clone R2336, selected from elite germplasm, was transformed with the DNA construct, pFG118 (SEQ ID NO:8; pMON100052) comprising a DNA segment complimentary to the coding sequence of caffeoyl-CoA 3-O-methyltransferase (CCoAOMT) using *Agrobacterium* strain ABI. All RNAi constructs to generate reduced lignin transgenic events by down regulating the lignin biosynthetic enzyme CCoAOMT from *Medicago sativa* utilized the stabilized antisense technology described in U.S. Patent Publication No. US2005/0176670, incorporated herein by reference. Two different coding sequences were used in the transformation construct pMON100052, one encoding the RNAi arm and loop for the CCoAOMT gene (SEQ ID NO:1) containing a 5' end of the RNA loop, and the other sequence (SEQ ID NO:2) containing an antisense arm, loop (374-530 bp) and sense arm (531-836 bp) to suppress or downregulate the expression of the CCoAOMT enzyme. In the pMON100052 construct, the expression of the genes used to suppress the CCoAOMT gene was regulated under the control of a single PAL2 promoter from *Phaseolus vulgarus*. Transformation of leaflets or leaf-derived explants from alfalfa clone R2336 was carried out using a standard *Agrobacterium* method (Walker and Sato, Plant Cell Tissue boxes and subsequently in pots containing a sterilized vermiculite:perlite mix at a ratio of 5:1 combined with an equal amount of potting Pro-mix PGX containing biofungicide (Hummert, Cat. No. 10-2093) and maintained under moderate light at 25-26° C. The plants were maintained under sealed conditions either under Magenta box covers or sealed with thin plastic bags for a period of 7-10 days, after which time the humidity was gradually reduced as the plants acclimated. Plants were fertilized with a general purpose fertilizer. Once plants were established, they were transferred to a conventional soil mix and transferred to the greenhouse.

Example 2

Identification of Sequences for Suppression of Caffeoyl-CoA3-O-Methyltransferase (CCoAOMT)

This example illustrates phenolic acid analysis of transgenic alfalfa expressing a DNA construct for the suppression of expression of an enzyme in the lignin biosynthetic pathway. Alfalfa cells were transformed with a DNA construct comprising a DNA segment (SEQ ID NO:7) complimentary to a caffeoyl-CoA 3-O-methyltransferase (CCoAOMT) coding sequence in order to down regulate the expression of the enzyme. The resultant transgenic alfalfa plant cell, plant part, or plant comprised a recombinant DNA molecule of this invention, wherein a portion of the DNA molecule is homologous or complementary to SEQ ID NO:1 or SEQ ID NO:2.

Example 3

Selection Method for Alfalfa Plants with Reduced Acid Detergent Lignin

Acid detergent fiber (ADF) was measured by modifications to standard protocols of Goering and Van Soest (Forage Fiber Analysis, *USDA Agricultural Handbook No. 379*, 1970). Powdered samples (0.35 g) were placed in an F57 ANKOM filter bag (ANKOM Technology Corporation, Fairport, N.Y.), and heated at 100° C. with agitation for 1 h in the respective solutions in an ANKOM Fiber Analyzer. After washing in near boiling water, samples were dried at 105° C. for 6 h, and then weighed to determine fiber loss. ADL determinations were performed on the residue from ADF determination by incubation in 72% (v/v) sulfuric acid for 3 h, washing thoroughly, and drying for 6 h at 105° C. prior to weighing (Guo et al., *Transgenic Res*, 10(5):457-464, 2001).

Samples (30 mg) were dried overnight at 50° C. before weighing into glass culture vial (16×150 mm) fitted with Teflon lined screw caps. Samples were heated for 4 h at 50° C. after adding 3 mL of freshly prepared 25% (v/v) acetyl bromide in glacial acetic acid. After cooling down the samples, 3 mL of acetic acid were added into the tubes and centrifuged at 3000 rpm for 5 min. An aliquot (5 mL) of the upper layer was quantitatively transferred to a 50-mL volumetric flask that contained 10 mL of 2 M NaOH and 12 mL of acetic acid. Hydroxylamine (1 mL of 0.5 M) was added to each flask and samples were diluted to 50 mL with acetic acid. Absorption spectra (250 to 350 nM) were determined for each sample and used to determine the absorption maxima at 280 nm. The following regression equation was used: Acetyl bromide lignin (mg/ml)=absorbance reading/F, where F=17.20 for young tissue and F=17.12 for mature tissue.

Thioacidolysis and Lignin Composition

Three milliliters of thioacidolysis reagent [2.5% boron trifluoride etherate and 10% ethanethiol, in dioxane (v/v)] was added to 30 mg dried ground sample in a 15-mL glass vial. The sealed vial was then placed into an oil bath (>80° C.) for 4 h with periodic (every 30 min) manual agitation. The reaction was stopped by placing the vial on ice. Internal standard (200 μL), water (3 mL), and saturated sodium bicarbonate (until pH ~3 to 4) were added. The mix was vortexed and allowed to settle. The lower layer (methane chloride containing the lignin breakdown products) was transferred to another glass vial. The aqueous layer was extracted two more times with 3 mL methane chloride. The methane chloride layers were combined and dried over anhydrous sodium sulfate. An aliquot (3 mL) was dried under nitrogen. The dried extracted lignin monomers were derivatized with 25 microliter (μL) pyridine and 80 μL N-Methyl-N-(trimethylsilyl)trifluoroacetamide (MSTFA). After incubation for 30 min at 37° C., 0.5 μL of this reaction product was analyzed by GC/MS. The GC/MS was performed on a Hewlett Packard 5890 series II gas chromatograph with a 5971 series mass selective detector (column: HP-1, 60 m×0.25 mm×0.25 μm film thickness), and the mass spectra were record in electron impact mode (70 eV) with a 60 to 650 m/z scanning range.

Example 4

Alfalfa Plants with Enhanced Feed Value Components

Alfalfa (*Medicago sativa* L.) is one of the most important forages in the United States. Increasing alfalfa fiber digestibility would improve forage quality, ration formulation flexibility, and enhance feed value. Currently, growers and breeders relay on near infrared spectroscopy (NIRS) to predict forage quality traits for alfalfa. With the introduction of lignin down regulated alfalfa plants, the NIRS methods of analysis and equations are accurate for predicting forage quality traits for novel low-lignin alfalfa samples. NIR analysis has been used for the prediction of lignin content and composition, for example to determine Klason lignin and in the ration of syringl (S-lignin) to guaiacyl (G-lignin) sub-units (Bailléres et al., 2002). This example reports in vitro neutral detergent fiber digestibility (NDFD) and lignin analysis (ADL, Klason, total thioacidolysis yield, S-lignin, and G-lignin of caffeic acid 3-O-methyltransferase (COMT) and caffeoyl CoA 3-O-methyltransferase (CCoAOMT) down-regulated alfalfa.

Amounts of ADL as a percentage of dry matter (DM), and NDFD as a percentage of neutral detergent fiber were calculated using the NIRS equation developed separately for lower stem and whole plant samples using tissues of transgenic alfalfa (40 COMT and 40 CCoAOMT down-regulated plants) and 20 non-transgenic control null-type alfalfa plants. Chemical analyses generated total amounts of lignins in the lower stem of alfalfa plants, which comprised measurements for ADL, Klason lignin, total thioacidolysis lignin, S-lignin, G-lignin, and H-lignin represented on a percentage of DM basis.

Lower stem samples of 40 COMT, 40 CCoAOMT, and 20 null-type alfalfa plants were collected over three locations from a total of 10 harvested by location combinations, which equals a total of 2900 field samples. The results of NIRS analysis indicated lower lignin and higher digestibility for COMT and CCoAOMT transgenic alfalfa stems. The results also revealed that the relative values among down regulated alfalfa differed for thioacidolysis measured lignin compared to ADL and Klason lignin. Total thioacidolysis yield appeared to be the best predictor of NDFD. In particular, S-lignin levels were highly correlated with NDFD in the alfalfa stem tissues.

Table 2 provides a summary of the ADL and NDFD values represented as a percent of the non-transgenic alfalfa control plants for the reduced lignin alfalfa transgenic event, KK179-2, compared to the Round-up Ready (RR) event in the whole plant, which is equivalent to hay (A) and the lower stem (B). Column 1 identifies alfalfa transgenic event KK179-2 and the Round-up Ready (RR) event. Column 2 provides average amounts of ADL represented as a percent of the non-transgenic alfalfa control plant. Column 3 provides average amounts of NDFD as a percent of the non-transgenic alfalfa control plant.

TABLE 2

Comparison of ADL and NDFD analysis between transgenic alfalfa event KK179-2 with pMON100052 and Round-up (Ready RR) alfalfa event J-101 (ATCC Accession No. PTA-4814, as described in U.S. Pat. application No. 7,566,817).

A. Whole

| Entry | ADL % control | NDFD % control |
|---|---|---|
| RKK179 | 90.82 | 121.69 |
| RR only | 100 | 100 |
| RKK179 | 82.05 | 125.3 |
| RR only | 100 | 100 |
| RKK179 | 85.88 | 111.37 |
| RR only | 100 | 100 |

B. Lower

| Entry | ADL % control | G Lignin % control | NDFD % control |
|---|---|---|---|
| RKK179 | 83.84 | 778.41 | 135.2 |
| RR only | 100 | 100 | 100 |
| RKK179 | 80.79 | 78.63 | 138.46 |
| RR only | 100 | 100 | 100 |
| RR/RL 2 | 75.94 | 73.63 | 136.19 |
| RR/-2 | 100 | 100 | 100 |

Figure 2:
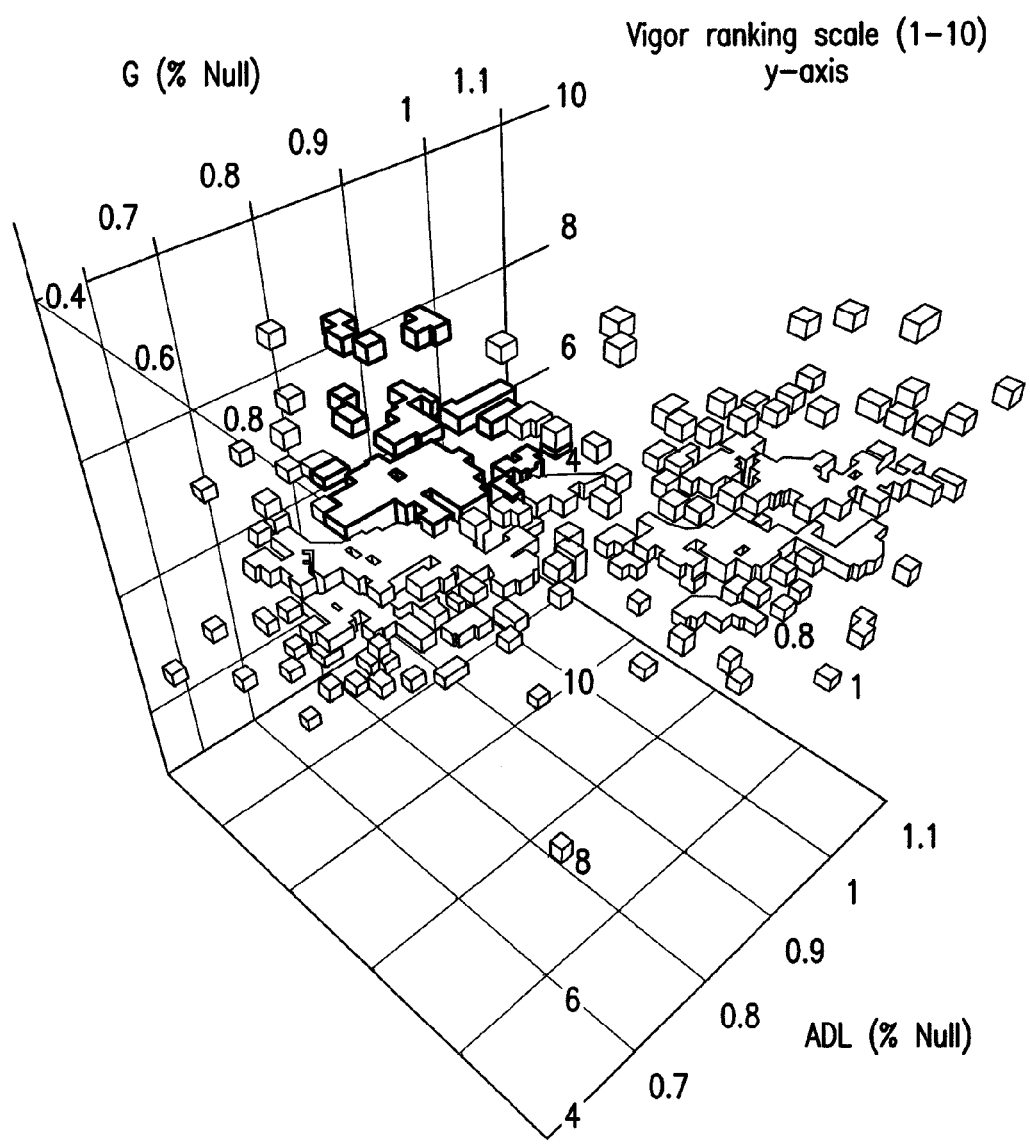
FIG. 2—Illustrates elite events and reduced lignin alfalfa events for KK179-2 that meet the required performance criteria based on the levels on percent ADL, NDFD, and vigor for enhanced forage digestibility and enhanced nutritive quality, defined as the "sweet spot."

Table 3 shows raw data values used to create "Sweet Spot" selection for reduced lignin alfalfa events represented in FIG. 2, as defined by performance criteria based on percent ADL, percent G lignin, a measure of NDFD, and a vigor rating score. Column 1 provides the graph identification number associated with the individual alfalfa plants (shown in FIG. 2). Column 2 provides the event designation. Column 3 contains vigor rating scores of ranked from 1-10, with a score of 10 resulting in the best vigor. Column 4 provides mean ADL measurements. Column 5 provides a percent ADL measurement based on the comparison to the non-transgenic null control plants. Column 7 provides a measurement for mean NDFD. Column 8 provides a measure of percent NDFD based on the comparison to the non-transgenic null control plants. Column 9 provides a measurement of mean G lignin. Column 10 provides a percent G lignin measurement based on the comparison to the non-transgenic null control plants. Alfalfa events that met the performance criteria were classified as follows: ADL concentration in the lower stem reduced by between approximately 15 to 30%, and an ADL concentration of between 80 to 91%, a reduction in G lignin by at least 25%, and an NDFD value between 110 and 125%, relative to events with an ADL and NDFD value of alfalfa hay below the performance criteria.

TABLE 3

Raw data values used to create "Sweet Spot" selection for reduced lignin alfalfa events represented in FIG. 2.

| Graph Id | Event | Mean vigor | Mean ADL | % Null ADL | Mean NDFD | % Null NDFD | Mean G | % Null G |
|---|---|---|---|---|---|---|---|---|
| 1 | JJ255-3 | 7.0 | 10.3 | 104% | 23.7 | 81% | 3.6 | 110% |
| 2 | KK010-3 | 10.0 | 10.4 | 105% | 24.2 | 83% | 3.6 | 110% |
| 3 | KK038-1 | 8.0 | 9.9 | 100% | 24.5 | 84% | 3.2 | 97% |
| 4 | JJ195-2 | 8.0 | 10.2 | 103% | 24.5 | 84% | 3.7 | 112% |
| 5 | JJ234-2 | 8.0 | 10.9 | 110% | 24.6 | 84% | 3.8 | 115% |
| 6 | KK189-3 | 9.0 | 11.3 | 114% | 24.7 | 84% | 3.9 | 119% |
| 7 | KK004-2 | 8.0 | 9.9 | 100% | 24.9 | 85% | 3.2 | 96% |
| 8 | KK189-3 | 9.0 | 10.3 | 104% | 25.0 | 86% | 3.7 | 112% |
| 9 | KK155-3 | 5.0 | 10.4 | 105% | 25.2 | 86% | 3.6 | 108% |

TABLE 3-continued

Raw data values used to create "Sweet Spot" selection for reduced lignin alfalfa events represented in FIG. 2.

| Graph Id | Event | Mean vigor | Mean ADL | % Null ADL | Mean NDFD | % Null NDFD | Mean G | % Null G |
|---|---|---|---|---|---|---|---|---|
| 10 | KK038-1 | 8.0 | 9.4 | 95% | 25.2 | 86% | 3.0 | 90% |
| 11 | KK010-3 | 7.0 | 9.8 | 98% | 25.3 | 87% | 3.4 | 103% |
| 12 | JJ195-2 | 7.0 | 10.2 | 103% | 25.4 | 87% | 3.5 | 106% |
| 13 | KK296-1 | 9.0 | 10.0 | 101% | 25.4 | 87% | 3.4 | 103% |
| 14 | KK038-1 | 8.0 | 9.8 | 99% | 25.5 | 87% | 3.3 | 101% |
| 15 | KK019-2 | 8.0 | 9.7 | 98% | 25.6 | 88% | 3.0 | 90% |
| 16 | KK010-2 | 9.0 | 10.3 | 104% | 25.7 | 88% | 3.6 | 108% |
| 17 | KK306-2 | 7.0 | 10.4 | 106% | 25.8 | 88% | 3.7 | 111% |
| 18 | KK189-3 | 9.0 | 10.6 | 108% | 25.9 | 89% | 3.9 | 118% |
| 19 | KK038-1 | 8.0 | 10.0 | 101% | 26.0 | 89% | 2.9 | 89% |
| 20 | JJ054-3 | 7.0 | 10.3 | 104% | 26.0 | 89% | 3.5 | 105% |
| 21 | KK010-2 | 8.0 | 10.0 | 101% | 26.2 | 90% | 2.8 | 84% |
| 22 | KK010-3 | 7.0 | 10.1 | 102% | 26.2 | 90% | 3.1 | 93% |
| 23 | KK019-3 | 9.0 | 10.7 | 108% | 26.3 | 90% | 3.6 | 109% |
| 24 | JJ134-2 | 7.0 | 9.5 | 96% | 26.4 | 90% | 2.7 | 82% |
| 25 | KK416-2 | 8.0 | 10.5 | 106% | 26.4 | 90% | 3.5 | 107% |
| 26 | KK155-3 | 8.0 | 9.7 | 98% | 26.5 | 91% | 3.0 | 90% |
| 27 | JJ173-1 | 6.0 | 10.4 | 105% | 26.6 | 91% | 3.0 | 92% |
| 28 | JJ173-1 | 8.0 | 10.2 | 103% | 26.6 | 91% | 3.5 | 106% |
| 29 | KK417-3 | 8.0 | 11.4 | 116% | 26.6 | 91% | 3.5 | 107% |
| 30 | KK417-3 | 8.0 | 10.4 | 105% | 26.7 | 91% | 3.3 | 100% |
| 31 | KK416-2 | 7.0 | 9.7 | 98% | 26.8 | 92% | 2.8 | 85% |
| 32 | KK010-1 | 6.0 | 9.9 | 99% | 26.8 | 92% | 2.8 | 85% |
| 33 | JJ198-2 | 8.0 | 10.1 | 102% | 26.8 | 92% | 3.0 | 90% |
| 34 | JJ325-4 | 8.0 | 9.2 | 93% | 26.9 | 92% | 2.9 | 88% |
| 35 | KK216-1 | 8.0 | 9.5 | 96% | 26.9 | 92% | 3.0 | 91% |
| 36 | JJ189-3 | 9.0 | 10.3 | 104% | 27.0 | 92% | 3.2 | 97% |
| 37 | KK417-3 | 8.0 | 10.1 | 102% | 27.3 | 93% | 3.4 | 102% |
| 38 | KK019-3 | 8.0 | 10.0 | 101% | 27.3 | 93% | 3.4 | 104% |
| 39 | JJ173-2 | 10.0 | 10.2 | 103% | 27.4 | 94% | 3.4 | 103% |
| 40 | KK038-3 | 7.0 | 10.7 | 108% | 27.4 | 94% | 3.5 | 107% |
| 41 | JJ173-1 | 7.0 | 10.3 | 104% | 27.4 | 94% | 3.3 | 100% |
| 42 | KK019-3 | 8.0 | 10.5 | 106% | 27.4 | 94% | 3.7 | 111% |
| 43 | JJ173-1 | 8.0 | 10.3 | 104% | 27.5 | 94% | 3.5 | 105% |
| 44 | KK004-3 | 8.0 | 9.9 | 100% | 27.5 | 94% | 3.4 | 103% |
| 45 | KK189-3 | 7.0 | 9.6 | 97% | 27.6 | 94% | 3.0 | 92% |
| 46 | KK155-3 | 8.0 | 10.0 | 101% | 27.6 | 94% | 3.2 | 96% |
| 47 | KK155-3 | 7.0 | 10.2 | 103% | 27.6 | 94% | 3.4 | 103% |
| 48 | JJ255-3 | 8.0 | 9.9 | 100% | 27.6 | 95% | 3.2 | 97% |
| 49 | JJ259-3 | 7.0 | 9.9 | 100% | 27.6 | 95% | 3.2 | 98% |
| 50 | JJ255-3 | 7.0 | 9.9 | 100% | 27.7 | 95% | 3.2 | 97% |
| 51 | JJ109-2 | 7.0 | 10.3 | 104% | 27.7 | 95% | 3.5 | 106% |
| 52 | JJ259-3 | 6.0 | 10.4 | 105% | 27.8 | 95% | 3.3 | 99% |
| 53 | KK308-3 | 10.0 | 10.6 | 107% | 27.8 | 95% | 3.7 | 111% |
| 54 | JJ198-2 | 9.0 | 10.0 | 101% | 27.9 | 95% | 3.2 | 98% |
| 55 | JJ055-2 | 8.0 | 9.9 | 100% | 27.9 | 95% | 3.3 | 101% |
| 56 | JJ173-2 | 8.0 | 10.8 | 109% | 27.9 | 95% | 3.5 | 105% |
| 57 | KK189-3 | 8.0 | 10.7 | 108% | 27.9 | 95% | 3.8 | 116% |
| 58 | KK019-3 | 7.0 | 8.4 | 85% | 27.9 | 96% | 2.6 | 79% |
| 59 | KK010-2 | 9.0 | 10.0 | 101% | 27.9 | 96% | 3.2 | 98% |
| 60 | KK155-3 | 6.0 | 10.0 | 101% | 28.0 | 96% | 3.0 | 92% |
| 61 | JJ109-2 | 7.0 | 9.6 | 97% | 28.0 | 96% | 3.3 | 98% |
| 62 | JJ109-2 | 10.0 | 8.9 | 89% | 28.0 | 96% | 2.7 | 83% |
| 63 | KK189-3 | 6.0 | 10.5 | 106% | 28.0 | 96% | 3.7 | 111% |
| 64 | KK417-3 | 8.0 | 10.8 | 109% | 28.0 | 96% | 3.9 | 117% |
| 65 | KK416-2 | 8.0 | 10.3 | 104% | 28.1 | 96% | 3.3 | 100% |
| 66 | JJ055-3 | 8.0 | 10.1 | 102% | 28.1 | 96% | 3.5 | 107% |
| 67 | JJ109-1 | 8.0 | 10.4 | 105% | 28.1 | 96% | 3.6 | 109% |
| 68 | KK010-1 | 8.0 | 10.6 | 107% | 28.3 | 97% | 3.7 | 113% |
| 69 | KK038-3 | 8.0 | 8.9 | 90% | 28.3 | 97% | 2.3 | 69% |
| 70 | JJ325-4 | 7.0 | 9.7 | 98% | 28.3 | 97% | 3.1 | 93% |
| 71 | JJ173-1 | 7.0 | 9.6 | 97% | 28.4 | 97% | 3.0 | 91% |
| 72 | JJ173-2 | 8.0 | 9.8 | 99% | 28.4 | 97% | 3.2 | 98% |
| 73 | KK155-3 | 6.0 | 9.8 | 99% | 28.4 | 97% | 3.3 | 99% |
| 74 | JJ054-2 | 5.0 | 9.8 | 98% | 28.5 | 97% | 2.8 | 85% |
| 75 | KK155-3 | 8.0 | 9.7 | 98% | 28.5 | 97% | 3.0 | 90% |
| 76 | KK019-3 | 7.0 | 9.9 | 100% | 28.5 | 97% | 3.3 | 99% |
| 77 | JJ041-1 | 8.0 | 8.9 | 90% | 28.5 | 98% | 2.7 | 82% |
| 78 | KK416-2 | 8.0 | 10.2 | 103% | 28.5 | 98% | 3.3 | 100% |
| 79 | JJ255-3 | 8.0 | 10.6 | 107% | 28.5 | 98% | 3.5 | 105% |
| 80 | JJ255-3 | 7.0 | 10.5 | 106% | 28.5 | 98% | 3.6 | 110% |
| 81 | KK155-3 | 9.0 | 9.4 | 95% | 28.6 | 98% | 3.2 | 97% |
| 82 | KK010-3 | 7.0 | 10.2 | 103% | 28.6 | 98% | 3.6 | 109% |

TABLE 3-continued

Raw data values used to create "Sweet Spot" selection for reduced lignin alfalfa events represented in FIG. 2.

| Graph Id | Event | Mean vigor | Mean ADL | % Null ADL | Mean NDFD | % Null NDFD | Mean G | % Null G |
|---|---|---|---|---|---|---|---|---|
| 83 | JJ255-3 | 8.0 | 9.8 | 99% | 28.6 | 98% | 3.3 | 100% |
| 84 | KK189-3 | 7.0 | 10.2 | 103% | 28.6 | 98% | 3.5 | 105% |
| 85 | JJ173-1 | 8.0 | 10.8 | 109% | 28.6 | 98% | 3.7 | 111% |
| 86 | JJ109-2 | 8.0 | 7.5 | 76% | 28.7 | 98% | 2.2 | 67% |
| 87 | JJ041-1 | 8.0 | 8.7 | 88% | 28.7 | 98% | 2.6 | 79% |
| 88 | JJ325-5 | 7.0 | 10.2 | 103% | 28.7 | 98% | 3.2 | 98% |
| 89 | KK189-3 | 8.0 | 10.1 | 102% | 28.7 | 98% | 3.5 | 106% |
| 90 | KK019-2 | 7.0 | 9.9 | 100% | 28.8 | 98% | 3.0 | 91% |
| 91 | KK189-3 | 8.0 | 10.2 | 103% | 28.8 | 98% | 3.5 | 107% |
| 92 | JJ109-1 | 8.0 | 9.9 | 100% | 28.9 | 99% | 3.2 | 97% |
| 93 | KK417-3 | 7.0 | 10.0 | 101% | 28.9 | 99% | 3.5 | 105% |
| 94 | KK216-1 | 7.0 | 9.4 | 95% | 28.9 | 99% | 2.9 | 89% |
| 95 | KK038-1 | 7.0 | 9.2 | 93% | 28.9 | 99% | 2.9 | 89% |
| 96 | JJ325-4 | 7.0 | 9.2 | 93% | 29.0 | 99% | 3.0 | 91% |
| 97 | JJ173-2 | 8.0 | 10.3 | 104% | 29.0 | 99% | 3.6 | 109% |
| 98 | JJ195-2 | 7.0 | 9.8 | 99% | 29.1 | 100% | 3.0 | 91% |
| 99 | KK038-1 | 8.0 | 8.4 | 85% | 29.2 | 100% | 2.6 | 80% |
| 100 | KK019-2 | 8.0 | 9.7 | 98% | 29.2 | 100% | 3.0 | 91% |
| 101 | KK416-2 | 8.0 | 10.4 | 105% | 29.2 | 100% | 3.6 | 110% |
| 102 | KK019-2 | 8.0 | 9.6 | 97% | 29.2 | 100% | 3.1 | 93% |
| 103 | JJ126-3 | 8.0 | 8.0 | 81% | 29.3 | 100% | 2.0 | 60% |
| 104 | JJ325-4 | 7.0 | 10.3 | 104% | 29.3 | 100% | 3.6 | 110% |
| 105 | JJ325-4 | 9.0 | 9.0 | 91% | 29.4 | 101% | 3.0 | 92% |
| 106 | JJ255-3 | 7.0 | 10.0 | 101% | 29.4 | 101% | 3.3 | 99% |
| 107 | JJ259-2 | 5.0 | 9.7 | 98% | 29.4 | 101% | 3.2 | 98% |
| 108 | KK010-2 | 10.0 | 9.9 | 100% | 29.5 | 101% | 3.3 | 100% |
| 109 | JJ173-2 | 7.0 | 10.6 | 107% | 29.5 | 101% | 3.6 | 109% |
| 110 | KK306-2 | 7.0 | 8.6 | 87% | 29.6 | 101% | 2.6 | 78% |
| 111 | JJ259-2 | 7.0 | 9.9 | 100% | 29.6 | 101% | 3.1 | 93% |
| 112 | JJ195-2 | 8.0 | 9.8 | 99% | 29.6 | 101% | 3.3 | 99% |
| 113 | JJ325-5 | 7.0 | 9.4 | 95% | 29.6 | 101% | 2.9 | 88% |
| 114 | KK416-2 | 8.0 | 10.6 | 107% | 29.6 | 101% | 3.5 | 106% |
| 115 | JJ109-3 | 7.0 | 9.7 | 98% | 29.7 | 102% | 3.1 | 94% |
| 116 | JJ255-3 | 7.0 | 9.7 | 98% | 29.7 | 102% | 3.3 | 100% |
| 117 | KK416-2 | 8.0 | 9.9 | 100% | 29.7 | 102% | 3.5 | 105% |
| 118 | JJ325-4 | 9.0 | 9.1 | 92% | 29.7 | 102% | 2.9 | 88% |
| 119 | JJ325-5 | 7.0 | 8.2 | 83% | 29.8 | 102% | 2.5 | 75% |
| 120 | KK010-3 | 8.0 | 9.6 | 97% | 29.8 | 102% | 3.0 | 90% |
| 121 | JJ287-2 | 8.0 | 9.0 | 91% | 29.8 | 102% | 3.0 | 92% |
| 122 | JJ109-1 | 8.0 | 10.1 | 102% | 29.9 | 102% | 3.2 | 98% |
| 123 | KK038-3 | 8.0 | 10.0 | 101% | 29.9 | 102% | 3.5 | 107% |
| 124 | JJ325-5 | 7.0 | 8.8 | 89% | 29.9 | 102% | 2.2 | 67% |
| 125 | JJ198-2 | 7.0 | 9.8 | 99% | 29.9 | 102% | 3.2 | 97% |
| 126 | KK038-3 | 8.0 | 9.7 | 98% | 29.9 | 102% | 3.3 | 100% |
| 127 | KK010-2 | 5.0 | 9.9 | 100% | 30.0 | 103% | 3.1 | 93% |
| 128 | JJ109-3 | 9.0 | 9.7 | 98% | 30.0 | 103% | 3.3 | 99% |
| 129 | KK010-3 | 6.0 | 10.3 | 104% | 30.0 | 103% | 3.7 | 112% |
| 130 | JJ198-2 | 6.0 | 9.2 | 93% | 30.0 | 103% | 2.7 | 83% |
| 131 | JJ255-3 | 8.0 | 10.0 | 101% | 30.0 | 103% | 3.6 | 108% |
| 132 | JJ325-4 | 7.0 | 9.9 | 100% | 30.1 | 103% | 3.2 | 97% |
| 133 | KK019-3 | 8.0 | 10.1 | 103% | 30.1 | 103% | 3.2 | 98% |
| 134 | JJ109-3 | 8.0 | 9.9 | 100% | 30.1 | 103% | 3.2 | 97% |
| 135 | KK014-3 | 8.0 | 8.1 | 82% | 30.2 | 103% | 2.2 | 66% |
| 136 | KK216-1 | 7.0 | 9.6 | 97% | 30.2 | 103% | 3.0 | 92% |
| 137 | JJ198-2 | 7.0 | 10.4 | 105% | 30.2 | 103% | 3.3 | 100% |
| 138 | JJ234-2 | 4.0 | 8.8 | 89% | 30.3 | 104% | 2.2 | 68% |
| 139 | JJ109-1 | 7.0 | 10.5 | 106% | 30.3 | 104% | 3.6 | 108% |
| 140 | KK019-2 | 6.0 | 8.8 | 89% | 30.3 | 104% | 2.4 | 73% |
| 141 | JJ325-5 | 8.0 | 9.5 | 96% | 30.3 | 104% | 3.3 | 99% |
| 142 | KK038-1 | 9.0 | 10.3 | 104% | 30.3 | 104% | 3.5 | 107% |
| 143 | KK155-3 | 7.0 | 10.4 | 105% | 30.3 | 104% | 3.6 | 110% |
| 144 | JJ109-1 | 7.0 | 10.4 | 105% | 30.4 | 104% | 3.7 | 111% |
| 145 | JJ109-2 | 7.0 | 9.6 | 97% | 30.4 | 104% | 2.9 | 89% |
| 146 | KK137-2 | 8.0 | 7.9 | 80% | 30.5 | 104% | 2.3 | 71% |
| 147 | KK416-2 | 6.0 | 9.6 | 97% | 30.5 | 104% | 2.5 | 77% |
| 148 | JJ004-2 | 8.0 | 8.6 | 87% | 30.5 | 104% | 2.8 | 85% |
| 149 | JJ325-4 | 8.0 | 9.5 | 95% | 30.5 | 104% | 2.8 | 86% |
| 150 | JJ271-2 | 8.0 | 8.2 | 83% | 30.6 | 105% | 2.4 | 72% |
| 151 | KK216-1 | 7.0 | 9.5 | 96% | 30.7 | 105% | 3.0 | 90% |
| 152 | JJ234-2 | 8.0 | 9.8 | 99% | 30.7 | 105% | 3.2 | 98% |
| 153 | KK019-3 | 8.0 | 9.9 | 100% | 30.8 | 105% | 3.0 | 92% |
| 154 | JJ195-2 | 7.0 | 9.8 | 99% | 30.8 | 105% | 3.3 | 99% |
| 155 | KK010-2 | 6.0 | 10.1 | 102% | 30.8 | 105% | 3.3 | 100% |
| 156 | JJ173-2 | 7.0 | 10.5 | 106% | 30.8 | 105% | 3.8 | 116% |
| 157 | KK010-1 | 9.0 | 9.1 | 92% | 30.8 | 105% | 2.9 | 88% |
| 158 | KK019-2 | 7.0 | 9.8 | 99% | 30.8 | 105% | 2.9 | 89% |
| 159 | JJ109-3 | 9.0 | 8.2 | 83% | 30.9 | 106% | 2.5 | 76% |
| 160 | KK038-1 | 7.0 | 9.1 | 91% | 30.9 | 106% | 2.7 | 82% |
| 161 | JJ173-1 | 8.0 | 9.9 | 100% | 31.0 | 106% | 3.2 | 96% |
| 162 | JJ031-2 | 10.0 | 8.6 | 87% | 31.1 | 106% | 2.9 | 87% |
| 163 | KK038-3 | 6.0 | 9.6 | 97% | 31.1 | 106% | 3.1 | 93% |
| 164 | JJ325-5 | 7.0 | 9.5 | 96% | 31.2 | 107% | 3.1 | 95% |
| 165 | JJ325-4 | 7.0 | 9.3 | 94% | 31.2 | 107% | 2.9 | 87% |
| 166 | KK416-2 | 6.0 | 9.6 | 97% | 31.2 | 107% | 3.1 | 93% |
| 167 | KK010-2 | 9.0 | 9.7 | 97% | 31.2 | 107% | 3.2 | 96% |
| 168 | JJ325-5 | 7.0 | 9.1 | 92% | 31.3 | 107% | 2.8 | 85% |
| 169 | JJ325-5 | 9.0 | 9.5 | 96% | 31.3 | 107% | 3.0 | 92% |
| 170 | JJ255-3 | 7.0 | 9.3 | 94% | 31.3 | 107% | 3.0 | 92% |
| 171 | KK010-3 | 7.0 | 9.8 | 98% | 31.4 | 107% | 3.3 | 100% |
| 172 | KK179-2 | 9.0 | 7.8 | 79% | 31.4 | 108% | 2.1 | 62% |
| 173 | KK019-3 | 7.0 | 10.2 | 103% | 31.4 | 108% | 3.2 | 98% |
| 174 | JJ031-2 | 7.0 | 8.6 | 87% | 31.5 | 108% | 2.6 | 77% |
| 175 | KK019-2 | 8.0 | 9.4 | 95% | 31.5 | 108% | 3.0 | 92% |
| 176 | KK010-1 | 7.0 | 9.9 | 100% | 31.6 | 108% | 3.1 | 95% |
| 177 | KK038-3 | 8.0 | 8.6 | 87% | 31.6 | 108% | 2.8 | 84% |
| 178 | JJ195-2 | 8.0 | 9.5 | 96% | 31.6 | 108% | 3.0 | 90% |
| 179 | KK010-1 | 7.0 | 9.9 | 100% | 31.6 | 108% | 3.0 | 91% |
| 180 | JJ041-1 | 8.0 | 8.6 | 87% | 31.7 | 108% | 2.3 | 69% |
| 181 | JJ331-5 | 8.0 | 7.9 | 79% | 31.7 | 109% | 2.1 | 62% |
| 182 | JJ325-4 | 8.0 | 9.4 | 95% | 31.7 | 109% | 2.7 | 83% |
| 183 | JJ325-5 | 8.0 | 10.0 | 101% | 31.7 | 109% | 3.3 | 100% |
| 184 | JJ234-2 | 6.0 | 9.2 | 93% | 31.8 | 109% | 3.1 | 93% |
| 185 | KK004-2 | 6.0 | 9.7 | 98% | 31.8 | 109% | 3.2 | 96% |
| 186 | JJ109-3 | 9.0 | 8.1 | 81% | 31.8 | 109% | 2.3 | 69% |
| 187 | JJ109-1 | 8.0 | 8.4 | 85% | 31.8 | 109% | 2.6 | 80% |
| 188 | KK179-2 | 8.0 | 8.0 | 81% | 31.9 | 109% | 2.0 | 62% |
| 189 | JJ173-2 | 6.0 | 9.2 | 93% | 31.9 | 109% | 2.3 | 70% |
| 190 | JJ122-3 | 8.0 | 8.0 | 81% | 31.9 | 109% | 2.4 | 73% |
| 191 | JJ189-3 | 8.0 | 9.1 | 92% | 31.9 | 109% | 3.1 | 95% |
| 192 | KK038-1 | 7.0 | 9.8 | 98% | 32.0 | 109% | 3.0 | 92% |
| 193 | KK019-2 | 8.0 | 9.5 | 95% | 32.0 | 109% | 3.2 | 96% |
| 194 | JJ109-3 | 8.0 | 9.8 | 99% | 32.0 | 109% | 3.5 | 106% |
| 195 | KK004-2 | 7.0 | 8.6 | 87% | 32.0 | 110% | 2.6 | 79% |
| 196 | JJ331-5 | 7.0 | 8.6 | 87% | 32.1 | 110% | 2.3 | 69% |
| 197 | KK010-1 | 8.0 | 9.6 | 97% | 32.1 | 110% | 2.8 | 85% |
| 198 | KK417-3 | 7.0 | 10.2 | 103% | 32.1 | 110% | 3.3 | 101% |
| 199 | JJ325-4 | 6.0 | 9.6 | 97% | 32.2 | 110% | 3.1 | 95% |
| 200 | JJ109-3 | 8.0 | 7.8 | 78% | 32.2 | 110% | 1.9 | 58% |
| 201 | KK014-2 | 9.0 | 8.3 | 84% | 32.2 | 110% | 2.5 | 77% |
| 202 | JJ325-4 | 7.0 | 9.3 | 94% | 32.2 | 110% | 2.8 | 86% |
| 203 | JJ109-3 | 7.0 | 9.5 | 96% | 32.3 | 110% | 2.9 | 87% |
| 204 | KK179-3 | 7.0 | 7.5 | 76% | 32.4 | 111% | 2.0 | 60% |
| 205 | JJ134-3 | 8.0 | 8.1 | 82% | 32.4 | 111% | 1.9 | 59% |
| 206 | JJ134-3 | 8.0 | 7.2 | 73% | 32.5 | 111% | 1.9 | 59% |
| 207 | KK014-3 | 8.0 | 7.5 | 76% | 32.5 | 111% | 2.1 | 64% |
| 208 | JJ134-3 | 9.0 | 8.2 | 83% | 32.6 | 111% | 2.3 | 69% |
| 209 | JJ031-3 | 8.0 | 7.8 | 79% | 32.6 | 111% | 2.3 | 70% |
| 210 | KK038-3 | 8.0 | 8.5 | 86% | 32.6 | 111% | 2.6 | 78% |
| 211 | JJ109-1 | 8.0 | 7.9 | 80% | 32.6 | 112% | 2.2 | 68% |
| 212 | KK410-2 | 8.0 | 8.3 | 84% | 32.7 | 112% | 2.6 | 78% |
| 213 | KK155-3 | 5.0 | 9.3 | 93% | 32.7 | 112% | 2.8 | 85% |
| 214 | KK216-1 | 7.0 | 9.5 | 96% | 32.8 | 112% | 3.2 | 96% |
| 215 | JJ331-5 | 7.0 | 8.0 | 80% | 32.8 | 112% | 2.2 | 68% |
| 216 | KK038-3 | 9.0 | 8.3 | 84% | 32.8 | 112% | 2.3 | 69% |
| 217 | KK306-2 | 7.0 | 8.8 | 89% | 32.8 | 112% | 2.8 | 85% |
| 218 | KK004-3 | 7.0 | 7.8 | 79% | 32.9 | 113% | 2.3 | 68% |
| 219 | KK004-2 | 8.0 | 7.8 | 79% | 33.0 | 113% | 2.1 | 65% |
| 220 | KK004-3 | 7.0 | 7.9 | 79% | 33.0 | 113% | 2.0 | 61% |
| 221 | JJ004-2 | 7.0 | 8.0 | 81% | 33.0 | 113% | 2.4 | 74% |
| 222 | KK014-2 | 7.0 | 7.6 | 77% | 33.1 | 113% | 2.1 | 62% |
| 223 | JJ126-3 | 8.0 | 8.2 | 83% | 33.1 | 113% | 2.1 | 62% |
| 224 | JJ259-3 | 7.0 | 7.8 | 78% | 33.1 | 113% | 2.2 | 65% |
| 225 | KK186-2 | 8.0 | 7.8 | 79% | 33.1 | 113% | 2.2 | 66% |
| 226 | KK014-2 | 9.0 | 8.3 | 83% | 33.1 | 113% | 2.7 | 81% |
| 227 | JJ325-4 | 7.0 | 9.4 | 95% | 33.1 | 113% | 2.8 | 85% |
| 228 | KK136-3 | 10.0 | 7.3 | 74% | 33.2 | 114% | 1.9 | 57% |

TABLE 3-continued

Raw data values used to create "Sweet Spot" selection for reduced lignin alfalfa events represented in FIG. 2.

| Graph Id | Event | Mean vigor | Mean ADL | % Null ADL | Mean NDFD | % Null NDFD | Mean G | % Null G |
|---|---|---|---|---|---|---|---|---|
| 229 | JJ234-2 | 8.0 | 7.6 | 76% | 33.2 | 114% | 2.1 | 63% |
| 230 | JJ109-2 | 9.0 | 7.8 | 79% | 33.2 | 114% | 2.1 | 64% |
| 231 | JJ173-2 | 6.0 | 9.5 | 96% | 33.2 | 114% | 3.0 | 91% |
| 232 | JJ287-3 | 8.0 | 8.3 | 84% | 33.3 | 114% | 2.5 | 76% |
| 233 | JJ031-1 | 8.0 | 8.5 | 86% | 33.3 | 114% | 2.3 | 70% |
| 234 | JJ031-3 | 8.0 | 7.3 | 73% | 33.4 | 114% | 1.6 | 49% |
| 235 | KK533-3 | 6.0 | 7.5 | 76% | 33.4 | 114% | 2.0 | 62% |
| 236 | KK010-2 | 6.0 | 9.4 | 95% | 33.4 | 114% | 3.0 | 90% |
| 237 | JJ004-1 | 7.0 | 8.0 | 81% | 33.5 | 115% | 2.3 | 71% |
| 238 | KK179-3 | 7.0 | 7.4 | 75% | 33.5 | 115% | 2.0 | 59% |
| 239 | JJ031-3 | 9.0 | 7.6 | 76% | 33.5 | 115% | 2.2 | 67% |
| 240 | JJ331-5 | 7.0 | 7.8 | 79% | 33.5 | 115% | 2.3 | 69% |
| 241 | JJ195-2 | 7.0 | 9.4 | 95% | 33.6 | 115% | 2.7 | 81% |
| 242 | JJ031-3 | 7.0 | 7.2 | 72% | 33.7 | 115% | 1.8 | 53% |
| 243 | JJ109-3 | 7.0 | 7.6 | 77% | 33.7 | 115% | 1.9 | 59% |
| 244 | JJ109-2 | 8.0 | 7.1 | 72% | 33.7 | 115% | 2.0 | 61% |
| 245 | JJ271-2 | 7.0 | 8.2 | 83% | 33.7 | 115% | 2.5 | 77% |
| 246 | KK186-1 | 8.0 | 7.4 | 75% | 33.7 | 115% | 1.8 | 56% |
| 247 | KK306-2 | 8.0 | 7.8 | 79% | 33.7 | 115% | 2.1 | 63% |
| 248 | JJ004-2 | 7.0 | 7.8 | 79% | 33.7 | 115% | 2.2 | 68% |
| 249 | JJ126-3 | 9.0 | 7.4 | 75% | 33.7 | 115% | 2.2 | 68% |
| 250 | JJ126-3 | 8.0 | 8.1 | 82% | 33.7 | 115% | 2.5 | 75% |
| 251 | KK038-1 | 7.0 | 8.4 | 85% | 33.7 | 115% | 2.6 | 79% |
| 252 | JJ259-3 | 7.0 | 8.4 | 85% | 33.8 | 116% | 2.4 | 72% |
| 253 | KK038-1 | 5.0 | 8.0 | 80% | 33.8 | 116% | 2.1 | 63% |
| 254 | JJ004-2 | 7.0 | 7.4 | 75% | 33.8 | 116% | 2.2 | 68% |
| 255 | KK136-3 | 6.0 | 7.4 | 75% | 33.9 | 116% | 1.9 | 57% |
| 256 | JJ031-1 | 6.0 | 8.0 | 81% | 33.9 | 116% | 2.3 | 69% |
| 257 | JJ181-3 | 8.0 | 8.1 | 82% | 33.9 | 116% | 2.4 | 73% |
| 258 | KK186-2 | 8.0 | 8.0 | 80% | 34.0 | 116% | 2.0 | 62% |
| 259 | JJ031-2 | 7.0 | 7.8 | 78% | 34.0 | 116% | 2.1 | 63% |
| 260 | KK004-2 | 7.0 | 9.0 | 91% | 34.0 | 116% | 2.6 | 80% |
| 261 | JJ109-1 | 7.0 | 7.7 | 78% | 34.0 | 116% | 2.0 | 62% |
| 262 | KK038-1 | 6.0 | 8.3 | 84% | 34.0 | 116% | 2.3 | 70% |
| 263 | JJ122-2 | 8.0 | 7.1 | 72% | 34.1 | 117% | 2.1 | 64% |
| 264 | JJ271-2 | 10.0 | 7.3 | 73% | 34.1 | 117% | 2.1 | 64% |
| 265 | JJ122-2 | 6.0 | 7.4 | 75% | 34.1 | 117% | 1.5 | 45% |
| 266 | JJ271-2 | 7.0 | 8.7 | 87% | 34.1 | 117% | 2.2 | 67% |
| 267 | JJ122-2 | 10.0 | 8.0 | 81% | 34.1 | 117% | 2.5 | 76% |
| 268 | JJ134-2 | 8.0 | 7.8 | 78% | 34.2 | 117% | 2.0 | 60% |
| 269 | KK480-3 | 7.0 | 7.1 | 72% | 34.2 | 117% | 2.1 | 65% |
| 270 | JJ004-2 | 8.0 | 7.9 | 79% | 34.2 | 117% | 2.2 | 66% |
| 271 | JJ259-2 | 8.0 | 8.2 | 83% | 34.2 | 117% | 2.4 | 72% |
| 272 | KK533-1 | 7.0 | 8.4 | 85% | 34.3 | 117% | 2.3 | 70% |
| 273 | KK038-3 | 6.0 | 8.6 | 87% | 34.3 | 117% | 2.0 | 62% |
| 274 | JJ134-3 | 8.0 | 7.7 | 78% | 34.3 | 117% | 2.1 | 64% |
| 275 | KK179-2 | 7.0 | 7.9 | 80% | 34.3 | 117% | 2.5 | 76% |
| 276 | JJ259-3 | 7.0 | 7.1 | 71% | 34.4 | 118% | 1.6 | 49% |
| 277 | JJ004-1 | 7.0 | 7.6 | 76% | 34.4 | 118% | 1.9 | 58% |
| 278 | KK533-2 | 7.0 | 8.1 | 82% | 34.4 | 118% | 2.2 | 65% |
| 279 | JJ234-2 | 7.0 | 7.1 | 72% | 34.4 | 118% | 1.8 | 55% |
| 280 | JJ258-3 | 7.0 | 7.8 | 79% | 34.4 | 118% | 2.2 | 66% |
| 281 | JJ331-5 | 7.0 | 8.1 | 81% | 34.4 | 118% | 2.3 | 71% |
| 282 | JJ122-3 | 7.0 | 7.4 | 75% | 34.5 | 118% | 2.0 | 60% |
| 283 | JJ331-5 | 9.0 | 7.6 | 77% | 34.5 | 118% | 2.3 | 69% |
| 284 | KK014-2 | 7.0 | 7.6 | 77% | 34.5 | 118% | 2.0 | 62% |
| 285 | KK136-2 | 7.0 | 7.2 | 73% | 34.6 | 118% | 2.0 | 59% |
| 286 | JJ031-3 | 7.0 | 7.5 | 76% | 34.6 | 118% | 2.1 | 63% |
| 287 | JJ109-2 | 8.0 | 8.1 | 81% | 34.6 | 118% | 2.1 | 64% |
| 288 | JJ331-5 | 7.0 | 8.8 | 89% | 34.6 | 118% | 2.5 | 75% |
| 289 | JJ109-3 | 7.0 | 7.6 | 77% | 34.6 | 118% | 1.8 | 53% |
| 290 | JJ271-1 | 8.0 | 7.4 | 75% | 34.6 | 118% | 2.1 | 63% |
| 291 | JJ031-2 | 7.0 | 8.0 | 81% | 34.6 | 118% | 2.2 | 66% |
| 292 | KK038-2 | 6.0 | 8.3 | 84% | 34.6 | 118% | 2.4 | 72% |
| 293 | JJ031-1 | 9.0 | 7.1 | 71% | 34.7 | 119% | 1.6 | 49% |
| 294 | JJ234-2 | 6.0 | 7.8 | 79% | 34.7 | 119% | 2.0 | 59% |
| 295 | KK306-2 | 7.0 | 7.8 | 78% | 34.7 | 119% | 2.2 | 67% |
| 296 | KK199-2 | 7.0 | 7.8 | 79% | 34.7 | 119% | 2.3 | 71% |
| 297 | JJ031-3 | 8.0 | 7.6 | 77% | 34.8 | 119% | 2.1 | 65% |
| 298 | JJ106-1 | 9.0 | 7.9 | 80% | 34.8 | 119% | 2.2 | 68% |
| 299 | KK014-2 | 9.0 | 8.2 | 83% | 34.8 | 119% | 2.4 | 73% |
| 300 | JJ109-2 | 8.0 | 8.3 | 83% | 34.8 | 119% | 2.6 | 78% |
| 301 | JJ004-1 | 7.0 | 7.6 | 76% | 34.9 | 119% | 1.9 | 58% |
| 302 | JJ109-1 | 10.0 | 7.8 | 79% | 35.0 | 120% | 2.1 | 63% |
| 303 | KK106-1 | 7.0 | 7.2 | 73% | 35.0 | 120% | 1.8 | 55% |
| 304 | KK179-3 | 7.0 | 6.9 | 70% | 35.0 | 120% | 1.8 | 56% |
| 305 | JJ259-3 | 8.0 | 7.4 | 75% | 35.0 | 120% | 1.8 | 56% |
| 306 | JJ109-2 | 10.0 | 7.8 | 79% | 35.0 | 120% | 2.2 | 67% |
| 307 | JJ031-2 | 6.0 | 7.9 | 80% | 35.0 | 120% | 2.2 | 67% |
| 308 | KK038-1 | 8.0 | 8.6 | 86% | 35.0 | 120% | 2.3 | 71% |
| 309 | JJ271-1 | 8.0 | 7.2 | 73% | 35.1 | 120% | 1.7 | 52% |
| 310 | JJ234-2 | 7.0 | 7.4 | 74% | 35.1 | 120% | 1.9 | 57% |
| 311 | JJ004-1 | 8.0 | 8.0 | 81% | 35.1 | 120% | 1.8 | 54% |
| 312 | JJ122-2 | 8.0 | 6.9 | 70% | 35.1 | 120% | 1.9 | 58% |
| 313 | JJ331-5 | 7.0 | 8.4 | 85% | 35.1 | 120% | 2.3 | 70% |
| 314 | JJ109-3 | 8.0 | 7.7 | 78% | 35.1 | 120% | 2.4 | 71% |
| 315 | JJ041-1 | 7.0 | 8.3 | 84% | 35.1 | 120% | 2.4 | 72% |
| 316 | KK004-3 | 7.0 | 8.1 | 82% | 35.1 | 120% | 2.5 | 74% |
| 317 | JJ259-2 | 5.0 | 7.2 | 73% | 35.2 | 120% | 1.5 | 45% |
| 318 | JJ031-1 | 6.0 | 7.4 | 74% | 35.2 | 120% | 1.8 | 55% |
| 319 | JJ234-2 | 6.0 | 7.8 | 79% | 35.2 | 120% | 2.1 | 62% |
| 320 | JJ266-3 | 7.0 | 7.9 | 80% | 35.2 | 120% | 2.3 | 70% |
| 321 | JJ331-5 | 7.0 | 8.1 | 82% | 35.3 | 121% | 2.1 | 65% |
| 322 | KK014-2 | 8.0 | 8.0 | 80% | 35.3 | 121% | 2.5 | 76% |
| 323 | JJ122-3 | 8.0 | 7.3 | 74% | 35.3 | 121% | 1.7 | 51% |
| 324 | JJ134-2 | 9.0 | 7.8 | 78% | 35.3 | 121% | 2.0 | 60% |
| 325 | JJ234-2 | 7.0 | 7.4 | 75% | 35.3 | 121% | 2.1 | 63% |
| 326 | KK014-2 | 7.0 | 7.1 | 72% | 35.4 | 121% | 2.0 | 60% |
| 327 | JJ126-3 | 6.0 | 7.8 | 79% | 35.4 | 121% | 2.3 | 68% |
| 328 | JJ242-1 | 7.0 | 7.4 | 75% | 35.4 | 121% | 1.8 | 56% |
| 329 | KK014-2 | 6.0 | 7.5 | 76% | 35.4 | 121% | 2.1 | 65% |
| 330 | KK106-3 | 9.0 | 7.9 | 79% | 35.4 | 121% | 2.3 | 70% |
| 331 | KK533-3 | 8.0 | 7.0 | 71% | 35.5 | 121% | 1.6 | 47% |
| 332 | KK004-3 | 5.0 | 7.8 | 79% | 35.5 | 121% | 2.1 | 63% |
| 333 | JJ109-3 | 8.0 | 7.7 | 78% | 35.5 | 122% | 1.9 | 58% |
| 334 | KK533-3 | 7.0 | 7.7 | 78% | 35.5 | 122% | 2.0 | 59% |
| 335 | KK136-3 | 5.0 | 7.6 | 76% | 35.5 | 122% | 2.0 | 60% |
| 336 | JJ109-1 | 8.0 | 7.8 | 78% | 35.5 | 122% | 2.3 | 70% |
| 337 | JJ173-2 | 7.0 | 9.4 | 94% | 35.5 | 122% | 3.4 | 103% |
| 338 | JJ122-2 | 6.0 | 7.4 | 74% | 35.6 | 122% | 1.7 | 51% |
| 339 | JJ298-3 | 9.0 | 7.4 | 75% | 35.6 | 122% | 1.8 | 54% |
| 340 | JJ031-3 | 7.0 | 7.6 | 77% | 35.6 | 122% | 1.9 | 57% |
| 341 | KK179-3 | 9.0 | 8.0 | 81% | 35.6 | 122% | 2.4 | 73% |
| 342 | JJ134-2 | 6.0 | 7.2 | 73% | 35.6 | 122% | 1.6 | 49% |
| 343 | JJ271-1 | 6.0 | 7.1 | 71% | 35.6 | 122% | 1.7 | 51% |
| 344 | KK410-3 | 9.0 | 7.3 | 73% | 35.6 | 122% | 1.9 | 58% |
| 345 | JJ242-1 | 6.0 | 7.4 | 75% | 35.7 | 122% | 1.8 | 55% |
| 346 | JJ181-3 | 8.0 | 7.3 | 73% | 35.7 | 122% | 2.0 | 60% |
| 347 | JJ031-2 | 7.0 | 7.9 | 79% | 35.7 | 122% | 2.1 | 65% |
| 348 | JJ259-2 | 7.0 | 7.6 | 77% | 35.7 | 122% | 2.3 | 69% |
| 349 | KK136-3 | 7.0 | 7.9 | 80% | 35.7 | 122% | 2.3 | 70% |
| 350 | JJ004-1 | 6.0 | 7.1 | 72% | 35.7 | 122% | 1.6 | 49% |
| 351 | KK306-2 | 7.0 | 7.3 | 74% | 35.7 | 122% | 2.0 | 62% |
| 352 | JJ126-3 | 6.0 | 7.1 | 72% | 35.8 | 123% | 1.7 | 51% |
| 353 | JJ234-2 | 7.0 | 7.8 | 79% | 35.8 | 123% | 2.0 | 60% |
| 354 | JJ109-1 | 8.0 | 8.0 | 80% | 35.8 | 123% | 2.5 | 77% |
| 355 | JJ173-1 | 7.0 | 9.5 | 96% | 35.8 | 123% | 3.1 | 93% |
| 356 | JJ181-3 | 7.0 | 7.7 | 77% | 35.9 | 123% | 2.1 | 63% |
| 357 | KK106-3 | 7.0 | 8.1 | 82% | 35.9 | 123% | 2.2 | 65% |
| 358 | JJ122-2 | 8.0 | 7.1 | 72% | 36.0 | 123% | 2.0 | 59% |
| 359 | KK306-2 | 7.0 | 7.5 | 75% | 36.0 | 123% | 1.9 | 56% |
| 360 | JJ259-3 | 6.0 | 7.4 | 75% | 36.0 | 123% | 1.9 | 59% |
| 361 | JJ271-1 | 7.0 | 7.3 | 74% | 36.1 | 123% | 2.1 | 63% |
| 362 | JJ266-3 | 7.0 | 7.7 | 78% | 36.1 | 123% | 2.2 | 68% |
| 363 | JJ122-1 | 8.0 | 8.4 | 85% | 36.1 | 124% | 2.3 | 69% |
| 364 | JJ126-3 | 8.0 | 7.5 | 75% | 36.1 | 124% | 2.3 | 71% |
| 365 | JJ126-3 | 8.0 | 7.6 | 77% | 36.2 | 124% | 1.8 | 55% |
| 366 | JJ031-3 | 7.0 | 7.2 | 73% | 36.2 | 124% | 2.1 | 64% |
| 367 | JJ122-2 | 10.0 | 7.7 | 78% | 36.3 | 124% | 2.2 | 66% |
| 368 | KK199-2 | 7.0 | 8.1 | 82% | 36.3 | 124% | 2.4 | 72% |
| 369 | JJ004-1 | 6.0 | 7.9 | 80% | 36.3 | 124% | 1.7 | 51% |
| 370 | JJ271-2 | 7.0 | 7.6 | 77% | 36.3 | 124% | 2.0 | 60% |
| 371 | JJ242-1 | 7.0 | 7.2 | 73% | 36.4 | 124% | 1.7 | 51% |
| 372 | KK306-2 | 7.0 | 7.3 | 74% | 36.4 | 124% | 1.8 | 54% |
| 373 | KK533-3 | 8.0 | 7.2 | 73% | 36.4 | 125% | 2.1 | 64% |
| 374 | KK179-3 | 8.0 | 8.2 | 83% | 36.4 | 125% | 2.4 | 73% |

TABLE 3-continued

Raw data values used to create "Sweet Spot" selection for reduced lignin alfalfa events represented in FIG. 2.

| Graph Id | Event | Mean vigor | Mean ADL | % Null ADL | Mean NDFD | % Null NDFD | Mean G | % Null G |
|---|---|---|---|---|---|---|---|---|
| 375 | JJ031-2 | 9.0 | 8.3 | 84% | 36.5 | 125% | 2.9 | 87% |
| 376 | KK179-2 | 9.0 | 7.7 | 78% | 36.6 | 125% | 2.1 | 64% |
| 377 | KK014-2 | 8.0 | 7.7 | 78% | 36.6 | 125% | 2.3 | 69% |
| 378 | KK106-3 | 8.0 | 8.3 | 84% | 36.6 | 125% | 2.5 | 76% |
| 379 | JJ298-1 | 7.0 | 7.2 | 72% | 36.6 | 125% | 1.7 | 51% |
| 380 | JJ122-1 | 8.0 | 7.2 | 73% | 36.6 | 125% | 1.9 | 59% |
| 381 | JJ271-2 | 7.0 | 7.7 | 78% | 36.6 | 125% | 2.0 | 59% |
| 382 | JJ126-3 | 8.0 | 8.0 | 80% | 36.6 | 125% | 2.1 | 65% |
| 383 | KK533-2 | 7.0 | 6.9 | 69% | 36.7 | 126% | 1.7 | 51% |
| 384 | KK480-3 | 6.0 | 7.3 | 73% | 36.7 | 126% | 1.9 | 58% |
| 385 | KK306-2 | 8.0 | 7.0 | 70% | 36.7 | 126% | 2.1 | 63% |
| 386 | JJ271-2 | 7.0 | 8.1 | 82% | 36.7 | 126% | 2.5 | 77% |
| 387 | JJ031-3 | 7.0 | 8.0 | 81% | 36.7 | 126% | 2.1 | 63% |
| 388 | JJ234-2 | 3.0 | 8.0 | 81% | 36.7 | 126% | 2.8 | 86% |
| 389 | JJ134-3 | 8.0 | 7.6 | 76% | 36.8 | 126% | 1.9 | 57% |
| 390 | KK480-3 | 8.0 | 7.4 | 75% | 36.8 | 126% | 1.9 | 58% |
| 391 | JJ109-1 | 8.0 | 7.4 | 75% | 36.8 | 126% | 2.2 | 66% |
| 392 | JJ122-2 | 8.0 | 8.4 | 85% | 36.8 | 126% | 2.4 | 71% |
| 393 | KK306-2 | 6.0 | 7.1 | 71% | 36.9 | 126% | 1.6 | 47% |
| 394 | JJ004-2 | 7.0 | 7.6 | 76% | 36.9 | 126% | 1.7 | 51% |
| 395 | KK038-3 | 7.0 | 8.1 | 81% | 36.9 | 126% | 2.2 | 66% |
| 396 | KK480-3 | 5.0 | 7.1 | 71% | 36.9 | 126% | 1.3 | 41% |
| 397 | JJ122-2 | 6.0 | 8.1 | 81% | 36.9 | 126% | 2.1 | 63% |
| 398 | KK533-2 | 9.0 | 7.3 | 74% | 36.9 | 126% | 2.2 | 66% |
| 399 | KK136-2 | 7.0 | 7.0 | 70% | 37.0 | 127% | 1.5 | 46% |
| 400 | KK136-2 | 7.0 | 7.1 | 72% | 37.0 | 127% | 1.9 | 58% |
| 401 | JJ298-1 | 5.0 | 7.3 | 74% | 37.0 | 127% | 1.9 | 58% |
| 402 | JJ004-1 | 8.0 | 7.3 | 73% | 37.0 | 127% | 2.1 | 64% |
| 403 | KK004-2 | 8.0 | 8.0 | 81% | 37.0 | 127% | 2.6 | 78% |
| 404 | KK410-3 | 7.0 | 7.0 | 71% | 37.0 | 127% | 1.8 | 55% |
| 405 | JJ126-3 | 10.0 | 7.2 | 73% | 37.0 | 127% | 2.0 | 60% |
| 406 | JJ259-3 | 6.0 | 7.8 | 79% | 37.1 | 127% | 1.9 | 59% |
| 407 | JJ259-2 | 7.0 | 7.4 | 75% | 37.1 | 127% | 2.0 | 59% |
| 408 | JJ004-2 | 8.0 | 7.8 | 79% | 37.1 | 127% | 2.2 | 67% |
| 409 | KK179-3 | 5.0 | 6.6 | 66% | 37.1 | 127% | 1.8 | 55% |
| 410 | KK136-2 | 6.0 | 7.4 | 75% | 37.1 | 127% | 1.9 | 58% |
| 411 | JJ181-3 | 8.0 | 8.0 | 81% | 37.2 | 127% | 2.3 | 68% |
| 412 | KK106-1 | 7.0 | 7.0 | 71% | 37.2 | 127% | 1.8 | 54% |
| 413 | JJ031-1 | 8.0 | 8.0 | 80% | 37.2 | 127% | 2.3 | 70% |
| 414 | KK136-2 | 6.0 | 7.4 | 75% | 37.3 | 128% | 1.7 | 53% |
| 415 | KK253-1 | 7.0 | 7.5 | 76% | 37.3 | 128% | 1.6 | 49% |
| 416 | JJ266-3 | 7.0 | 7.8 | 79% | 37.3 | 128% | 1.6 | 49% |
| 417 | KK014-2 | 5.0 | 6.8 | 69% | 37.4 | 128% | 1.5 | 44% |
| 418 | KK014-2 | 7.0 | 7.1 | 72% | 37.4 | 128% | 1.3 | 40% |
| 419 | JJ242-1 | 9.0 | 7.6 | 76% | 37.4 | 128% | 2.1 | 64% |
| 420 | KK186-2 | 7.0 | 7.1 | 72% | 37.5 | 128% | 1.9 | 58% |
| 421 | JJ031-2 | 6.0 | 7.3 | 74% | 37.5 | 128% | 1.7 | 50% |
| 422 | JJ266-3 | 10.0 | 6.9 | 69% | 37.5 | 128% | 1.7 | 53% |
| 423 | JJ266-3 | 7.0 | 7.0 | 71% | 37.5 | 128% | 1.8 | 54% |
| 424 | JJ031-3 | 6.0 | 6.9 | 70% | 37.5 | 128% | 1.8 | 55% |
| 425 | JJ109-1 | 8.0 | 7.6 | 77% | 37.5 | 128% | 2.1 | 63% |
| 426 | JJ004-2 | 8.0 | 7.5 | 75% | 37.5 | 128% | 2.2 | 66% |
| 427 | JJ122-1 | 6.0 | 7.8 | 78% | 37.5 | 128% | 2.2 | 67% |
| 428 | JJ181-3 | 6.0 | 7.6 | 77% | 37.6 | 129% | 1.9 | 57% |
| 429 | JJ031-2 | 7.0 | 7.5 | 76% | 37.6 | 129% | 2.1 | 62% |
| 430 | KK136-2 | 7.0 | 7.2 | 73% | 37.7 | 129% | 1.6 | 48% |
| 431 | KK136-2 | 9.0 | 6.8 | 68% | 37.7 | 129% | 1.8 | 56% |
| 432 | KK306-2 | 8.0 | 7.1 | 72% | 37.7 | 129% | 2.1 | 63% |
| 433 | JJ271-1 | 5.0 | 6.4 | 65% | 37.8 | 129% | 1.3 | 41% |
| 434 | JJ259-2 | 6.0 | 8.0 | 81% | 37.8 | 129% | 2.5 | 75% |
| 435 | KK136-2 | 6.0 | 7.4 | 75% | 37.8 | 129% | 1.6 | 48% |
| 436 | JJ031-1 | 5.0 | 7.6 | 76% | 37.8 | 129% | 1.8 | 54% |
| 437 | JJ122-2 | 9.0 | 7.2 | 73% | 37.8 | 129% | 2.0 | 60% |
| 438 | JJ259-2 | 7.0 | 6.9 | 69% | 37.9 | 130% | 0.9 | 26% |
| 439 | KK136-3 | 5.0 | 7.4 | 75% | 38.0 | 130% | 1.7 | 52% |
| 440 | KK179-2 | 8.0 | 7.8 | 78% | 38.0 | 130% | 2.3 | 70% |
| 441 | JJ271-1 | 8.0 | 7.4 | 74% | 38.1 | 130% | 1.6 | 50% |
| 442 | JJ298-1 | 9.0 | 6.5 | 65% | 38.1 | 130% | 1.7 | 51% |
| 443 | JJ198-1 | 7.0 | 7.6 | 77% | 38.1 | 130% | 1.6 | 48% |
| 444 | KK106-3 | 7.0 | 7.0 | 70% | 38.1 | 130% | 1.6 | 49% |
| 445 | KK014-2 | 7.0 | 7.9 | 80% | 38.2 | 131% | 2.2 | 67% |
| 446 | KK480-3 | 6.0 | 7.3 | 74% | 38.3 | 131% | 1.6 | 48% |
| 447 | KK106-1 | 8.0 | 7.7 | 78% | 38.3 | 131% | 2.3 | 69% |
| 448 | JJ122-3 | 6.0 | 6.6 | 67% | 38.3 | 131% | 1.5 | 44% |
| 449 | JJ004-2 | 7.0 | 7.6 | 77% | 38.3 | 131% | 2.0 | 60% |
| 450 | JJ271-1 | 5.0 | 7.3 | 74% | 38.4 | 131% | 1.4 | 43% |
| 451 | KK136-2 | 6.0 | 7.1 | 72% | 38.4 | 131% | 2.0 | 62% |
| 452 | KK306-2 | 7.0 | 6.6 | 66% | 38.4 | 132% | 1.6 | 47% |
| 453 | JJ122-3 | 7.0 | 7.0 | 71% | 38.5 | 132% | 1.5 | 47% |
| 454 | KK186-1 | 5.0 | 7.0 | 71% | 38.5 | 132% | 1.7 | 52% |
| 455 | KK179-3 | 8.0 | 7.7 | 78% | 38.5 | 132% | 2.5 | 75% |
| 456 | JJ266-3 | 7.0 | 7.7 | 78% | 38.6 | 132% | 2.4 | 74% |
| 457 | JJ031-1 | 6.0 | 7.3 | 74% | 38.7 | 132% | 1.4 | 44% |
| 458 | JJ266-3 | 6.0 | 6.9 | 69% | 38.7 | 132% | 1.7 | 52% |
| 459 | JJ004-2 | 5.0 | 6.0 | 61% | 38.7 | 133% | 1.0 | 31% |
| 460 | KK480-3 | 7.0 | 6.6 | 67% | 38.7 | 133% | 1.6 | 50% |
| 461 | JJ031-2 | 7.0 | 7.5 | 75% | 38.7 | 133% | 1.7 | 53% |
| 462 | JJ126-3 | 7.0 | 6.8 | 68% | 38.8 | 133% | 1.8 | 53% |
| 463 | KK179-2 | 6.0 | 7.4 | 74% | 38.8 | 133% | 1.8 | 54% |
| 464 | KK136-3 | 7.0 | 7.7 | 77% | 38.9 | 133% | 1.9 | 57% |
| 465 | KK136-2 | 6.0 | 6.2 | 63% | 39.0 | 133% | 1.3 | 41% |
| 466 | JJ259-2 | 6.0 | 7.4 | 75% | 39.0 | 133% | 1.7 | 50% |
| 467 | KK106-3 | 6.0 | 7.0 | 71% | 39.0 | 133% | 1.8 | 55% |
| 468 | KK253-1 | 7.0 | 7.2 | 72% | 39.0 | 133% | 1.8 | 55% |
| 469 | KK306-2 | 7.0 | 7.6 | 76% | 39.1 | 134% | 2.1 | 62% |
| 470 | KK004-3 | 7.0 | 7.6 | 77% | 39.1 | 134% | 2.1 | 63% |
| 471 | KK480-3 | 7.0 | 7.1 | 71% | 39.2 | 134% | 1.6 | 50% |
| 472 | JJ126-3 | 8.0 | 7.5 | 76% | 39.2 | 134% | 1.9 | 58% |
| 473 | KK306-2 | 6.0 | 6.6 | 67% | 39.2 | 134% | 1.5 | 45% |
| 474 | KK480-3 | 8.0 | 7.5 | 76% | 39.2 | 134% | 2.0 | 60% |
| 475 | JJ242-1 | 7.0 | 6.9 | 69% | 39.4 | 135% | 1.4 | 41% |
| 476 | JJ122-2 | 8.0 | 7.2 | 73% | 39.4 | 135% | 2.1 | 63% |
| 477 | KK533-2 | 7.0 | 6.6 | 67% | 39.5 | 135% | 1.6 | 50% |
| 478 | JJ122-2 | 7.0 | 7.3 | 74% | 39.5 | 135% | 1.8 | 54% |
| 479 | JJ122-2 | 7.0 | 6.7 | 68% | 39.5 | 135% | 1.8 | 55% |
| 480 | KK136-2 | 5.0 | 7.3 | 74% | 39.6 | 135% | 1.5 | 45% |
| 481 | KK136-3 | 7.0 | 7.0 | 71% | 39.7 | 136% | 1.8 | 56% |
| 482 | KK533-2 | 7.0 | 7.8 | 79% | 39.7 | 136% | 1.9 | 58% |
| 483 | KK106-3 | 8.0 | 7.2 | 72% | 39.7 | 136% | 2.0 | 60% |
| 484 | KK533-2 | 7.0 | 7.2 | 73% | 39.9 | 136% | 2.0 | 61% |
| 485 | KK533-2 | 6.0 | 7.1 | 72% | 40.0 | 137% | 1.5 | 44% |
| 486 | KK306-2 | 7.0 | 7.1 | 72% | 40.0 | 137% | 2.0 | 60% |
| 487 | JJ259-3 | 6.0 | 6.9 | 70% | 40.2 | 138% | 1.5 | 45% |
| 488 | JJ242-1 | 8.0 | 7.2 | 73% | 40.2 | 138% | 1.6 | 49% |
| 489 | JJ109-2 | 8.0 | 7.8 | 79% | 40.3 | 138% | 2.3 | 70% |
| 490 | JJ271-1 | 8.0 | 7.6 | 77% | 40.3 | 138% | 2.1 | 65% |
| 491 | JJ331-5 | 5.0 | 6.9 | 70% | 40.4 | 138% | 1.7 | 52% |
| 492 | KK004-2 | 7.0 | 7.0 | 71% | 40.5 | 139% | 1.6 | 49% |
| 493 | KK179-2 | 6.0 | 7.1 | 72% | 40.5 | 139% | 1.8 | 54% |
| 494 | JJ122-3 | 7.0 | 7.1 | 72% | 40.7 | 139% | 1.7 | 53% |
| 495 | KK136-3 | 6.0 | 7.4 | 75% | 40.9 | 140% | 1.9 | 57% |
| 496 | KK306-2 | 8.0 | 6.6 | 67% | 41.0 | 140% | 1.7 | 51% |
| 497 | KK306-2 | 8.0 | 6.9 | 70% | 41.1 | 141% | 1.2 | 38% |
| 498 | JJ259-2 | 6.0 | 7.3 | 74% | 41.3 | 141% | 1.7 | 53% |
| 499 | KK306-2 | 7.0 | 7.0 | 70% | 42.0 | 144% | 1.8 | 56% |
| 500 | KK186-1 | 5.0 | 7.2 | 72% | 42.6 | 146% | 1.8 | 54% |
| 525 | Nulls | 7.3 | 9.9 | 100% | 29.2 | 100% | 3.3 | 100% |

Example 5

Data Quality for ADL, NDFD, and Yield Results

Data quality checks were performed prior to analysis using linear models, and outlying plots with large deleted-Studentized residuals were identified. Two passes of this method were used, in order to detect subtler outliers in the second pass that might be hidden by larger outliers removed in the first pass. Outliers identified by this method were removed from the analysis of quality traits. For the analysis of yield, plots with CV of 25% or greater were removed from the analysis. The analysis of response variables was completed using standard analysis of variance models with a mixture of fixed and random effects. The actual statistical calculations were performed using SAS/STAT software Version 9.1.3. Analysis of Variance calculations were performed using PROC MIXED. The model treated constructs and events within constructs as fixed effects, while locations, reps within locations, and location by construct interactions were treated as random effects. Other attributes of the events being tested involved fall dormant or non dormant germplasm (FD, ND). These were all treated as fixed effects. In the cross-year analysis, year was treated as a random effect. Varying numbers of harvest cuts were made at different locations in different years. The yield was analyzed for each cut at each location. In the cross-location, cross-generation, and cross-year analyses, the yield was summed over cuts to obtain a total yield for each plot. The experimental design included matched negative segregants for some events, as well as a pooled null segregant. This allowed two analyses to be performed: in the first analysis, all events were compared to the pooled null segregant, while in the second analysis, events were compared to their matched negative segregants.

Example 6

ADL Measurements in the Lower Stem of Reduced Lignin Alfalfa Events

TABLE 4

Lower stem ADL measurements for the 6 reduced lignin alfalfa events in two fall dormant (FD) germplasms from 3 locations in 2008. Event positive plants showed a significant (p ≤ 0.05) decrease in lower stem ADL, which ranged from 18-31% when compared to the pooled negative control. KK179 alfalfa event has the reduced lignin phenotype identified by the "sweet spot" selection method.

| Event | Dormancy germplasm | Event Mean | Delta | Delta LCI @ 90% | Delta UCI @ 90% | % Diff. | P-value |
|---|---|---|---|---|---|---|---|
| JJ041 | FD | 7.91 | −1.75 | −1.97 | −1.52 | −18.09 | <.001 |
| JJ266 | FD | 7.48 | −2.18 | −2.39 | −1.98 | −22.60 | <.001 |
| KK136 | FD | 7.01 | −2.64 | −2.90 | −2.39 | −27.40 | <.001 |
| KK179 | FD | 7.65 | −2.01 | −2.24 | −1.79 | −20.83 | <.001 |
| KK376 | FD | 7.37 | −2.29 | −2.55 | −2.04 | −23.75 | <.001 |
| KK465 | FD | 7.30 | −2.36 | −2.59 | −2.13 | −24.44 | <.001 |
| JJ041 | FD | 7.71 | −1.77 | −2.01 | −1.53 | −18.70 | <.001 |
| JJ266 | FD | 6.98 | −2.50 | −2.74 | −2.26 | −26.38 | <.001 |
| KK136 | FD | 7.38 | −2.10 | −2.34 | −1.86 | −22.14 | <.001 |
| KK179 | FD | 7.56 | −1.92 | −2.16 | −1.68 | −20.24 | <.001 |
| KK376 | FD | 6.51 | −2.97 | −3.21 | −2.73 | −31.33 | <.001 |
| KK465 | FD | 7.33 | −2.15 | −2.39 | −1.91 | −22.68 | <.001 |

Abbreviations:
ADL = Acid Detergent Lignin, % of dry matter;
LSD = Least Significant Difference;
FD = Fall Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

TABLE 5

Lower stem ADL measurements for the 6 reduced lignin alfalfa lead events in fall dormant (FD) germplasm 1 grown in 4 locations in 2009.

| Event | Event Mean | Control Mean | Delta | Delta LCI @ 90% | Delta UCI @ 90% | % Diff. | P-value |
|---|---|---|---|---|---|---|---|
| JJ041 | 9.46 | 10.79 | −1.32 | −1.55 | −1.09 | −12.26 | <.001 |
| JJ266 | 8.53 | 10.79 | −2.26 | −2.47 | −2.05 | −20.95 | <.001 |
| KK136 | 8.52 | 10.79 | −2.27 | −2.53 | −2.02 | −21.06 | <.001 |
| KK179 | 8.52 | 10.79 | −1.96 | −2.53 | −1.74 | −18.20 | <.001 |
| KK376 | 8.49 | 10.79 | −2.29 | −2.54 | −2.04 | −21.26 | <.001 |
| KK465 | 8.55 | 10.79 | −2.24 | −2.47 | −2.00 | −20.73 | <.001 |

Abbreviations:
ADL = Acid Detergent Lignin, % of dry matter;
LSD = Least Significant Difference;
FD = Fall Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

TABLE 6

Lower stem ADL measurements for the 6 reduced lignin alfalfa lead events in non-dormant (ND) germplasm 1 grown at 2 locations in 2009.

| Event | Event Mean | Control Mean | Delta | Delta LCI @ 90% | Delta UCI @ 90% | % Diff. | P-value |
|---|---|---|---|---|---|---|---|
| JJ041 | 9.42 | 11.73 | −2.31 | −2.61 | −2.02 | −19.72 | <.001 |
| JJ266 | 8.84 | 11.73 | −2.89 | −3.18 | −2.59 | −24.61 | <.001 |

TABLE 6-continued

Lower stem ADL measurements for the 6 reduced lignin alfalfa lead events in non-dormant (ND) germplasm 1 grown at 2 locations in 2009.

| Event | Event Mean | Control Mean | Delta | Delta LCI @ 90% | Delta UCI @ 90% | % Diff. | P-value |
|---|---|---|---|---|---|---|---|
| KK136 | 9.27 | 11.73 | −2.46 | −2.79 | −2.12 | −20.94 | <.001 |
| KK179 | 9.45 | 11.73 | −1.28 | −2.57 | −1.98 | −19.41 | <.001 |
| KK376 | 8.73 | 11.73 | −3.00 | −3.30 | −2.70 | −25.57 | <.001 |
| KK465 | 9.17 | 11.73 | −2.56 | −2.85 | −2.27 | −21.84 | <.001 |

Abbreviations:
ADL = Acid Detergent Lignin, % of dry matter;
LSD= Least Significant Difference;
FD= Fall Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

TABLE 7

Lower stem ADL measurements for the 6 reduced lignin alfalfa lead events in fall dormant (FD) germplasm 2 grown at 4 locations in 2009.

| Event | Event Mean | Control Mean | Delta | Delta LCI @ 90% | Delta UCI @ 90% | % Diff. | P-value |
|---|---|---|---|---|---|---|---|
| JJ041 | 9.31 | 10.89 | −1.58 | −1.81 | −1.35 | −14.50 | <.001 |
| JJ266 | 8.11 | 10.89 | −2.79 | −3.01 | −2.56 | −25.58 | <.001 |
| KK136 | 8.55 | 10.89 | −2.34 | −2.57 | −2.11 | −21.50 | <.001 |
| KK179 | 8.87 | 10.89 | −2.03 | −2.26 | −1.80 | −18.61 | <.001 |
| KK376 | 8.26 | 10.89 | −2.63 | −2.86 | −2.40 | −24.14 | <.001 |
| KK465 | 9.09 | 10.89 | −1.81 | −2.03 | −1.58 | −16.58 | <.001 |

Abbreviations:
ADL = Acid Detergent Lignin, % of dry matter;
LSD = Least Significant Difference;
ND = Non Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

TABLE 8

Lower stem ADL measurements for 6 reduced lignin alfalfa lead events in non dormant (ND) germplasm 2 grown at 2 locations in 2009.

| Event | Event Mean | Control Mean | Delta | Delta LCI @ 90% | Delta UCI @ 90% | % Diff. | P-value |
|---|---|---|---|---|---|---|---|
| JJ041 | 8.91 | 11.16 | −2.26 | −2.64 | −1.87 | −20.21 | <.001 |
| JJ266 | 8.53 | 11.16 | −2.63 | −3.02 | −2.25 | −23.61 | <.001 |
| KK136 | 8.85 | 11.16 | −2.31 | −2.69 | −1.92 | −20.67 | <.001 |
| KK179 | 8.75 | 11.16 | −2.41 | −2.80 | −2.02 | −21.58 | <.001 |
| KK376 | 8.35 | 11.16 | −2.81 | −3.20 | −2.42 | −25.16 | <.001 |
| KK465 | 9.14 | 11.16 | −2.03 | −2.41 | −1.64 | −18.15 | <.001 |

Abbreviations:
ADL = Acid Detergent Lignin, % of dry matter;
LSD = Least Significant Difference;
ND = Non Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

Tables 4-8 show 2009 data for lower stem ADL in a fall dormant (FD) and non dormant (ND) germplasms at 4 and 2 locations, respectively. The 6 event positive lines showed a significant ($p \leq 0.05$) reduction in ADL ranging from 12-26% when compared to the pooled negative control, with the lead event KK179 showing a reduction in ADL of 18-22%.

Example 7

NDFD Measurements in the Lower Stem of Reduced Lignin Alfalfa Events

TABLE 9

Lower stem NDFD measurements for the 6 reduced lignin alfalfa lead events in fall dormant (FD) germplasms grown at 3 locations in 2008.

| Event | Dormancy germplasm | Event Mean | Control Mean | Delta | Delta LCI @ 90% | Delta UCI @ 90% | % Diff. | P-value |
|---|---|---|---|---|---|---|---|---|
| JJ041 | FD | 32.68 | 27.70 | 4.98 | 4.23 | 5.73 | 17.98 | <.001 |
| JJ266 | FD | 33.58 | 27.70 | 5.88 | 5.20 | 6.56 | 21.23 | <.001 |
| KK136 | FD | 35.46 | 27.70 | 7.76 | 6.91 | 8.61 | 28.01 | <.001 |
| KK179 | FD | 33.52 | 27.70 | 5.82 | 5.08 | 6.57 | 21.02 | <.001 |
| KK376 | FD | 34.12 | 27.70 | 6.43 | 5.57 | 7.28 | 23.20 | <.001 |
| KK465 | FD | 35.33 | 27.70 | 7.63 | 6.88 | 8.38 | 27.55 | <.001 |
| JJ041 | FD | 33.27 | 27.70 | 5.56 | 4.69 | 6.44 | 20.08 | <.001 |
| JJ266 | FD | 34.98 | 27.70 | 7.27 | 6.40 | 8.15 | 26.25 | <.001 |
| KK136 | FD | 34.29 | 27.70 | 6.59 | 5.71 | 7.46 | 23.77 | <.001 |
| KK179 | FD | 33.13 | 27.70 | 5.42 | 4.54 | 6.30 | 19.57 | <.001 |
| KK376 | FD | 37.44 | 27.70 | 9.74 | 8.86 | 10.61 | 35.14 | <.001 |
| KK465 | FD | 35.34 | 27.70 | 7.64 | 6.76 | 8.52 | 27.57 | <.001 |

Abbreviations:
NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter));
FD = Fall Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

Lower stem NDFD for the 6 reduce lignin events in fall dormant (FD) germplasms at 3 locations. Event positive plants showed a significant ($p \leq 0.05$) increase in lower stem NDFD which ranged from 18-35% when compared to the pooled negative control.

TABLE 10

Lower stem NDFD measurements for the 6 reduced lignin alfalfa lead events in fall dormant (FD) germplasm 1 grown at 4 locations in 2009.

| Event | Dormancy germplasm | Event Mean | Control Mean | Delta | Delta LCI @ 90% | Delta UCI @ 90% | % Diff. | P-value |
|---|---|---|---|---|---|---|---|---|
| JJ041 | FD | 28.09 | 22.31 | 5.79 | 4.89 | 6.69 | 25.95 | <.001 |
| JJ266 | FD | 28.58 | 22.31 | 6.27 | 5.46 | 7.08 | 28.11 | <.001 |
| KK136 | FD | 28.88 | 22.31 | 6.57 | 5.58 | 7.56 | 29.46 | <.001 |
| KK179 | FD | 27.20 | 22.31 | 4.90 | 4.01 | 5.78 | 21.95 | <.001 |

TABLE 10-continued

Lower stem NDFD measurements for the 6 reduced lignin alfalfa lead events in fall dormant (FD) germplasm 1 grown at 4 locations in 2009.

| Event | Dormancy germplasm | Event Mean | Control Mean | Delta | Delta LCI @ 90% | Delta UCI @ 90% | % Diff. | P-value |
|---|---|---|---|---|---|---|---|---|
| KK376 | FD | 28.65 | 22.31 | 6.34 | 5.38 | 7.31 | 28.43 | <.001 |
| KK465 | FD | 28.21 | 22.31 | 5.91 | 4.99 | 6.83 | 26.49 | <.001 |

Abbreviations:
NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter));
FD = Fall Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

TABLE 11

Lower stem NDFD measurements for the 6 reduced lignin alfalfa lead events in non dormant (ND) germplasm 1 grown at 2 locations in 2009.

| Event | Dormancy germplasm | Event Mean | Control Mean | Delta | Delta LCI @ 90% | Delta UCI @ 90% | % Diff. | P-value |
|---|---|---|---|---|---|---|---|---|
| JJ041 | ND | 26.84 | 20.88 | 5.96 | 4.62 | 7.30 | 28.52 | <.001 |
| JJ266 | ND | 27.79 | 20.88 | 6.90 | 5.63 | 8.18 | 33.06 | <.001 |
| KK136 | ND | 27.47 | 20.88 | 6.59 | 5.14 | 8.05 | 31.56 | <.001 |
| KK179 | ND | 26.73 | 20.88 | 5.85 | 4.51 | 7.18 | 27.99 | <.001 |
| KK376 | ND | 27.19 | 20.88 | 6.31 | 4.97 | 7.65 | 30.21 | <.001 |
| KK465 | ND | 27.02 | 20.88 | 6.14 | 4.86 | 7.42 | 29.41 | <.001 |

Abbreviations:
NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter));
ND = Non Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

TABLE 12

Lower stem NDFD measurements for the 6 reduced lignin alfalfa lead events in fall dormant (FD) germplasm 2 grown at 4 locations in 2009.

| Event | Dormancy germplasm | Event Mean | Control Mean | Delta | Delta LCI @ 90% | Delta UCI @ 90% | % Diff. | P-value |
|---|---|---|---|---|---|---|---|---|
| JJ041 | FD | 27.96 | 22.11 | 5.85 | 5.01 | 6.69 | 26.46 | <.001 |
| JJ266 | FD | 29.97 | 22.11 | 7.86 | 7.01 | 8.70 | 35.54 | <.001 |
| KK136 | FD | 28.84 | 22.11 | 6.73 | 5.89 | 7.58 | 30.45 | <.001 |
| KK179 | FD | 27.32 | 22.11 | 5.21 | 4.37 | 6.06 | 23.58 | <.001 |
| KK376 | FD | 29.81 | 22.11 | 7.70 | 6.85 | 8.54 | 34.82 | <.001 |
| KK465 | FD | 27.37 | 22.11 | 5.26 | 4.41 | 6.10 | 23.78 | <.001 |

Abbreviations:
NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter));
FD = Fall Dormant;
ND = Non Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

TABLE 13

Lower stem NDFD measurements for the 6 reduced lignin alfalfa lead events in non dormant (ND) germplasm 2 grown at 2 locations in 2009.

| Event | Dormancy germplasm | Event Mean | Control Mean | Delta | Delta LCI @ 90% | Delta UCI @ 90% | % Diff. | P-value |
|---|---|---|---|---|---|---|---|---|
| JJ041 | ND | 28.10 | 22.39 | 5.71 | 4.15 | 7.26 | 25.48 | <.001 |
| JJ266 | ND | 28.73 | 22.39 | 6.34 | 4.78 | 7.89 | 28.29 | <.001 |
| KK136 | ND | 28.66 | 22.39 | 6.27 | 4.71 | 7.82 | 28.00 | <.001 |
| KK179 | ND | 27.76 | 22.39 | 5.37 | 3.81 | 6.92 | 23.98 | <.001 |
| KK376 | ND | 29.87 | 22.39 | 7.48 | 5.93 | 9.04 | 33.40 | <.001 |
| KK465 | ND | 28.95 | 22.39 | 56.56 | 5.00 | 8.11 | 29.29 | <.001 |

Abbreviations:
NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter));
ND = Non Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

Tables 10-13 show 2009 data for lower stem NDFD in fall dormant (FD) and non dormant (ND) germplasm at 4 and 2 locations, respectively. The 6 event positive reduced lignin alfalfa events showed a significant (p≤0.05) increase in NDFD ranging from 22-36% when compared to the pooled negative control, with the lead event KK179 showing an increase in NDFD of 22-28%.

Example 8

Vigor Rating for Reduced Lignin Alfalfa Events

TABLE 14

Vigor ratings for the 2 reduced lignin alfalfa events, JJ266 and KK179 compared to commercial checks and the null controls in 3 locations. The reduced lignin event KK179 resulted in no off-types for vigor rating scale. Plant vigor (scored 1-10, 10 being best) was taken 21 days after previous harvest, and in the second week of May for the spring score.

| Event | Location 1 | Location 2 | Location 3 | Mean |
|---|---|---|---|---|
| JJ266 | 8.0 | 7.4 | 7.8 | 7.7 |
| JJ266, null | 7.8 | 7.4 | 8.0 | 7.7 |
| KK179 | 8.0 | 7.6 | 7.6 | 7.7 |

TABLE 14-continued

Vigor ratings for the 2 reduced lignin alfalfa events, JJ266 and KK179 compared to commercial checks and the null controls in 3 locations. The reduced lignin event KK179 resulted in no off-types for vigor rating scale. Plant vigor (scored 1-10, 10 being best) was taken 21 days after previous harvest, and in the second week of May for the spring score.

| Event | Location 1 | Location 2 | Location 3 | Mean |
|---|---|---|---|---|
| KK179, null | 7.4 | 7.7 | 8.1 | 7.7 |
| Commercial Check 1 | 6.9 | 6.7 | 7.1 | 6.9 |
| Commercial Check 2 | 7.1 | 7.0 | 6.7 | 6.9 |
| Commercial Check 3 | 7.8 | 8.1 | 8.1 | 8.0 |
| Commercial Check 4 | 7.3 | 7.6 | 7.9 | 7.6 |

Example 9

ADL Measurements in the Whole Plant for Reduced Lignin Alfalfa Events

TABLE 15

Whole plant hay ADL measurements for the 6 reduced lignin alfalfa lead events in fall dormant (FD) germplasm 1 grown in 4 locations in 2009.

| Event | Event Mean | Control Mean | Delta | Delta LCI @ 90% | Delta UCI @ 90% | % Diff. | P-value |
|---|---|---|---|---|---|---|---|
| JJ041 | 4.96 | 5.66 | −0.69 | −1.55 | −0.44 | −12.27 | <.001 |
| JJ266 | 4.85 | 5.66 | −1.04 | −2.47 | −0.59 | −14.37 | <.001 |
| KK136 | 4.81 | 5.66 | −1.12 | −2.53 | −0.59 | −15.09 | <.001 |
| KK179 | 5.11 | 5.66 | −0.80 | −2.19 | −0.31 | −9.79 | <.001 |
| KK376 | 4.73 | 5.66 | −1.19 | −2.54 | −0.66 | −16.39 | <.001 |
| KK465 | 5.18 | 5.66 | −0.74 | −2.47 | −0.22 | −8.49 | 0.002 |

Abbreviations:
ADL = Acid Detergent Lignin, % of dry matter;
LSD = Least Significant Difference;
FD = Fall Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

TABLE 16

Whole plant hay ADL measurements for the 6 reduced lignin alfalfa lead events in non dormant (ND) germplasm 1 grown in 2 locations in 2009.

| Event | Event Mean | Control Mean | Delta | Delta LCI @ 90% | Delta UCI @ 90% | % Diff. | P-value |
|---|---|---|---|---|---|---|---|
| JJ041 | 5.40 | 6.16 | −0.77 | −1.22 | −0.31 | −12.43 | 0.006 |
| JJ266 | 5.27 | 6.16 | −0.89 | −1.30 | −0.48 | −14.47 | 0.000 |
| KK136 | 5.56 | 6.16 | −0.61 | −1.07 | −0.15 | −9.87 | 0.030 |
| KK179 | 5.41 | 6.16 | −0.76 | −1.19 | −0.32 | −12.25 | 0.004 |
| KK376 | 5.20 | 6.16 | −0.97 | −1.42 | −0.51 | −15.66 | 0.001 |
| KK465 | 5.57 | 6.16 | −0.60 | −1.00 | −0.19 | −9.69 | 0.016 |

Abbreviations:
ADL = Acid Detergent Lignin, % of dry matter;
LSD = Least Significant Difference;
ND = Non Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

TABLE 17

Whole plant hay ADL measurements for the 6 reduced lignin alfalfa lead events in fall dormant (FD) germplasm 2 grown in 4 locations in 2009.

| Event | Event Mean | Control Mean | Delta | Delta LCI @ 90% | Delta UCI @ 90% | % Diff. | P-value |
|---|---|---|---|---|---|---|---|
| JJ041 | 4.93 | 5.77 | −0.85 | −1.07 | −0.62 | −14.64 | <0.001 |
| JJ266 | 4.66 | 5.77 | −1.11 | −1.33 | −0.89 | −19.25 | <0.001 |
| KK136 | 5.12 | 5.77 | −0.65 | −0.88 | −0.43 | −11.34 | <0.001 |
| KK179 | 5.23 | 5.77 | −0.54 | −0.77 | −0.32 | −9.41 | <0.001 |
| KK376 | 4.61 | 5.77 | −1.16 | −1.39 | −0.93 | −20.09 | <0.001 |
| KK465 | 5.28 | 5.77 | −0.49 | −0.71 | −0.26 | −8.43 | <0.001 |

Abbreviations:
ADL = Acid Detergent Lignin, % of dry matter;
LSD = Least Significant Difference;
FD = Fall Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

Whole plant ADL data from 2009 across 4 locations is shown in Tables 15 and 17. The 6 reduced lignin positive events showed a significant ($p \leq 0.05$) decrease in ADL ranging from 8-19% when compared to the pooled negative control for both fall dormant germplasms. Event KK179 had a 9.8% and a 9.4% reduction in ADL in the fall dormant germplasms 1 and 2, respectively.

TABLE 18

Whole plant hay ADL measurements for the 6 reduced lignin alfalfa lead events in non dormant (ND) germplasm 2 grown in 2 locations in 2009.

| Event | Event Mean | Control Mean | Delta | Delta LCI @ 90% | Delta UCI @ 90% | % Diff. | P-value |
|---|---|---|---|---|---|---|---|
| JJ041 | 5.25 | 5.94 | −0.69 | −1.10 | −0.28 | −11.59 | 0.006 |
| JJ266 | 4.86 | 5.94 | −1.08 | −1.48 | −0.69 | −18.21 | <0.001 |
| KK136 | 5.57 | 5.94 | −0.37 | −0.76 | −0.02 | −6.22 | 0.123 |
| KK179 | 5.29 | 5.94 | −0.65 | −1.04 | −0.25 | −10.91 | 0.007 |
| KK376 | 5.02 | 5.94 | −0.92 | −1.33 | −0.51 | −15.47 | <0.001 |
| KK465 | 5.37 | 5.94 | −0.57 | −0.96 | −0.18 | −9.61 | 0.018 |

Abbreviations:
ADL = Acid Detergent Lignin, % of dry matter;
LSD = Least Significant Difference;
ND = Non Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

Whole plant ADL data from 2009 across 2 locations is shown in Tables 16 and 18. The 6 reduced lignin positive events in the non dormant germplasms showed a significant (p≤0.05) decrease in ADL ranging from 10-16% when compared to the pooled negative control. Five of the 6 events showed a significant decrease in ADL ranging from 10-18% when compared to the pooled negative control. Event KK179 had a 12.3% and 10.9% reduction in ADL in the non dormant germplasms 1 and 2, respectively.

TABLE 19

Whole plant hay ADL measurements for the reduced lignin alfalfa event KK179 in two fall dormant (FD) germplasms grown in 4 locations in 2009 compared to commercial checks.

| Commercial Check | Dormancy Germplasm | KK179 | Check Mean | Delta | Delta LCI @ 90% | Delta UCI @ 90% | % Diff. | P-value |
|---|---|---|---|---|---|---|---|---|
| 1 | FD germplasm 1 | 5.22 | 6.12 | −0.90 | −1.19 | −0.62 | −14.77 | <.001 |
| 2 | FD germplasm 1 | 5.22 | 5.69 | −0.47 | −0.76 | −0.18 | −8.31 | 0.008 |
| 3 | FD germplasm 1 | 5.22 | 5.38 | −0.17 | −0.46 | 0.13 | −3.08 | 0.350 |
| 4 | FD germplasm 1 | 5.22 | 5.59 | −0.38 | −0.67 | −0.09 | −6.75 | 0.034 |
| 1 | FD germplasm 2 | 5.10 | 6.12 | −1.02 | −1.31 | −0.73 | −16.67 | <.001 |
| 2 | FD germplasm 2 | 5.10 | 5.69 | −0.59 | −0.89 | −0.29 | −10.35 | 0.001 |
| 3 | FD germplasm 2 | 5.10 | 5.38 | −0.28 | −0.58 | 0.02 | −5.24 | 0.119 |
| 4 | FD germplasm 2 | 5.10 | 5.59 | −0.49 | −0.79 | −0.20 | −8.83 | 0.006 |

Abbreviations:
ADL = Acid Detergent Lignin, % of dry matter;
FD = Fall Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

TABLE 20

Whole plant hay ADL measurements for the reduced lignin alfalfa event KK179 in two non dormant (ND) germplasm grown in 2 locations in 2009 compared to commercial checks.

| Commercial Check | Germplasm | KK179 | Check Mean | Delta | Delta LCI @ 90% | Delta UCI @ 90% | % Diff. | P-value |
|---|---|---|---|---|---|---|---|---|
| 1 | ND germplasm 1 | 5.29 | 5.73 | −0.44 | −0.96 | 0.09 | −7.62 | 0.173 |
| 2 | ND germplasm 1 | 5.29 | 5.81 | −0.52 | −1.04 | 0.01 | −8.92 | 0.106 |
| 3 | ND germplasm 1 | 5.29 | 5.77 | −0.48 | −1.01 | 0.05 | −8.34 | 0.133 |
| 4 | ND germplasm 1 | 5.29 | 5.92 | −0.63 | −1.15 | −0.10 | −10.61 | 0.050 |
| 1 | ND germplasm 2 | 5.39 | 5.73 | −0.33 | −0.88 | 0.21 | −5.77 | 0.318 |
| 2 | ND germplasm 2 | 5.39 | 5.81 | −0.41 | −0.96 | 0.13 | −7.11 | 0.213 |
| 3 | ND germplasm 2 | 5.39 | 5.77 | −0.38 | −0.92 | 0.17 | −6.51 | 0.257 |
| 4 | ND germplasm 2 | 5.39 | 5.92 | −0.52 | −1.07 | 0.02 | −8.82 | 0.115 |

Abbreviations:
ADL = Acid Detergent Lignin, % of dry matter;
ND = Non Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

Tables 19 and 20 contain whole plant ADL data for the reduced lignin alfalfa event KK179 compared to commercial checks. The KK179 event showed a significant (p≤0.1) decrease in ADL when compared to 3 of the 4 fall dormant commercial checks, which ranged from 6.8-16.7% (Table 19, data from 4 locations). KK179 event in non dormant background germplasm (ND germplasm 1) showed a decrease (p≤0.2) in ADL compared to all 4 non dormant commercial checks ranging from 7.6-10.6% (Table 20, data from 2 locations). The KK179 event in non dormant background germplasm 2 showed an overall decrease (p≤0.2) in ADL compared to all 4 non dormant commercial checks with a significant (p≤0.1) decrease of 8.8% compared to commercial check 4 (data from 2 locations).

Example 10

NDFD Measurements in the Whole Plant for Reduced Lignin Alfalfa Events

TABLE 21

Whole plant hay NDFD measurements for the 6 reduced lignin alfalfa lead events in fall dormant (FD) germplasm 1 grown in 4 locations in 2009.

| Event | Event Mean | Control Mean | Delta | Delta LCI @ 90% | Delta UCI @ 90% | % Diff. | P-value |
|---|---|---|---|---|---|---|---|
| JJ041 | 45.38 | 39.47 | 5.90 | 4.32 | 7.49 | 14.96 | <0.001 |
| JJ266 | 44.00 | 39.47 | 4.53 | 3.15 | 5.92 | 11.48 | <0.001 |
| KK136 | 43.92 | 39.47 | 4.45 | 2.80 | 6.10 | 11.27 | <0.001 |
| KK179 | 42.44 | 39.47 | 2.97 | 1.47 | 4.47 | 7.53 | 0.001 |
| KK376 | 44.82 | 39.47 | 5.35 | 3.71 | 6.99 | 13.55 | <0.001 |
| KK465 | 42.13 | 39.47 | 2.66 | 1.07 | 4.25 | 6.74 | 0.006 |

Abbreviations:
NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter));
FD = Fall Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

TABLE 22

Whole plant hay NDFD measurements for the 6 reduced lignin alfalfa lead events in non dormant (ND) germplasm 1 grown in 2 locations in 2009.

| Event | Event Mean | Control Mean | Delta | Delta LCI @ 90% | Delta UCI @ 90% | % Diff. | P-value |
|---|---|---|---|---|---|---|---|
| JJ041 | 40.63 | 35.41 | 5.23 | 1.84 | 8.61 | 14.76 | 0.011 |
| JJ266 | 40.81 | 35.41 | 5.41 | 2.35 | 8.46 | 15.27 | 0.004 |
| KK136 | 38.66 | 35.41 | 3.25 | −0.19 | 6.70 | 9.19 | 0.120 |
| KK179 | 40.37 | 35.41 | 4.96 | 1.73 | 8.19 | 14.01 | 0.012 |
| KK376 | 39.75 | 35.41 | 4.35 | 0.96 | 7.73 | 12.28 | 0.035 |
| KK465 | 38.72 | 35.41 | 3.32 | 0.26 | 6.37 | 9.37 | 0.074 |

Abbreviations:
NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter));
ND = Non Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

TABLE 23

Whole plant hay NDFD measurements for the 6 reduced lignin alfalfa lead events in fall dormant (FD) germplasm 2 grown in 4 locations in 2009.

| Event | Event Mean | Control Mean | Delta | Delta LCI @ 90% | Delta UCI @ 90% | % Diff. | P-value |
|---|---|---|---|---|---|---|---|
| JJ041 | 44.42 | 38.96 | 5.46 | 3.92 | 7.00 | 14.02 | <.001 |
| JJ266 | 45.19 | 38.96 | 6.22 | 4.72 | 7.73 | 15.98 | <.001 |
| KK136 | 43.63 | 38.96 | 4.66 | 3.16 | 6.17 | 11.97 | <.001 |
| KK179 | 42.56 | 38.96 | 3.60 | 2.10 | 5.10 | 9.24 | <.001 |
| KK376 | 45.41 | 38.96 | 6.45 | 4.90 | 7.99 | 16.54 | <.001 |
| KK465 | 41.52 | 38.96 | 2.55 | 1.05 | 4.06 | 6.55 | 0.005 |

Abbreviations:
NDFD = Neutral Detergent Fiber Digestibility, % of NDF; (NDF = neutral detergent fiber. Represents the indigestible and slowly digestible components in plant cell wall (cellulose, hemicellulose, lignin (units = % of dry matter));
FD = Fall Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

Whole plant NDFD data from 2009 across 4 locations is shown in Tables 21 and 23. The 6 reduced lignin positive events in fall dormant germplasms showed a significant (p≤0.05) increase in NDFD ranging from 7-16% when compared to the pooled negative control. Event KK179 had a 7.5% and 9.2% increase in NDFD in the fall dormant germplasms 1 and 2 respectively.

TABLE 24

Whole plant hay NDFD measurements for the 6 reduced lignin alfalfa lead events in non dormant (ND) germplasm 2 grown in 2 locations in 2009.

| Event | Event Mean | Control Mean | Delta | Delta LCI @ 90% | Delta UCI @ 90% | % Diff. | P-value |
|---|---|---|---|---|---|---|---|
| JJ041 | 40.95 | 37.21 | 3.74 | 0.68 | 6.81 | 10.06 | 0.045 |
| JJ266 | 42.06 | 37.21 | 4.85 | 1.92 | 7.79 | 13.05 | 0.007 |
| KK136 | 40.24 | 37.21 | 3.03 | 0.10 | 5.97 | 8.15 | 0.089 |
| KK179 | 41.48 | 37.21 | 4.27 | 1.34 | 7.21 | 11.49 | 0.017 |
| KK376 | 42.22 | 37.21 | 5.01 | 1.95 | 8.08 | 13.47 | 0.007 |
| KK465 | 40.35 | 37.21 | 3.15 | 0.21 | 6.08 | 8.46 | 0.078 |

Abbreviations:
NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter));
ND = Non Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

Whole plant NDFD data from 2009 across 2 locations is shown in Tables 22 and 24. The 6 reduced lignin positive events in non dormant germplasms showed a significant (p≤0.1) increase in NDFD ranging from 8-15% when compared to the pooled negative control. Event KK179 had a 14.0% and 11.5% increase in NDFD in the non dormant germplasms 1 and 2 respectively.

TABLE 25

Whole plant hay NDFD measurements for the reduced lignin alfalfa event KK179 in two fall dormant (FD) germplasms grown in 4 locations in 2009 compared to commercial checks.

| Commercial Check | Germplasm | KK179 | Check Mean | Delta | Delta LCI @ 90% | Delta UCI @ 90% | % Diff. | P-value |
|---|---|---|---|---|---|---|---|---|
| 1 | FD germplasm 1 | 42.17 | 36.10 | 6.07 | 4.27 | 7.86 | 16.80 | <.001 |
| 2 | FD germplasm 1 | 42.17 | 40.34 | 1.83 | 0.00 | 3.66 | 4.53 | 0.101 |
| 3 | FD germplasm 1 | 42.17 | 41.27 | 0.89 | −0.94 | 2.72 | 2.16 | 0.423 |
| 4 | FD germplasm 1 | 42.17 | 38.87 | 3.29 | 1.46 | 5.12 | 8.47 | 0.003 |
| 1 | FD germplasm 2 | 42.03 | 36.10 | 5.93 | 4.11 | 7.76 | 16.44 | <.001 |
| 2 | FD germplasm 2 | 42.03 | 40.34 | 1.70 | −0.17 | 3.56 | 4.21 | 0.134 |
| 3 | FD germplasm 2 | 42.03 | 41.27 | 0.76 | −1.10 | 2.63 | 1.84 | 0.502 |
| 4 | FD germplasm 2 | 42.03 | 38.87 | 3.16 | 1.30 | 5.03 | 8.13 | 0.005 |

Abbreviations:

NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter));

FD = Fall Dormant;

Delta = difference between Event and Control means (Event − Control);

% Diff = Percent difference between Event and Control (Delta/Control * 100);

Delta LCI @90% = Lower Confidence Interval of Delta value using an alpha level of 0.10;

Delta UCI @90% = Upper Confidence Interval of Delta value using an alpha level of 0.10;

P-value = probability of a greater absolute difference under the null hypothesis (2-tailed test for significance).

TABLE 26

Whole plant hay NDFD measurements for the reduced lignin alfalfa event KK179 in two non dormant (ND) germplasms grown in 2 locations in 2009 compared to commercial checks.

| Commercial Check | Germplasm | KK179 | Check Mean | Delta | Delta LCI @ 90% | Delta UCI @ 90% | % Diff. | P-value |
|---|---|---|---|---|---|---|---|---|
| 1 | ND germplasm 1 | 41.46 | 37.77 | 3.68 | −0.27 | 7.64 | 9.75 | 0.126 |
| 2 | ND germplasm 1 | 41.46 | 37.12 | 4.34 | 0.39 | 8.30 | 11.70 | 0.071 |
| 3 | ND germplasm 1 | 41.46 | 34.71 | 6.74 | 2.79 | 10.70 | 19.43 | 0.005 |
| 4 | ND germplasm 1 | 41.46 | 35.70 | 5.75 | 1.80 | 9.71 | 16.12 | 0.017 |
| 1 | ND germplasm 2 | 40.38 | 37.77 | 2.60 | −1.49 | 6.70 | 6.89 | 0.296 |
| 2 | ND germplasm 2 | 40.38 | 37.12 | 3.26 | −0.84 | 7.36 | 8.79 | 0.190 |
| 3 | ND germplasm 2 | 40.38 | 34.71 | 5.66 | 1.57 | 9.76 | 16.31 | 0.023 |
| 4 | ND germplasm 2 | 40.38 | 35.70 | 4.67 | 0.58 | 8.77 | 13.09 | 0.061 |

Abbreviations:

NDFD = Neutral Detergent Fiber Digestibility, % of NDF (NDF = neutral detergent fiber. Represents the indigestible and slowly digestible components in plant cell wall (cellulose, hemicellulose, lignin (units = % of dry matter));

ND = Non Dormant; Delta = difference between Event and Control means (Event − Control);

% Diff = Percent difference between Event and Control (Delta/Control * 100);

Delta LCI @90% = Lower Confidence Interval of Delta value using an alpha level of 0.10;

Delta UCI @90% = Upper Confidence Interval of Delta value using an alpha level of 0.10;

P-value = probability of a greater absolute difference under the null hypothesis (2-tailed test for significance).

Tables 25 and 26 contain whole plant NDFD data for the reduced lignin alfalfa event KK179 compared to commercial checks. The KK179 event showed an increase (p≤0.2) in NDFD when compared to 3 of the 4 fall dormant commercial checks which ranged from 4.2-16.8% (Table 25, data from 4 locations). KK179 event showed an increase (p≤0.2) in NDFD compared to all 4 non dormant commercial checks (ND germplasm 1) ranging from 9.8-19.4% (Table 26, data from 2 locations). The KK179 event showed an increase (p≤0.2) in NDFD compared to all 4 non dormant commercial checks (ND germplasm 2), which ranged from 8.8-16.3% (Table 26, data from 2 locations).

Example 11

Yield Across Location Analysis for Reduced Lignin Alfalfa Events

TABLE 27

Yield (fresh weight) across location analysis for 6 reduced lignin events for in fall dormant (FD) and non-dormant (ND) backgrounds compared to pooled negative controls. There were no significant decreases in yield detected for lead event KK179 when compared to the pooled negative control.

| Event | Dormancy germplasm | Year | Event Mean | Control Mean | Delta | Delta LCI @ 90% | Delta UCI @ 90% | % Diff. | P-value |
|---|---|---|---|---|---|---|---|---|---|
| JJ041 | FD | 2008 | 337.56 | 349.32 | −11.76 | −42.86 | 19.35 | −3.37 | 0.532 |
| JJ266 | FD | 2008 | 364.72 | 349.32 | 15.40 | −12.94 | 43.74 | 4.41 | 0.370 |
| KK136 | FD | 2008 | 306.67 | 349.32 | −42.65 | −78.12 | −7.19 | −12.21 | 0.048 |
| KK179 | FD | 2008 | 368.51 | 349.32 | 19.19 | −11.91 | 50.30 | 5.49 | 0.309 |
| KK376 | FD | 2008 | 354.92 | 349.32 | 5.60 | −29.85 | 41.05 | 1.60 | 0.794 |
| KK465 | FD | 2008 | 358.74 | 349.32 | 9.42 | −21.68 | 40.53 | 2.70 | 0.617 |
| JJ041 | FD | 2009 | 1148.41 | 1591.58 | −143.17 | −278.80 | −7.55 | −9.00 | 0.083 |
| JJ266 | FD | 2009 | 156.50 | 1591.58 | −26.08 | −147.97 | 95.82 | −1.64 | 0.724 |
| KK136 | FD | 2009 | 1468.30 | 1591.58 | −123.28 | −269.17 | 22.61 | −7.75 | 0.164 |
| KK179 | FD | 2009 | 1577.84 | 1591.58 | −13.74 | −145.29 | 117.81 | −0.86 | 0.863 |
| KK376 | FD | 2009 | 1371.19 | 1591.58 | −220.39 | −361.43 | −79.35 | −13.85 | 0.011 |
| KK465 | FD | 2009 | 1459.44 | 1591.58 | −132.14 | −272.37 | 8.09 | −8.30 | 0.121 |
| JJ041 | ND | 2009 | 591.17 | 764.86 | −173.70 | −292.96 | −54.43 | −22.71 | 0.018 |
| JJ266 | ND | 2009 | 758.32 | 764.86 | −6.54 | −119.09 | 106.01 | −0.86 | 0.923 |
| KK136 | ND | 2009 | 771.81 | 764.86 | 6.95 | −121.20 | 135.10 | 0.91 | 0.928 |
| KK179 | ND | 2009 | 754.11 | 764.86 | −10.75 | −130.04 | 108.54 | −1.41 | 0.881 |
| KK376 | ND | 2009 | 584.31 | 764.86 | −180.55 | −299.84 | −61.25 | −23.61 | 0.014 |
| KK465 | ND | 2009 | 637.67 | 764.86 | −127.20 | −239.75 | −14.65 | −16.63 | 0.064 |

Abbreviations:
Yield= Yield calculated on a per plant basis in grams;
FD= Fall Dormant;
ND= Non Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

The data in Table 27 shows the across location yield analysis for the 6 reduced lignin events in the fall dormant (FD) and non dormant (ND) germplasms compared to the pooled negative control. No significant decrease in yield is detected for KK179 when compared to the pooled negative controls.

TABLE 28

Yield (fresh weight) across location analysis for Event KK179 compared to commercial checks. Yield data for reduced lignin alfalfa lead event in fall dormant (FD) and non-dormant (ND) germplasms resulted in no significant yield decrease when compared to 8 commercial checks.

| Commercial Check | Dormancy germplasm | Year | Event Mean | Control Mean | Delta | LCI @ 90% | Delta UCI @ 90% | % Diff. | P-value |
|---|---|---|---|---|---|---|---|---|---|
| 1 | FD | 2008 | 368.51 | 239.29 | 129.22 | 92.13 | 166.31 | 54.00 | <.001 |
| 2 | FD | 2008 | 368.51 | 308.06 | 60.45 | 23.35 | 97.54 | 19.62 | 0.008 |
| 3 | FD | 2008 | 368.51 | 349.47 | 19.05 | −18.05 | 56.14 | 5.45 | 0.397 |
| 4 | FD | 2008 | 368.51 | 301.09 | 67.42 | 30.33 | 104.51 | 22.39 | 0.003 |
| 1 | FD | 2009 | 1361.60 | 1106.96 | 254.64 | 112.59 | 396.69 | 23.00 | 0.003 |
| 2 | FD | 2009 | 1361.60 | 1289.66 | 71.94 | −72.74 | 216.62 | 5.58 | 0.412 |
| 3 | FD | 2009 | 1361.60 | 1396.58 | −34.99 | −179.66 | 109.69 | −2.51 | 0.690 |
| 4 | FD | 2009 | 1361.60 | 1225.01 | 136.59 | −8.09 | 281.27 | 11.15 | 0.120 |
| 5 | ND | 2009 | 752.63 | 735.61 | 17.03 | −95.75 | 129.80 | 2.31 | 0.802 |
| 6 | ND | 2009 | 752.63 | 803.99 | −51.36 | −164.13 | 61.42 | −6.39 | 0.451 |

TABLE 28-continued

Yield (fresh weight) across location analysis for Event KK179 compared to commercial checks.
Yield data for reduced lignin alfalfa lead event in fall dormant (FD) and non-dormant (ND)
germplasms resulted in no significant yield decrease when compared to 8 commercial checks.

| Commercial Check | Dormancy germplasm | Year | Event Mean | Control Mean | Delta | LCI @ 90% | Delta UCI @ 90% | % Diff. | P-value |
|---|---|---|---|---|---|---|---|---|---|
| 7 | ND | 2009 | 752.63 | 698.51 | 54.12 | −58.66 | 166.89 | 7.75 | 0.427 |
| 8 | ND | 2009 | 752.63 | 618.75 | 133.89 | 21.11 | 246.66 | 21.64 | 0.052 |

Abbreviations:
Yield = Yield calculated on a per plant basis in grams;
FD = Fall Dormant;
ND = Non Dormant;
Delta = difference between Event and Control means (Event − Control);
% Diff = Percent difference between Event and Control (Delta/Control * 100);
Delta LCI @90% = Lower Confidence Interval of Delta value using an alpha level of 0.10;
Delta UCI @90% = Upper Confidence Interval of Delta value using an alpha level of 0.10;
P-value = probability of a greater absolute difference under the null hypothesis (2-tailed test for significance).

Improving fiber digestibility of alfalfa offers growers the ability to manage risk and increase the likelihood of harvesting high quality alfalfa hay/haylage. Sixty-one events were initially studied in 2007 with multi-year, multi-location plots established in 2008 with six elite events. Results demonstrate a significant increase in forage digestibility as measured by neutral detergent fraction (NDFD) at the 10% bloom stage.

Multi-location trials were planted in 2008 in two dormancy backgrounds; data was collected over two seasons in 2008 and 2009. Significant increases (6.7-16%) in whole plant digestibility for positive selections versus null controls were observed for all six events by dormancy combinations. The field performance along with the molecular analysis has identified a lead event KK179, which demonstrated significant digestibility increase across two dormancies, fall dormant (FD) and non-dormant germplasm groupings. KK179 shows a 7.5-14% increase in digestibility (NDFD) when compared to the pooled null control, 2-19% increase in digestibility when compared to commercial checks and 20-28% increase in lower stem across multiple years (as compared to the pooled null control). Whole plant KK179 lignin levels (ADL) are reduced by approximately 10-12% when compared to the pooled null control, and 18-22% reduction in lower stem across multiple years (as compared to the pooled null control). No significant decrease in yield was detected for KK179 as compared to the pooled null control.

Example 12

Alfalfa Management Practices

Planting (Alfalfa Management Guide, 2011): The Spring season is the preferred season over late summer seeding to plant alfalfa in the northern states and provides for increased opportunities for successful stand establishment. Spring seeding of alfalfa can begin as soon as the potential for damage from spring frosts has passed. For late summer seedings, alfalfa is grown for at least 6 weeks after germination in order to promote survival during the winter. This allows for the crown of the plant to store root reserves for winter survival and spring re-growth.

Factors That Effect Quality (Orloff and Marble, 1997): Alfalfa management includes cutting and harvesting practices, which are the primary methods by which growers can influence the nutritional quality of alfalfa hay, and it has profound effects on forage yield and stand life, High nutritive forage quality of alfalfa from a nutrition perspective depends on the livestock source class as it relates to the feeding value of the hay. Forage quality is a direct function of both forage intake and digestibility. As forage quality increases, feed intake and digestibility increase. Alfalfa management practices influence alfalfa hay quality. Stage of maturity at the time of cutting is one of the most important factors in alfalfa management. Yield increases with advancing maturity. In contrast to yield, forage quality declines with advancing maturity of the alfalfa plant, so harvest management is a compromise between maximizing yields and maximizing quality. Forage quality is also influenced by alfalfa variety selection, hay-making practices, and environmental inputs, such as seasonal variations in light, moisture, temperature, and photoperiod or day length.

Harvest Management (Orloff and Marble, 1997): The decision of when to cut and how to cut alfalfa are major factors in yield, quality, and stand persistence. As a perennial plant, alfalfa stores some of the carbohydrates in its crown and roots, After cutting, this process takes about 2 to 3 weeks, or until the alfalfa plant attains a height of 6 to 8 inches. From this point, the plant begins replenishing root reserves. The carbohydrate reserves in roots and crowns increase with plant maturity until the time of full flowering. The grower can obtain maximum yield when alfalfa reaches full bloom, however the highest yields are sometimes obtained at around 50% bloom. The interval between first and second cuttings, or second and third cuttings, is generally between 30 to 50 days. The time depends on the weather conditions and the alfalfa variety. Too-frequent cutting results in reduced vigor and, often, weed infestation, Another method of scheduling alfalfa harvests uses the growth stage of alfalfa to indicate the appropriate time to cut and the number of cuttings per season. Alfalfa harvests can also occur at a specific growth stage (such as bud, late-bud, 10% bloom, etc.). This method takes into account the effects of environmental and varietal differences and results in more consistent, predictable forage yield and quality.

Cutting (Alfalfa Management Guide, 2011): Maximum yields can be obtained at the 3-inch cutting height with a time of two to three weeks recommended as a re-growth period or until the alfalfa attains a height of 6 to 8 inches. From this point, the plant begins replenishing the carbohydrate reserve stores in its crown and roots. Current recommendations regarding cutting height of alfalfa are designed to maximize yield while maintaining high quality forages and stand longevity. Forage growers frequently cut forages at a height of 3-inches or more. However, alfalfa forages harvested three or four times per season produced more total forage when cut at a 1-inch height versus cutting at 3 inches or more (Kust and Smith, 1961, Smith and Nelson, 1967). These practices result in a forage yield benefit to cutting at shorter heights when alfalfa plants are not under stress or low in root carbohydrate levels (Sheaffer et al., 1988).

First Cutting

The first cutting from fall-planted or previously established stands of the alfalfa plants is normally timed to coincide with most plants having flower buds formed or when new crown shoots have grown no more than 1 to 2 inches. Since flowering is controlled by day length, the first growth is often ready to harvest before flower formation, which usually occurs in late April or early May. The first growth has a tendency to be fast and have increased height and is prone to increased lodging, and thus it is recommended to harvest before lodging occurs. Alfalfa growth in the spring is primarily from crown buds and depends on temperature and available root energy reserves. Shoot growth after the first harvest originates from both crown and axillary buds. When alfalfa is cut very short (1-inch or less), most of the axillary buds are removed and new shoots must come from the crown buds (Wiederholt and Schneider, 2007). Seedling stands planted in spring should not be harvested until at least 50% of stems show flower formation, or lodging appears evident. Delaying harvest will allow seedling roots to develop further.

Second and Subsequent Cuttings

The second and subsequent cuttings are made when 10% to 25% of stems have flowers present. It takes approximately 5 to 10 days for alfalfa to advance from the bud stage of growth to the 25% flower stage. In general the re-growth period for alfalfa will reach favorable cutting stage every 28 to 35 days. During hot, dry weather, plants may flower profusely prior to 30 days of a re-growth period and before the plants reach a height of 10 inches. In such cases, it is best to graze or cut the short growth when it has been 35 to 40 days since last harvest cutting. Once the plants have flowered extensively, those specific stems will not produce any more growth and their continued presence tends to retard new growth, even when favorable conditions occur.

Fall Cutting Management

For Fall cutting management, four to six weeks of re-growth is needed for plants to build carbohydrates prior to the first killing frost (24° F.); 10 to 14 inches of growth is recommended. After several frosts but before the leaves begin to wilt and drop, this growth should be harvested to maintain the quality of the feed and reduce residue, which assists with pest control.

Agronomic Practices and Sample Collection: Optimal agronomic practices used for this plot included fertility management, weed control, insect control, and moisture. The first growth on the transplants in the field was clipped with no data collection, in order to avoid variable data on the young transplants. The target maturity for remaining data collection was 10% bloom. This level of maturity allows for lignification of the stem to help in sorting events. Plant tissue is collected using hand shears to avoid losing any of the samples and to keep cutting height uniform. The uniform cutting height for all harvests was 2.5" above ground level. This is the typical height for commercial forage harvesting. All locations were managed for optimum growth and winter survival. Insect and weed control were done as needed to eliminate variability within the plot. Plant spacing within a row was 15" with 30" between rows.

REFERENCES

Kust, C. A., and D. Smith. 1961. Influence of harvest management on levels of carbohydrate reserves, longevity of stands and yield so hay and protein from Vernal alfalfa. Crop Sci. 1:267-269.

Orloff, S. B. and Marble, V. L Intermountain Alfalfa Management Steve B. Orloff, Editor Cooperative Extension Siskiyou County, CA, University of California copy right date=1997

Sheaffer, C. C., G. D. Lacefield, and V. L. Marble. 1988. Cutting schedules and stands. P. 411-437. In A. A. Hanson et al. (ed.) Alfalfa and alfalfa improvement. Agron. Monogr. 29. ASA, CSSA, SSSA, Madison, Wis.

Smith, D. and C. J. Nelson. 1967. Growth of birdsfoot trefoil and alfalfa. I. Responses to height and frequency of cutting. Crop Sci. 7:130-133.

University of Wisconsin Forage and Research Extension—Alfalfa Management Guide

University of Wisconsin Cooperative Extension, Minnesota Extension Center, University of Minnesota, Iowa State University, Alfalfa Management Guide, American Society of Agronomy, Crop Science Society of America, Soil Science Society of America, copy right 2011.

Wiederholdt, R. and Schneider N. 2007. The long and short of Alfalfa cutting height, Marshfield Agriculture Research Station (MARS) Agriculture Research Station (MARS)

What is claimed is:

1. A method to select an alfalfa plant with enhanced food value components from a population of alfalfa plants, wherein said population of alfalfa plants comprises a recombinant DNA molecule and wherein a portion of said recombinant DNA molecule is homologous or complementary to SEQ ID NO:1 or SEQ ID NO:2, comprising:
   (a) measuring the concentration of acid detergent lignin (ADL) in a lower stem tissue from each of said alfalfa plants in said population of alfalfa plants, wherein said concentration of ADL is reduced between 12% and about 31% compared to a lower stem tissue of an alfalfa plant not comprising said DNA molecule;
   (b) measuring the concentration of guaiacyl lignin (G lignin) in said lower stem tissue, wherein said G lignin is reduced by about 25% or greater in said lower stem tissue compared to a lower stem tissue of an alfalfa plant not comprising said DNA molecule;
   (c) measuring the neutral detergent fiber digestibility (NDFD) components in said lower stem tissue, wherein said NDFD value is increased by greater than 18% in said lower stem tissue compared to a lower stem tissue of an alfalfa plant not comprising said DNA molecule;
   (d) selecting an alfalfa plant that comprises the enhanced feed value components of steps (a)-(c); and
   (e) growing said alfalfa plant selected in step (d).

2. The method of claim 1, wherein said recombinant DNA molecule comprises a promoter molecule capable of transcription of an operably linked DNA molecule in a plant vascular tissue, and wherein a portion of said operably linked DNA molecule is homologous or complementary to SEQ ID NO:1 or SEQ ID NO:2.

3. The method of claim 1, further comprising the step of measuring the vigor of said growing alfalfa plant, wherein said vigor is 90% or greater compared to an alfalfa plant not comprising said recombinant DNA molecule.

4. The method of claim 1, wherein a hay or haylage is produced by growing said alfalfa plant.

5. The method of claim 4, wherein said hay or haylage is measured for said enhanced feed value components comprising:
   (a) measuring the ADL concentration of a sample of said hay or haylage, wherein said ADL concentration is between 80% and 92% compared to alfalfa hay not comprising said recombinant DNA molecule; and
   (b) measuring the neutral detergent fiber digestibility (NDFD) component in said sample of said hay or haylage, wherein said NDFD value is between 107% and 125% compared to alfalfa hay not comprising said recombinant DNA molecule.

6. The method of claim 1, further comprising growing said alfalfa plant to maturity and collecting progeny alfalfa seed from said plant.

7. An alfalfa seed produced by the method of claim 6, wherein said seed comprises a recombinant DNA molecule and wherein a portion of said recombinant DNA molecule is homologous or complementary to SEQ ID NO:1 or SEQ ID NO:2 and wherein the plant grown from said seed comprises:
   (a) a concentration of ADL in the lower stem that is reduced between 12% and about 31% compared to a lower stem tissue of an alfalfa plant not comprising said DNA molecule; and,
   (b) a guaiacyl lignin in lower stem tissue that is reduced by about 25% or greater compared to a lower stem tissue of an alfalfa plant not comprising said DNA molecule; and,
   (c) a neutral detergent fiber digestibility value that is increased by greater than 18% in lower stem tissue compared to the lower stem tissue of an alfalfa plant not comprising said DNA molecule.

8. An alfalfa plant grown from the seed of claim 7, wherein said plant comprises an ADL concentration in a lower stem tissue that is reduced by between 12% and 31% and an ADL concentration in a hay produced from said plant that is reduced to between 80% and 92%, compared to a lower stem tissue and hay of an alfalfa plant not comprising said recombinant DNA molecule.

9. An alfalfa plant grown from the seed of claim 7, wherein said plant comprises a G lignin concentration in a lower stem tissue that is reduced by about 25% or greater compared to a lower stem tissue or hay of an alfalfa plant not comprising said recombinant DNA molecule.

10. An alfalfa plant grown from the seed of claim 7, wherein said plant comprises an NDFD value in a lower stem tissue of 122% or greater compared to a lower stem tissue of an alfalfa plant not comprising said recombinant DNA molecule.

11. An alfalfa plant grown from the seed of claim 7, wherein said plant comprises an NDFD value in a hay produced from said plant of between about 107% and about 125% or greater compared to a hay of an alfalfa plant not comprising said recombinant DNA molecule.

12. An alfalfa hay with enhanced feed value components, the hay comprising a recombinant DNA molecule, wherein a portion of said recombinant DNA molecule is homologous or complementary to SEQ ID NO:1 or SEQ ID NO:2, and wherein said alfalfa hay further comprises:
   (a) an ADL concentration of between about 80% and about 92% of an ADL concentration of an alfalfa hay not comprising said recombinant DNA molecule,
   (b) a G lignin concentration that is reduced by about 25% or greater compared to an alfalfa hay not comprising said recombinant DNA molecule; and
   (c) an NDFD value of between 107% and 125% compared to an alfalfa hay not comprising said recombinant DNA molecule.

13. A processed alfalfa product comprising enhanced feed value components, the product comprising a recombinant DNA molecule, wherein a portion of said DNA molecule is homologous or complementary to SEQ ID NO:1 or SEQ ID NO:2, and wherein said processed alfalfa produce further comprises:
   (a) an ADL concentration of between about 80% and about 92% of an ADL concentration of an alfalfa product not comprising said recombinant DNA molecule;
   (b) a G lignin concentration that is reduced by about 25% greater compared to an alfalfa product not comprising said recombinant DNA molecule; and
   (c) an NDFD value of between 107% and 125% compared to an alfalfa product not comprising said recombinant DNA molecule.

14. The method of claim 4, wherein said haylage is measured for said enhanced feed value components comprising measuring the ADL concentration of a sample of said hay, wherein said ADL concentration in the lower stem is decreased by between 15% and 30% compared to commodity alfalfa and by between 8% and 15% in the plant.

15. The method of claim 1, wherein one or more transgenic events are selected to produce enhanced forage quality and good agronomic performance.

* * * * *

SEQUENCE LISTING

```
<160> NUMBER OF SEQ ID NOS: 7

<210> SEQ ID NO 1
<211> LENGTH: 300
<212> TYPE: DNA
<213> ORGANISM: Medicago sativa

<400> SEQUENCE: 1
gtctacactg gctactccct ccttgccact gccctagcta ttcctgaaga tggaaagatt      60
ttggctatgg acattaacaa agaaaattac gaattgggtc tacctgtaat taaaaaagct     120
ggtgttgatc acaaaattga tttcagagaa ggtccagctc ttccagttct tgatgaaatg     180
atcaaagacg aaaagaatca tggtagctac gatttcatt ttgtggatgc tgacaaagac      240
aattacctca actaccataa gaggttaatt gatcttgtta aagtgggagg tgtgatcggg     300
```

```
<210> SEQ ID NO 2
<211> LENGTH: 450
<212> TYPE: DNA
<213> ORGANISM: Medicago sativa

<400> SEQUENCE: 2
gtcttcccaa gagaacatga agccatgaaa gagttgagag aggtcacagc aaaacaccca        60
tggaacatca tgacaacctc tgcagatgaa ggacaatttt tgagcatgct ccttaaactt       120
atcaatgcta agaataccat ggaaattggt gtctacactg ctactccct ccttgccact        180 gccctagcta ttcctgaaga tggaaagatt ttggctatgg acattaacaa agaaaattac       240
gaattgggtc tacctgtaat taaaaaagct ggtgttgatc acaaaattga tttcagagaa       300
ggtccagctc ttccagttct tgatgaaatg atcaaagacg aaaagaatca tggtagctac       360
gatttcattt ttgtggatgc tgacaaagac aattacctca actaccataa gaggttaatt       420
gatcttgtta aagtgggagg tgtgatcggg                                       450

<210> SEQ ID NO 3
<211> LENGTH: 151
<212> TYPE: DNA
<213> ORGANISM: Artificial sequence
<220> FEATURE:
<223> OTHER INFORMATION: synthetic sequence; RNA loop between sense and
      antisense arm

<400> SEQUENCE: 3
accaatttcc atggtattct tagcattgat aagtttaagg agcatgctca aaaattgtcc        60
ttcatctgca gaggttgtca tgatgttcca tgggtgtttt gctgtgacct ctctcaactc       120
tttcatggct tcatgttctc ttgggaagac a                                     151

<210> SEQ ID NO 4
<211> LENGTH: 67
<212> TYPE: DNA
<213> ORGANISM: Artificial sequence
<220> FEATURE:
<223> OTHER INFORMATION: synthetic sequence; 5 prime end of the RNA loop

<400> SEQUENCE: 4
taacatactt cctcaatgga gcatcagggg gtgcaaccac agatccattc cataaggtgt        60
tgtcgta                                                                 67

<210> SEQ ID NO 5
<211> LENGTH: 1023
<212> TYPE: DNA
<213> ORGANISM: Phaseolus vulgaris

<400> SEQUENCE: 5
aaaagtctaa gccaatattc attattttt atttatgctt aacatttatg ttcaagccaa        60
tagtaacaag aagatgaact ggttttgtat attaattcaa tataaccaat ccctgtggag       120
tgatttagtt gaaaggatct acaattctaa agatgatgag ttaaaccct gccgaagttg        180 tagttgaatc ttaaacttac ttttctaaat agtaacacct gccataaata ctagctgcat       240
cttaatttct ctacctcccc cacactctgg catggcggcc ctgtcgtttt cttgctccat       300 tttttttct attatcacac ttttcttt catttctttc ttgttatctg taaatccgtg          360
tcctttcttc taagtaatta ctaaaacaaa tgctaaagaa acacatttat ttatttattt       420
ttatctttct aaccctattt aaccagtttt agaagccaat tcccaggaat catagttcac       480
tttaactatg tttttttta gtgagaagaa gacaaaagat gaatgattgg ttgcgattcc       540
```

```
ttgccctttt gttcttctta tatatatata tatatatata tatatatata tatacctaga      600
aaagataata tgtacgttga aatctttgtt aaaaggaacc agaaaatgta aggattagga      660
atttaatttc gtagttgggt aacatttatt aattaatcaa ttaattaatt aattgattga      720
tttatacgtc tatcttctat tccacgtcct gtgttggtag ggaagtacag agaagttagg      780
ttctagtcca caaggtgaca tcgcacccag agaagggag aaaaaatgcc acgtcgcgca       840
atgagagccg ctgatgcagg ctggtaatcc aacgcttgtc attatttctc caccaacccc      900
cttcacttcc ccttgtgcat cgttaccacc ctttataccc acctaccaga caccaacgct      960
ccagatttgc ttcggcccta acactctccg ttatatataa cccctttcatg aacaaggcta   1020 atc                                                                  1023

<210> SEQ ID NO 6
<211> LENGTH: 54
<212> TYPE: DNA
<213> ORGANISM: Phaseolus vulgaris

<400> SEQUENCE: 6
attcaccaca ttacgcacta cttttcctct ctccgtctcc tcattccttc attt            54

<210> SEQ ID NO 7
<211> LENGTH: 10608
<212> TYPE: DNA
<213> ORGANISM: Artificial sequence
<220> FEATURE:
<223> OTHER INFORMATION: synthetic sequence; construct; expression
      cassette used for the transformation of alfalfa

<400> SEQUENCE: 7
atcaagcttg gtcgagtggc ccgatccccg atctagtaac atagatgaca ccgcgcgcga      60
taatttatcc tagtttgcgc gctatatttt gttttctatc gcgtattaaa tgtataattg     120
cgggactcta atcataaaaa cccatctcat aaataacgtc atgcattaca tgttaattat     180
tacatgctta acgtaattca acagaaatta tatgataatc atcgcaagac cggcaacagg     240
attcaatctt aagaaacttt attgccaaat gtttgaacga tcgggaattg gggatcgaac     300
cccagagtcc cgctcagaag aactcgtcaa gaaggcgata gaaggcgatg cgctgcgaat     360
cgggagcggc gataccgtaa agcacgagga gcggtcagc ccattcgccg ccaagctctt      420
cagcaatatc acgggtagcc aacgctatgt cctgatagcg gtccgccaca cccagccggc     480
cacagtcgat gaatccagaa aagcggccat tttccaccat gatattcggc aagcaggcat     540
cgccatgcgt cacgacgaga tcctcgccgt cgggcatgcg cgccttgagc ctggcgaaca     600
gttcggctgg cgcgagcccc tgatgctctt cgtccagatc atcctgatcg acaagaccgg     660
cttccatccg agtacgtgct cgctcgatgc gatgtttcgc ttggtggtcg aatgggcagg     720
tagccggatc aagcgtatgc agccgccgca ttgcatcagc catgatggat actttctcgg     780
caggagcaag gtgagatgac aggagatcct gccccggcac ttcgcccaat agcagccagt     840
cccttcccgc ttcagtgaca acgtcgagca cagctgcgca aggaacgccc gtcgtggcca     900
gccacgatag ccgcgctgcc tcgtcctgca gttcattcag ggcaccggac aggtcggtct     960
tgacaaaaag aaccgggcgc ccctgcgctg acagccggaa cacggcggca tcagagcagc   1020
cgattgtctg ttgtgcccag tcatagccga atagcctctc cacccaagcg gccggagaac   1080
ctgcgtgcaa tccatcttgt tcaatcatgc gaaacgatcg tctagctaga gatccccgat   1140
cttgtagaga gagactggtg atttcagcgt gtcctctcca aatgaaatga acttccttat   1200
```

-continued

```
atagaggaag ggtcttgcga aggatagtgg gattgtgcgt catcccttac gtcagtggaa      1260
gtatcacatc aatccacttg cttttgaagac gtggttggaa cgtcttcttt ttccacgatg     1320
ctcctcgtgg gtgggggtcc atctttggga ccactgtcgg cagaggcatc ttgaatgata      1380
gcctttcctt tatcgcaatg atggcatttg taggtgccac cttcctttc tactgtcctt       1440
ttgatgaagt gacaggtagg atcggaaagc tagcttccac tcgaccaagc tttggcgcgc      1500
caaatcgtga agtttctcat ctaagccccc atttggacgt gaatgtagac acgtcgaaat      1560
aaagatttcc gaattagaat aatttgttta ttgctttcgc ctataaatac gacggatcgt      1620
aatttgtcgt tttatcaaaa tgtactttca ttttataata acgctgcgga catctacatt      1680
tttgaattga aaaaaaattg gtaattactc tttctttttc tccatattga ccatcatact      1740
cattgctgat ccatgtagat ttcccggaca tgaagccatt tacaattgaa tatatcctgc      1800
cgccgctgcc gctttgcacc cggtggagct tgcatgttgg tttctacgca gaactgagcc      1860
ggttaggcag ataatttcca ttgagaactg agccatgtgc accttccccc caacacggtg      1920
agcgacgggg caacggagtg atccacatgg gacttttcct agcttggctg ccattttgg       1980
ggtgaggccg ttcgcggccg aggggcgcag cccctgggg gatgggaggc ccgcgttagc       2040
gggccgggag ggttcgagaa ggggggcac ccccccttcgg cgtgcgcggt cacgcgcaca      2100
gggcgcagcc ctggttaaaa acaaggttta taaatattgg tttaaaagca ggttaaaaga      2160
caggttagcg gtgccgaaa acgggcgga aacccttgca aatgctggat tttctgcctg        2220
tggacagccc ctcaaatgtc aataggtgcg ccctcatct gtcagcactc tgcccctcaa       2280
gtgtcaagga tcgcgcccct catctgtcag tagtcgcgcc cctcaagtgt caataccgca      2340
gggcacttat ccccaggctt gtccacatca tctgtgggaa actcgcgtaa aatcaggcgt      2400
tttcgccgat ttgcgaggct ggccagctcc acgtcgccgg ccgaaatcga gcctgccct       2460
catctgtcgc gccgccctat accttgtctg cctccccgcg ttgcgtcgcg gtgcatggag      2520
ccgggccacc tcgacctgaa tggaagccgg cggcacctcg ctaacggatt caccactcca     2580
agaattggag ccaatcaatt cttgcggaga actgtgaatg cgcaaaccaa cccttggcag     2640
aacatatcca tcgcgtccgc catctccagc agccgcacgc ggcgcatctc gggcagcgtt     2700
gggtcctggc cacgggtgcg catgatcgtg ctcctgtcgt tgaggacccg gctaggctgg     2760
cggggttgcc ttactggtta gcagaatgaa tcaccgatac gcgagcgaac gtgaagcgac     2820
tgctgctgca aaacgtctgc gacctgagca acaacatgaa tggtcttcgg tttccgtgtt     2880
tcgtaaagtc tggaaacgcg gaagtcagcg ccctgcacca ttatgttccg gatctgcatc    2940
gcaggatgct gctggctacc ctgtggaaca cctacatctg tattaacgaa gcgctggcat    3000
tgaccctgag tgatttttct ctggtcccgc cgcatccata ccgccagttg tttaccctca    3060
caacgttcca gtaaccgggc atgttcatca tcagtaaccc gtatcgtgag catcctctct    3120
cgtttcatcg gtatcattac ccccatgaac agaaatcccc cttacacgga ggcatcagtg    3180
accaaacagg aaaaaaccgc ccttaacatg gcccgcttta tcagaagcca gacattaacg    3240
cttctggaga aactcaacga gctggacgcg gatgaacagg cagacatctg tgaatcgctt    3300
cacgaccacg ctgatgagct ttaccgcagc tgcctcgcgc gtttcggtga tgacggtgaa    3360
aacctctgac acatgcagct cccggagacg gtcacagctt gtctgtaagc ggatgccggg    3420
agcagacaag cccgtcaggg cgcgtcagcg ggtgttggcg ggtgtcgggg cgcagccatg    3480
acccagtcac gtagcgatag cggagtgtat actggcttaa ctatgcggca tcagagcaga    3540
ttgtactgag agtgcaccat atgcggtgtg aaataccgca cagatgcgta aggagaaaat    3600
```

```
accgcatcag gcgctcttcc gcttcctcgc tcactgactc gctgcgctcg gtcgttcggc    3660
tgcggcgagc ggtatcagct cactcaaagg cggtaatacg gttatccaca gaatcagggg    3720
ataacgcagg aaagaacatg tgagcaaaag gccagcaaaa ggccaggaac cgtaaaaagg    3780
ccgcgttgct ggcgtttttc cataggctcc gcccccctga cgagcatcac aaaaatcgac    3840
gctcaagtca gaggtggcga aacccgacag gactataaag ataccaggcg tttccccctg    3900
gaagctccct cgtgcgctct cctgttccga cctgccgct taccggatac ctgtccgcct    3960
ttctcccttc gggaagcgtg gcgctttctc atagctcacg ctgtaggtat ctcagttcgg    4020
tgtaggtcgt tcgctccaag ctgggctgtg tgcacgaacc ccccgttcag cccgaccgct    4080
gcgccttatc cggtaactat cgtcttgagt ccaacccggt aagacacgac ttatcgccac    4140
tggcagcagc cactggtaac aggattagca gagcgaggta tgtaggcggt gctacagagt    4200
tcttgaagtg gtggcctaac tacggctaca ctagaaggac agtatttggt atctgcgctc    4260
tgctgaagcc agttaccttc ggaaaaagag ttggccggca acaaaccac cgctggtagc    4320 ggtggttttt ttgtttgcaa gcagcagatt acgcgcagaa aaaaaggatc tcaagaagat    4380
cctttgatct tttctacggg gtctgacgct cagtggaacg aaaactcacg ttaagggatt    4440
ttggtcatga gattatcaaa aaggatcttc acctagatcc ttttaaatta aaaatgaagt    4500
tttaaatcaa tctaaagtat atatgagtaa acttggtctg acagttacca atgcttaatc    4560
agtgaggcac ctatctcagc gatctgtcta tttcgttcat ccatagttgc ctgactcccc    4620
gtcgtgtaga taactacgat acgggagggc ttaccatctg gccccagtgc tgcaatgata    4680
ccgcgagacc cacgctcacc ggctccagat ttatcagcaa taaaccagcc agccggaagg    4740
gccgagcgca gaagtggtcc tgcaacttta tccgcctcca tccagtctat taattgttgt    4800
cgggaagcta gagtaagtag ttcgccagtt aatagtttgc gcaacgttgt tgccattgct    4860
gcaggtcggg agcacaggat gacgcctaac aattcattca agccgacacc gcttcgcggc    4920
gcggcttaat tcaggagtta aacatcatga gggaagcggt gatcgccgaa gtatcgactc    4980
aactatcaga ggtagttggc gtcatcgagc gccatctcga accgacgttg ctggccgtac    5040
atttgtacgg ctccgcagtg gatggcggcc tgaagccaca cagtgatatt gatttgctgg    5100
ttacggtgac cgtaaggctt gatgaaacaa cgcggcgagc tttgatcaac gaccttttgg    5160
aaacttcggc ttcccctgga gagagcgaga ttctccgcgc tgtagaagtc accattgttg    5220
tgcacgacga catcattccg tggcgttatc cagctaagcg cgaactgcaa tttggagaat    5280
ggcagcgcaa tgacattctt gcaggtatct tcgagccagc cacgatcgac attgatctgg    5340
ctatcttgct gacaaaagca agagaacata gcgttgcctt ggtaggtcca gcggcggagg    5400
aactctttga tccggttcct gaacaggatc tatttgaggc gctaaatgaa accttaacgc    5460
tatggaactc gccgcccgac tgggctggcg atgagcgaaa tgtagtgctt acgttgtccc    5520
gcatttggta cagcgcagta accggcaaaa tcgcgccgaa ggatgtcgct gccgactggg    5580
caatggagcg cctgccggcc cagtatcagc ccgtcatact tgaagctagg caggcttatc    5640
ttggacaaga agatcgcttg gcctcgcgcg cagatcagtt ggaagaattt gttcactacg    5700
tgaaaggcga gatcaccaag gtagtcggca ataatgtctc aacaattcgt tcaagccgac    5760
gccgcttcgc ggcgcggctt aactcaagcg ttagatgctg caggcatcgt ggtgtcacgc    5820
tcgtcgtttg gtatggcttc attcagctcc ggttcccaac gatcaaggcg agttacatga    5880
tcccggccgc ccttcggtcc tccgatcgag gattttcgg cgctgcgcta cgtccgcgac    5940
cgcgttgagg gatcaagcca cagcagccca ctcgaccttc tagccgaccc agacgagcca    6000
```

```
agggatcttt ttggaatgct gctccgtcgt caggctttcc gacgtttggg tggttgaaca      6060
gaagtcatta tcgcacggaa tgccaagcac tcccgagggg aaccctgtgg ttggcatgca      6120
catacaaatg gacgaacgga taaaccttt cacgcccttt aaatatccg attattctaa       6180
taaacgctct tttctcttag gtttacccgc aatatatcc tgtcaaacac tgatagttta      6240
aactgaaggc gggaaacgac aatctgatcc ccatcaagct agcttctgca ggtcctgctc      6300
gagcggccgc ggggaattcc cgatctagta acatagatga caccgcgcgc gataatttat      6360
cctagtttgc gcgctatatt ttgttttcta tcgcgtatta aatgtataat tgcgggactc      6420
taatcataaa aacccatctc ataaataacg tcatgcatta catgttaatt attacatgct      6480
taacgtaatt caacagaaat tatatgataa tcatcgcaag accggcaaca ggattcaatc      6540
ttaagaaact ttattgccaa atgtttgaac gatcggccgc ggcccgatca cacctcccac      6600
tttaacaaga tcaattaacc tcttatggta gttgaggtaa ttgtctttgt cagcatccac      6660
aaaaatgaaa tcgtagctac catgattctt ttcgtctttg atcatttcat caagaactgg      6720
aagagctgga ccttctctga aatcaatttt gtgatcaaca ccagcttttt taattacagg      6780
tagacccaat tcgtaatttt ctttgttaat gtccatagcc aaaatctttc catcttcagg      6840
aatagctagg gcagtggcaa ggagggagta gccagtgtag actctagatg tcttcccaag      6900
agaacatgaa gccatgaaag agttgagaga ggtcacagca aaacacccat ggaacatcat      6960
gacaacctct gcagatgaag gacaattttt gagcatgctc cttaaactta tcaatgctaa      7020
gaataccatg gaaattggtg tctacactgg ctactccctc cttgccactg ccctagctat      7080
tcctgaagat ggaagagatt tggctatgga cattaacaaa gaaaattacg aattgggtct      7140
acctgtaatt aaaaaagctg gtgttgatca caaattgat ttcagagaag gtccagctct       7200
tccagttctt gatgaaatga tcaaagacga aagaatcat ggtagctacg atttcatttt       7260
tgtggatgct gacaaagaca attacctcaa ctaccataag aggttaattg atcttgttaa      7320
agtgggaggt gtgatcggt acgacaacac cttatggaat ggatctgtgg ttgcacccc        7380
tgatgctcca ttgaggaagt atgttaggat ccgcgagatc cccggaaatg aaggaatgag      7440
gagacggaga gaggaaaagt agtgcgtaat gtggtgaatg attagccttg ttcatgaagg      7500
ggttatatat aacggagagt gttagggccg aagcaaatct ggagcgttgg tgtctggtag      7560
gtgggtataa agggtggtaa cgatgcacaa ggggaagtga aggggggtgg tggagaaata      7620
atgacaagcg ttggattacc agcctgcatc agcggctctc attgcgcgac gtggcatttt      7680
ttctccccctt ctctgggtgc gatgtcacct tgtggactag aacctaactt ctctgtactt     7740
ccctaccaac acaggacgtg aatagaaga tagacgtata aatcaatcaa ttaattaatt       7800
aattgattaa ttaataaatg ttacccaact acgaaattaa attcctaatc cttacatttt      7860
ctggttcctt ttaacaaaga tttcaacgta catattatct tttctaggta tatatatata      7920
tatatatata tatatata tataagaaga acaaagggc aaggaatcgc aaccaatcat         7980
tcatcttttg tcttcttctc actaaaaaaa aacatagtta aagtgaacta tgattcctgg      8040
gaattggctt ctaaaactgg ttaaataggg ttagaaagat aaaaataaat aaataaatgt      8100
gtttctttag catttgtttt agtaattact tagaagaaag gacacggatt tacagataac      8160
aagaaagaaa tgaaaagaaa aagtgtgata atagaaaaaa aatggagca agaaaacgac        8220
agggccgcca tgccagagtg tggggggaggt agagaaatta agatgcagct agtatttatg     8280
gcaggtgtta ctatttagaa aagtaagttt aagattcaac tacaacttcg gctagggttt      8340
aactcatcat cttttagaatt gtagatccctt tcaactaaat cactccacag ggattggtta   8400
```

```
tattgaatta atatacaaaa ccagttcatc ttcttgttac tattggcttg aacataaatg    8460
ttaagcataa ataaaaaata atgaatattg gcttagactt ttcgagctcg aattcggtac    8520
caagctttgg cgcgccaaat cgtgaagttt ctcatctaag cccccatttg gacgtgaatg    8580
tagacacgtc gaaataaaga tttccgaatt agaataattt gtttattgct ttcgcctata    8640
aatacgacgg atcgtaattt gtcgttttat caaaatgtac tttcatttta taataacgct    8700
gcggacatct acatttttga attgaaaaaa aattggtaat tactctttct ttttctccat    8760
attgaccatc atactcattg ctgatccatg tagatttccc ggacatgaag ccatttacaa    8820
ttgaatatat cctgccgccg ctgccgcttt gcacccggtg gagcttgcat gttggtttct    8880
acgcagaact gagccggtta ggcagataat ttccattgag aactgagcca tgtgcacctt    8940 cccccccaaca cggtgagcga cggggcaacg gagtgatcca catgggactt ttcctagctt    9000
ggccggccat gactatcgtc gccgcactta tgactgtctt ctttatcatg caactcgtag    9060
gacaggtgcc ggcagcgctc tgggtcattt tcggcgagga ccgctttcgc tggagcgcga    9120
cgatgatcgg cctgtcgctt gcggtattcg gaatcttgca cgcctcgct caagccttcg    9180 tcactggtcc cgccaccaaa cgtttcggcg agaagcaggc cattatcgcc ggcatggcgg    9240
ccgacgcgct gggctacgtc ttgctggcgt tcgcgacgcg aggctggatg ccttccccca    9300
ttatgattct tctcgcttcc ggcggcatcg ggatgcccgc gttgcaggcc atgctgtcca    9360
ggcaggtaga tgacgaccat cagggacagc ttcaaggatc gctcgcggct cttaccagcc    9420
taacttcgat cattggaccg ctgatcgtca cggcgattta tgccgcctcg gcgagcacat    9480
ggaacgggtt ggcatggatt gtaggcgccg ccctatacct tgtctgcctc cccgcgttgc    9540
gtcgcggtgc atggagccgg gccacctcga cctgaatgga agccggcggc acctcgctaa    9600
cggattcacc actccaagaa ttggagccaa tcaattcttg cggagaactg tgaatgcgca    9660
aaccaaccct tggcagaaca tatccatcgc gtccgccatc tccagcagcc gcacgcggcg    9720
catctcgggc agcgttgggt cctggccacg ggtgcgcatg atcgtgctcc tgtcgttgag    9780
gacctggcta ggctggcggg gttgccttac tggttagcag aatgaatcac cgatacgcga    9840
gcgaacgtga agcgactgct gctgcaaaac gtctgcgacc tgagcaacaa catgaatggt    9900
cttcggtttc cgtgtttcgt aaagtctgga aacgcggaag tcagcgccct gcaccattat    9960
gttccggatc tgcatcgcag gatgctgctg gctaccctgt ggaacaccta catctgtatt   10020
aacgaagcgc tggcattgac cctgagtgat ttttctctgg tcccgccgca tccataccgc   10080
cagttgttta ccctcacaac gttccagtaa ccgggcatgt tcatcatcag taacccgtat   10140
cgtgagcatc ctctctcgtt tcatcggtat cattacccct tcggtcctcc gatcgaggat   10200
ttttcggcgc tgcgctacgt ccgcgaccgc gttgagggat caagccacag cagcccactc   10260
gaccttctag ccgacccaga cgagccaagg gatcttttg gaatgctgct ccgtcgtcag   10320
gctttccgac gtttgggtgg ttgaacagaa gtcattatcg cacggaatgc caagcactcc   10380 cgagggaac cctgtggttg gcatgcacat acaaatggac gaacggataa accttttcac   10440
gcccttttaa atatccgatt attctaataa acgctctttt ctcttaggtt tacccgccaa   10500
tatatcctgt caaacactga tagtttaaac tgaaggcggg aaacgacaat ctgatcccca   10560
tcaagctagc ttctgcaggt cctgctcgag cggccgctct agaactag               10608
```